US006936705B1

(12) United States Patent
Honjo et al.

(10) Patent No.: US 6,936,705 B1
(45) Date of Patent: Aug. 30, 2005

(54) HUMAN IMMUNOGLOBULIN $V_H$ GENE SEGMENTS AND DNA FRAGMENTS CONTAINING THE SAME

(75) Inventors: Tasuku Honjo, Kyoto (JP); Fumihiko Matsuda, Kyoto (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 09/515,697

(22) Filed: Feb. 29, 2000

Related U.S. Application Data

(63) Continuation of application No. 08/545,809, filed as application No. PCT/JP93/00603 on May 10, 1993, now Pat. No. 6,096,878.

(51) Int. Cl.$^7$ .................... C07H 21/04; C12N 15/63; C12N 5/10; C12N 1/21; C12N 1/15
(52) U.S. Cl. ............... 536/23.53; 536/23.1; 536/23.5; 435/320.1; 435/325; 435/326; 435/252.3; 435/254.11
(58) Field of Search ...................... 536/23.53, 23.1, 536/23.5; 435/320.1, 325, 326, 252.3, 254.11, 320.4

(56) References Cited

U.S. PATENT DOCUMENTS 5,545,806 A * 8/1996 Lonberg et al.

FOREIGN PATENT DOCUMENTS

| JP | 4-504365 | 8/1992 |
| JP | 5-501062 | 3/1993 |
| WO | WO 91/10741 | 7/1991 |
| WO | WO 91/18983 | 12/1991 |

OTHER PUBLICATIONS

Old and Primrose (Principles of Gene Manipulation, 4th edition, 1989, pp. 70–72).*
Abstract of Charreau et al (Transgene Research, 1996, vol. 5, pp. 223–234).*
Abstract of Nancarrow et al (Methods in molecular biology, 1993, vol. 18, pp. 273–303).*
Abstract of Machaty et al (Cloning Stem Cells, 2002, vol. 4, pp. 21–27).*
Abstract of Bellanne–Chantelot et al (Nucleic Acids Research, 1991, vol. 19, pp. 505–510).*
Kabat, Sequences of Proteins of Immunological Interest, 1991, 3 volumnes, National Institutes of Health.*
Roitt et al., *Immunology*, Second Edition, 6.3–6.5, 1989.
New Riverside University Dictionary, "gene" 1984.
Illustrated Dictionary of Immunology, Cruse et al., 189, 1994.
Shin et al., "Physical map of the human immunoglobulin heavy chain locus: clustering of autoantibody–related variable segments in one haplotype"; The EMBO Journal vol. 10 No. 12:3641–3645, 1991.

International Search Report; PCT/JP93/00603; Jul. 30, 1993; J. Zahra.
The Journal of Immunology, vol. 149, No. 4, (1992), E.H. Sasso et al.; "$V_H$ genes in tandem array comprise related germline motif"; p. 1230–1236.
The Journal of Immunology, vol. 148, No. 9, (1992) K.W. van Dijk et al., "Mapping of human H chain V region genes ($V_H$4) using deletional analysis and pulsed field gel electrophoresis"; p. 2923–2931.
European Journal of Immunology, vol. 23, No. 4, (1993) X. Mariette et al., "Nucleotidic sequence analysis of four human monoclonal IgM with an antibody activity to myelin–associated glycoprotein"; p. 846–851.
Blood, vol. 76, No. 10 (1990) O.G. Jonsson et al., "Detection of minimal residual disease in acute lympho–blastic leukemia using immunoglobulin hypervariable region specific oligo–nucleotide probes", p. 2072–2079.
Article; "Structure and Physical Map of 64 Variable Segments . . . Heavy–Chain Locus"; Nature Genetics; vol. 3; Jan. 1993; pp. 88–94.
"The Repertoire of Human Germline $V_H$ Sequences . . . Hypervariable Loops"; 1992 Academic Press Limited; J. Mol. Biol. 227; pp. 776–798.
"Immunoglobulin Heavy and Light Chain . . . Germline Genes"; Immunology Letters 34 (1992); pp, 57–62; Elsevier Science Publishers B.V.
"Nucleotide Sequences of the cDNAs . . . HIV–1—gp41"; Nucleic Acids Research; vol. 18, No. 16; 1990 Oxford University Press; p. 4927.
"Expression of Members of the Immunoglobulin . . . Leukemia"; International Immunology; vol. 4, No. 3; pp. 313–320.
"Content and Organization of the Human Ig . . . Locus"; The EMBO Journal; vol. 7, No. 3; pp. 737–738; 1988.
"The Human Cord Blood Antibody . . . Family"; Eur. J. Immunol. 22 (1992) pp. 241–245.
"Early Restriction of the Human Antibody Repertoire"; Science vol. 238 (1987); pp. 791–793.
"Preferential Utilization of Conserved Immunoglobulin . . . Life"; Proc. Natl. Acad. Sci. U.S.A. vol. 87 (1990) pp. 6146–6150.
"Restricted Ig H Chain V Gene Usage . . . Polysaccharide"; J. Immunol. vol. 147 (1991); pp. 1667–1674.
"$V_H$ Sequence of a Human Anti–Sm . . . Germline Genes"; J. Immunol. vol. 142 (1989); pp. 883–887.

(Continued)

*Primary Examiner*—Karen A. Canella
(74) *Attorney, Agent, or Firm*—Fish & Richardson P.C.

(57) ABSTRACT

Novel human immunoglobulin $V_H$ segments and DNA fragments containing the same are disclosed. The DNA fragment according to the present invention is the fragment having a size of about 800 kbp which is shown in FIG. 1. The human immunoglobulln $V_H$ segments according to the present invention are contained in the fragment of this DNA fragment of about 800 kbp, and there are 50 novel segments. The base sequences of these segments are shown in the Sequence Listing. The present invention also provides DNA fragments which contain two or more of these $V_H$ segments.

14 Claims, 4 Drawing Sheets

OTHER PUBLICATIONS

"The Role of Clonal Selection . . . Lymphoma"; J. Exp. Med. vol. 174 (1991); pp. 525–537.
"Structural Analyses of Human Developmentally Regulated Vh3 Genes"; Scand. J. Immunol. vol. 31 (1990); pp. 257–267.
"Relationship of Human Variable Region . . . Autoantibodies"; J. Immunol. vol. 139 (1987); pp. 2496–2501.
Nucleotide Sequences of the cDNAs . . . Tumor Cells; Nucleic Acids Res.; vol. 17, No. 11 (1989; p. 4385.
"Structure and Multiplicity of Genes . . . Region"; Proc. Natl. Acad. Sci. U.S.A. vol. 77 (1980); pp. 6561–6465.
"Nucleotide Sequences of Eight Human . . . Families"; J. Immunol. vol. 142 (1989); pp. 4054–4061.
"Early Human IgH Gene Assembly . . . Cell Lines"; J. Exp. Med. vol. 169 (1989); pp. 1391–1403.
"Presence of Immunoglobulin (Ig) M and IgG . . . Immunodeficiency"; J. Clin. Invest. vol. 85 (1990); pp. 1722–1727.
"Analysis of Variable Region Genes . . . Origin"; J. Immunol. 143 (1989); pp. 685–691.
"Molecular Basis of an Autoantibody–associated Restriction Fragment Length . . . Diseases"; J. Clin. Invest. vol. 88 (1991); pp. 193–203.
"The Complete Nucleotide Sequences . . . Rheumatoid Arthritis"; J. Clin. Invest. vol. 86 (1990); pp. 1320–1328.
"Relationship of Variable Region Geneses . . . Autoantibodies"; J. Exp. Med. vol. 169 (1989); pp. 1631–1643.
"Complete Sequence of the Genes Encoding . . . Arthritis Patient"; Int. Immunol. vol. 3 (1991); pp. 865–875.
"Evolutionary Aspects of Immunoglobulin . . . Subgroups"; Proc. Natl. Acad. Sci. U.S.A. vol. 80 (1983) pp. 855–859.
"Human Heavy–Chain Variable Region . . . Leukemia"; Proc. Natl. Acad. Sci. U.S.A. vol. 84 (1987); pp. 8563–8567.
"The Smaller Human $V_H$ Gene . . . Polymorphism"; EMBO J. vol. 8 (1989); pp. 3471–3478.
"Organization and Evolution of Immunoglobulin $V_H$ Gene Subgroups"; Proc. Natl. Acad. Sci. U.S.A. vol. 79, (1982); pp. 4405–4409.
"A New Human Immunoglobulin . . . B–Cell Tumours"; Nature vol. 331 (1988); pp. 446–449.
"Chromosomal Organization . . . Family"; J. Immunol. vol. 150 (1993.4); pp. 2858–2868.
"The Human Immunoglobulin . . . Locus "; Eur. J. Immunol. vol . 23 (1993); pp. 832–839.

"Rapid Screening of a Human Genomic Library . . . Sequences"; Proc. Natl. Acad. Sci. U.S.A. vol. 86 (1989) pp. 5898–5902.
"Transfer of a Yeast Artificial Chromosome . . . Cells"; Proc. Natl. Acad. Sci. U.S.A. vol. 87(1990) pp. 5109–5113.
"The Human HPRT Gene on a Yeast Artificial Chromosome . . . Fusion"; Genomics vol. 9 (1991) pp. 742–750.
"Structure of the Human Immunoglobulin . . . D Genes"; Cell vol. 27 (1981); pp. 583–591.
"Meiotic Recombination Between Yeast Artificial Chromosomes . . . Protooncogene", Proc. Natl. Acad. Sci. U.S.A. vol. 87 (1990); pp. 9913–9917.
"Chromosomal Region of the Cystic Fibrosis . . . Mapping"; Science vol. 250 (1990); pp. 94–98.
"Meiotic Recombination and Segregation . . . Cerevisiae"; Proc. Natl. Acad. Sci. U.S.A. vol. 89 (1992); pp. 5296–5300.
"Mitotic Recombination of Yeast Artificial Chromosomes"; Nucleic Acid Research vol. 20, No. 12; pp. 3135–3138.
"Rescue of End Fragments of Yeast . . . in Yeast"; Nucleic Acids Res. vol. 19 (1991); pp. 4943–4948.
"Second–Generation Approach to the Construction . . . Libraries"; Genomics vol. 8 (1990); pp. 297–303.
"Guide to Yeast Genetics and Molecular Biology"; (1991); pp. 251–270.
"Sequences of Proteins of Immunological Interest", 5th Edition (1991).
"Systematic Screening of Yeast Artificial–Chromosome . . . Reaction"; Proc. Natl. Acad. Sci. U.S.A. vol. 87 (1990); pp. 1213–1217.
"Cloning of Human Immunoglobulin . . . Genes"; Proc. Natl. Acad. Sci. U.S.A. vol. 79 (1982); pp. 3833–3837.
"Organization and Evolution of Variable Region . . . Chain"; J. Mol. Biol. Vol. 190 (1986); pp. 529–541.
"Rearranged Immunoglobulin Heavy Chain . . . Region"; Proc. Natl. Acad. Sci. U.S.A. vol. 81 (1984); pp. 5194–5198.
"A Novel Family of Variable . . . Chain"; J. Mol. Biol. Vol. 195 (1987); pp. 761–768.
"A Novel, Rapid Method for the Isolation . . . Clones"; Nucleic Acids Res. vol. 18 (1990); pp. 2887–2890.
"Recombinant Fragment Assay . . . Reaction"; Nucleic Acids Res. vol. 16 (1988); pp. 8887–8903.

* cited by examiner

HUMAN IMMUNOGLOBULIN $V_H$ GENE SEGMENTS AND DNA FRAGMENTS CONTAINING THE SAME

This application is a continuation and claims the benefit of priority under 35 USC § 120 of application Ser. No. 08/545,809, filed Mar. 27, 1996, now U.S. Pat. No. 6,06,878 which claims the benefit of priority of PCT/JF93/60603, filed May 10, 1993.

TECHNICAL FIELD

This invention relates to novel human immunoglobulin $V_H$ gene segments and DNA fragments containing the same. The segments and DNA fragments according to the present invention are useful for producing human antibodies using a mammalian host by a genetic engineering process.

BACKGROUND ART

Immunoglobulins are composed of the L chains and H chains, each of which consists of a variable region (V region) and a constant region (C region) that has a structure common to immunoglobulin molecules. What determines the antigenic specificity of an antibody is the V region. The V region of the H chain is encoded by V, D (diversity) and J (joining) genes (The gene of the H chain is expressed by placing a suffix "H", like "$V_H$"). One of the important reasons why the V regions of immunoglobulins are highly diverse and can provide antibodies which specifically binds to infinite number of antigens is the rearrangement of V, D and J genes. That is, there are a plurality of V genes, D genes and J genes, respectively and they are randomly combined in somatic cells to form a gene encoding a single mRNA. Since the combination is randomly selected, wide variety of immunoglobulin V regions are provided.

On the other hand, antibodies currently employed for therapies of various diseases are those originated from animals other than human, such as mouse. However, if these antibodies are administered to human, since the antibodies are of exogenous origin, an immunological response occurs in the human body to present allergy and to neutralize the antibodies. To overcome this problem, it is desired to use antibodies originated from human for the therapies for human. Further, if a human antibody is industrially produced using human as the host and using a human-originated antigen, a problem of immunological tolerance is brought about, so that this approach employing the known method is very difficult. Thus, the production of human immunoglobulins by a genetic engineering process using an animal as a host is now being developed (for example, Japanese Laid-open PCT Application (Kohyo) No. 4-504365; Proc. Natl. Acad. Sci. USA, Vol. 86, pp.5898–5902, August 1989; Proc. Natl. Acad. Sci. USA, Vol. 87, pp.5109–5113, July 1990; Genomics 9, 742–750 (1991)). However, in the conventional methods in which human immunoglobulin genes are expressed in host animals other than human, there is a problem that the number of human $V_H$ segments provided for the genetic recombination is very small, so that the diversity of the expressed human immunoglobulins is limited. Even if only one $V_H$ segment is recombined, the diversity of the immunoglobulin is assured to some degree because of the combination with D and J genes. However, as mentioned above, since the diversity of immunoglobulins is determined by the rearrangement (random combination) of V gene segments, the more the human $V_H$ segments recombined, the higher the diversity of the immunoglobulins expressed. If the diversity of immunoglobulins is increased, not only antibodies against a number of antigens can be formed, but also the possibility of forming an antibody having a high specificity to a given antigen is promoted. Therefore, it in important for therapies and diagnoses to recombine $V_H$ segments as many as possible.

DISCLOSURE OF THE INVENTION

Accordingly, an object of the present invention is to provide a DNA fragment comprising a plurality of human immunoglobulin $V_H$ segments. Another object of the present invention is to provide a novel human immunoglobulin $V_H$ segments.

The present inventors intensively studied to succeed in determining human immunoglobulin H chain V region gene segments having a size of about 800 kb and in determining DNA sequences of 64 human $V_H$ segments contained therein. This made it possible to provide this DNA fragment of 800 kb and various DNA fragments contained therein, thereby completing the present invention.

That is, the present invention provides a DNA fragment having a size of about 800 kbp and having the structure shown in FIG. 1. It should be noted that in FIG. 1, the 64 human $V_H$ segments are those having DNA sequences shown in Sequence ID Nos. 1, 2, . . . 63, and 64, respectively, in the order from downstream (i.e., from the side near the $J_H$ gone).

The present invention also provides DNA fragments containing at least two consecutive functional human $V_H$ segments which are contained in said DNA fragment of about 800 kb according to the present invention.

The present invention further provides DNA fragments Y20, Y103, Y21, Y6, Y-24, M131, M118, M84 and 3-31, which have been deposited.

The present invention still further provides DNA fragments consisting essentially of at least two optional DNA fragments linked in an optional order, each of which contains at least two consecutive functional human $V_H$ segments contained in the DNA fragment of about 800 kb according to the present invention.

The present invention still further provides DNA fragments consisting essentially of at least two DNA fragments selected from the group consisting of DNA fragments Y20, Y103, Y21, Y6, Y-24, M131, M118, M84 and 3–31 which have been deposited, which are linked in an optional order.

The present invention still further provides novel human immunoglobulin $V_H$ segments having DNA sequences shown in Sequence ID Nos. 6, 7, 8, 9, 10, 11, 12, 13, 14, 15, 16, 17, 18, 19, 20, 21, 22, 23, 24, 25, 26, 27, 29, 30, 31, 32, 33, 34, 35, 36, 37, 38, 40, 41, 42, 43, 44, 45, 46, 47, 48, 49, 50, 51, 52, 53, 54, 55, 63 and 64, respectively.

By the present invention, novel hu,an immunoglobulin $V_H$ segments and DNA fragments containing the same were provided. The DNA fragment of about 800 kb according to the present invention contains as many as 64 human immunoglobulin $V_H$ segments. Thus, by producing human immunoglobulins by a host animal using this DNA fragment, the diversity of the produced human immunoglobulin is largely increased when compared with the conventional methods.

BEST MODE FOR CARRYING OUT THE INVENTION

Figure 1:
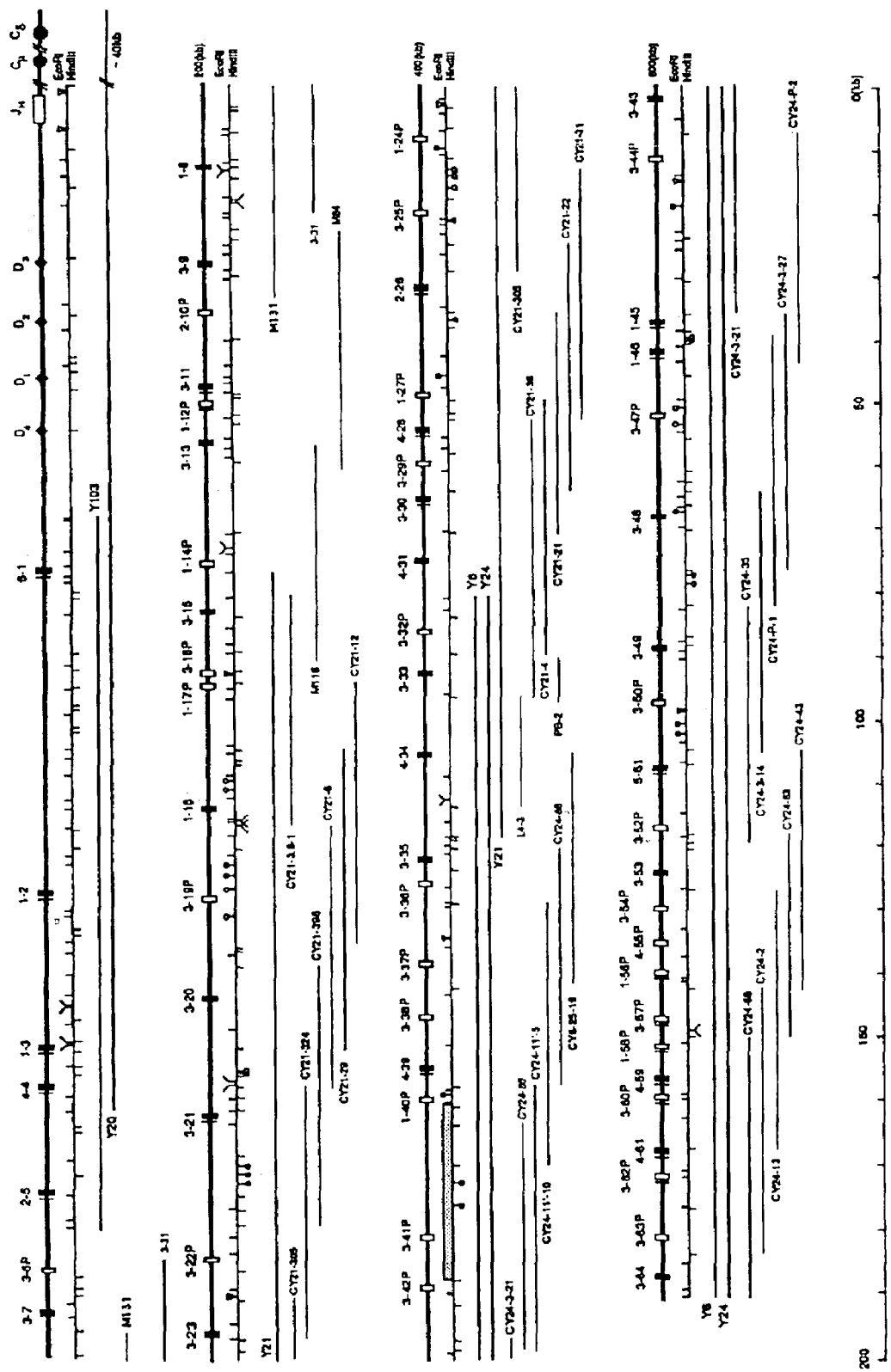
FIG. 1 shows a genetic map of the DNA fragment of about 0.8 Mb according to the present invention.

The present inventors prepared a library by inserting the DNA partially digested with Eco RI into YAC by the method detailed in the examples hereinbelow described, which DNA was originated from human lymphoblastoid cell line transformed by EB virus, and succeeded in determining the structure of human $V_H$ gene region having a size of about 600 kbp using the above-mentioned library. The structure is shown in FIG. 1. In FIG. 1, the genetic map is shown on the four thick solid lines. The right side of each solid line is the 3' side and the left end of the upper most solid line continues to the right end of the second solid line. In the DNA fragment shown in FIG. 1, there exist C genes, $J_H$ genes and D genes in the order mentioned from the 3' end. Subsequent to the D genes, there are 64 $V_H$ segments. The DNA sequences of all of these 64 $V_H$ segments have been determined as described in the examples below, and Sequence ID Nos. 1, 2, ... 63, 64 were assigned to the 64 $V_H$ segments in the order from downstream. Among these $V_H$ segments, the functional $V_H$ segments which are thought to encode polypeptides are indicated by solid rectangles. On the other hand, those which have the general features of the known $V_H$ segments but do not presently encode polypeptides because of the termination codons contained therein, that is, pseudo $V_H$ segments are indicated by hollow rectangles. Immediately below the genetic map, restriction maps by Eco RI and gd III are shown. The restriction sites are indicated by short perpendicular lines. The short lines to which ends circles are attached are those whose order is not determined, and the dotted boxes indicate the regions in which Eco RI sites have not been determined. In FIG. 1, the symbol which looks like "Y" indicates the sites at which two restriction sites are close. In FIG. 1, restriction sites of Nlu I are indicated by hollow triangles and restriction sites of Not I are indicated by solid triangles. The fragments inserted in the clones employed for determining the structure of the DNA fragment are shown thereunder. The structure of the 3' side farther than the 3' end shown in FIG. 1 is known and described in Ravetch, J. V. et al., (1981) Cell, Vol. 27, pp.593–591.

Among the DNA fragments inserted in the clones shown in FIG. 1, the yeasts each of which contains YAC clode Y20, Y103, Y21, Y6 and Y24 respectively have been deposited with the International Patent Organism Depository (IPOD), Agency of Industrial Science and Technology (AIST), Tsukuba Central 6 at 1-1, Higashi 1-chome, Tsukuba-shi, Ibaraki-Ken 305-8566, Japan, which is an International Depository Authonity (IDA) listed in MPEP § 2405 as being recognked under the Budapest Treaty, on April 22, 1993 under accession numbers FERM BP-4272, FERbM BP-4275, FERM BP-4273. FERM BP-4271 and FERM BP-4274, respoctively. The E.coli ceuls each of which contains cosmid clone M131, M118, M84 and 3–31, respectively have been deposited with the IPOD, AIST Tsukuba Central 6 at 1-1, Higashi l-chome, Tsuba-shi, Ibaraki-Ken 305-8566, Japan, which is an IDA listed in MPEP § 2405 as being recognized under the Budapest Treaty, on Apr. 22, 1993 under accession numbers FERM BP4279, FERM BP-4278, FERM BP4277 and FERM BP4276 respectively.

The DNA fragment having a size of about 800 kbp shown in FIG. 1 can be prepared by linking these deposited DNA fragments by known methods. That is, a DNA fragment A and a DNA fragment B whose DNA sequence at its terminal region overlaps with the DNA sequence of the terminal region of DNA fragment A (i.e., the DNA sequence of the 3' region of DNA fragment A is identical to the DNA sequence of the 5' region of DNA fragment B) can be easily ligated by a method exploiting genetic recombination in the yeast cells. More particularly, DNA fragments A and B are inserted in separate YAC vectors, and the resulting recombinant YAC vectors are introduced in separate mating type yeast cells, respectively. The resulting yeast cells are then fused. By this, genetic recombination occurs in the yeast host to form a YAC having a DNA fragment in which DNA fragment A and DNA fragment B are ligated, which has only one overlapping region located at the terminal regions of DNA fragments A and B. The thus formed recombinant YAC can easily be selected using the auxotrophy encoded in the YAC as a marker. This method is well-known in the art, and is described in, for example, Japanese Laid-open PCT Application (Kohyo) No. 4-504365; Proc. Natl. Acad. Sci. USA, Vol. 87, pp.9913–9917, December 1990; Science Vol. 250, p.94, Proc. Natl. Acad. Sci. USA, Vol. 89, pp.5296–5300, June 1992; and Nucleic Acid Research, Vol. 20, No. 12, pp.313S–3138. Since the terminal regions of each of the deposited 8 DNA fragments overlap the respective terminal regions of the adjacent DNA fragments, they can be ligated sequentially by the method described above. Although DNA fragments 3–31, M84, m118 and M-131 are cloned in cosmid vectors, they can be kept in an artificial chromosome in the yeast cell by cutting the recombinant cosmid with a restriction enzyme having a restriction site only in the cosmid vector, and ligating a YAC vector to the ends of the digested recombinant cosmid vector. Further, by the above-described method, the digested recombinant vector can be ligated to a YAC clone of other regions. It should be noted that even if the above-mentioned 9 deposited fragments are ligated, a gap of about 4 kb still remains. A DNA fragment which fills the gap can be easily prepared by the method described below. That is, as shown in FIG. 1, since the Hind III fragment including the region of the gap is relatively large, this Hind III fragment can be obtained by completely digesting human genome by Hind III, electrophoresing the resultant, selecting DNA fragments having sizes of about 15 kb, detecting the desired fragment with a probe, and recovering the detected desired fragment. The probe used here can be isolated as follows. That is, the DNA fragments located at the both ends of the gap are subcloned using a plasmid and DNA fragments which do not contain a repetitive sequence are prepared therefrom. The thus obtained fragments are then used for screening of the library. Only those detected by the probes which are the DNA fragments at both ends of the gap are isolated.

As described above, the DNA fragment of about 800 kbp shown in FIG. 1 was provided according to the present invention. The fragments consisting of the DNA region included in this DNA fragment can also be used for producing human immunoglobulin by a genetic engineering method. More particularly, to increase the diversity of human immunoglobulin produced by a genetic engineering method, it is preferred to incorporate a fragment containing human $V_H$ segments as many as possible. However, if the fragment contains at least two human $V_H$ segments, the diversity to some degree is given during rearrangement, so that the fragment can be employed. Thus, DNA fragments consisting of a region containing at least two consecutive functional $V_H$ segments, which region is contained in the DNA of about 800 kb shown in FIG. 1 can be employed and are useful. The number of the functional $V_H$ segments contained in such DNA fragments is at least two, and is preferably not less than 6. The more the number of the functional $V_H$ segments, the higher the diversity of the human immunoglobulin produced, so that the more preferred. Thus, the preferableness is increased when the number of the functional $V_H$ segments in 7, 8, 9, 10, 11, 12, 13, 14, 15, 16, 17, 18, 19, 20, 21, 22, 23, 24, 25, 26, 27, 28, 29, 30, 31, 32 and 33, with the order mentioned. Among these fragments, although those having large molecular weights are cloned into YAC vector, small fragments having a size of about not more than 50 kb are not necessarily cloned into YAC vector, but can be cloned into cosmid vectors and plasmid vectors.

Such DNA fragments can be prepared since the information disclosed in FIG. 1 and Sequence ID Nos. 1–64 is available. That is, for example, a DNA fragment containing not less than two functional $V_H$ segments can be obtained by partially digesting human genome with an appropriate restriction enzyme such as Eco RI or Hind III, separating the resulting fragments by electrophoresis, and selecting a DNA fragment containing not less than two desired functional $V_H$ segments using not less than two probes each of which hybridizes with one of the not less than two desired functional $V_H$ segments. Alternatively, amplification by PCR may be employed in place of the detection by the probes. In this case, since the entire DNA sequences of the functional $V_H$ segments are known, the DNA sequences of the primers which should be used are also known, so that the PCR can be carried out easily.

The present invention further provides DNA fragments consisting essentially of optional DNA fragments each of which contains not less than two functional $V_H$ segments which are ligated in optional orders. That is, by ligating a plurality of the DNA fragments each containing not less than two functional $V_H$ segments, the number of $V_H$ segments in the DNA fragment can be increased when compared with the case where only one such DNA fragment containing not less than two $V_H$ segments is used, so that the diversity of the produced immunoglobulin can be increased accordingly. The DNA fragments are not necessarily consecutive, and optional DNA fragments may be ligated in an optional order. In cases where there is no overlapping region between two DNA fragments to be ligated, the above-described method for ligating the DNA fragments having an overlapping region cannot be applied. However, two DNA fragments having no overlapping region can also be ligated by the method as follows.

The left arm vector region and the right arm vector region of a YAC clone containing not less than two functional $V_H$ segments are recovered by the method of Hermanson et al (1991) (Nucleic Acids. Res.,19; 4943–4948). A plasmid (pICL) which has a sequence homologous with the ampicillin-resistant marker (AMP) in the left arm vector region of the YAC, a marker (Lys) which reverse the lysine auxotrophy to the wild type, and a multiple cloning site immediately downstream Lys; and a plasmid (pLUS) which has a sequence homologous with YAC4 region in the right arm vector region of the YAC, the above-mentioned Lys, a kanamycin-resistant marker (KAN), and a multiple cloning site immediately downstream the KIN are linearized and then introduced into yeast cells containing YAC by a conventional method. The plasmids pICL and pLUS cause recombination in the yeast cells at an appropriate frequency, thereby being recombined with the left arm vector region and the right arm vector region of the YAC. The yeast cells carrying such a YAC are selected by using an appropriate selection medium and the YAC in the selected yeast cells is then cut with an appropriate restriction enzyme which has a restriction sites in the multiple cloning sites of the above-mentioned plasmids. By the operation described above, DNA fragments containing the left end or the right end of the DNA fragment originated from human contained in the YAC are recovered as plasmids. After amplifying the thus obtained plasmids in *E. coli* by a conventional method, the recovered plasmids are digested with a restriction enzyme and then ligated by ligase. The thus ligated DNA fragment is then ligated to the left arm vector region or the right arm vector region of the YAC and introduced into yeast cells carrying the YAC. These YAC vectors causes recombination at a certain frequency between the intrinsic left arm or right arm vector regions and the left end or right end region of the DNA fragment originated from human. By selecting the resulting recombinant vectors, a YAC clone containing a DNA fragment originated from human, which left end is ligated to the right end of another DNA fragment originated from human, and a YAC clone containing a DNA fragment originated from human, which right end is ligated to the left end of another DNA fragment originated from human are recovered. Since these YAC clones have the structure in which the left end or the right end of a DNA originated from human is ligated to the right end or the left end of another DNA originated from human, they can be recombined with a YAC clone having a sequence in the ligated DNA fragments by the method described above.

Further, by optionally ligating the above-described eight actually deposited DNA fragments in an optional order, a large fragment containing a number of $V_H$ segments can be prepared.

By the present invention, the DNA sequences of the 64 $V_H$ segments contained in the fragment of about 800 kbp shown in FIG. 1 were determined. As described in detail in the examples below, among these, 50 $V_H$ segments are novel segments which have DNA sequences that have not hitherto been known. These novel human immunoglobulin $V_H$ segments include pseudo segments which do not encode a polypeptide. Even a pseudo segment has an utility because it may function as a donor of gene conversion in the somatic cell level.

The human immunoglobulin $V_H$ segments and the DNA fragments containing the same according to the present invention can be used for producing human immunoglobulins in a mammalian host as described in, for example, Japanese Laid-open PCT Application (Kohyo) No. 4-504365.

EXAMPLES

The present invention will now be described in more detail by way of examples thereof. It should be noted that the present invention is not limited to the following examples.

Example 1

Determination of Structure of DNA Fragment of about 800 kbp (1) Library Used for Screening The human YAC library screened was constructed from DNA of an Epstein-Barr virus-transformed human lymphoblastoid cell line CGM1 (T. Imai and M. V. Olson, genomics, 8, 297–303 (1990)). Eco RI partial digests of CGM1 DNA were ligated to pYAC4 vector (D. Burke and M. V. Olson, in "Guide to Yeast Genetics and Molecular Biology" (C. Guthrie and G. R. Fink, eds), p.253, Academic Press, Orlando, 1991), and introduced into AB1380 yeast host strain (D. Burke and H. V. Olson, in "Guide to Yeast Genetics and Molecular Biology" (C. Guthrie and G. R. Fink, eds), p.253, Academic Press, Orlando, 1991). The library consisted of 15,000 independent clones with mean YAC size of about 360 kb. The library thus contained the equivalent of approximately 1.8 haploid human genomes. DNA rearrangement in immunoglobulin H chain (IgH) locus was first checked by Southern hybridization using the human D and $J_H$ probes. The result showed that an allele kept germine configuration while the other was VDJ rearranged.

(2) Primers Used for PCR-based Screening

For PCR-based screening of human $V_H$ YAC clones, oligonucleotide primers for $V_{H-III}$ and $V_{H-I}$ families, the first and the second largest $V_H$ families, were synthesized. $V_H$ region segments of immunoglobulins contain two hypervariable regions (CDR1 and CDR2) and three framework regions (FR1, FR2 and FR3) (E.A. Tabat at al., Sequences of Proteins of Immunological Interest, Fifth edition, NIH publications, Washington D.C. (1991)). Nucleotide sequences of the framework regions are highly conserved within the same family, suggesting the possibility of oligonucleotide synthesis is for consensus primers corresponding to the framework regions. For this purpose, nucleotide sequences of PR1, FR2 and FR3 regions in all the known VU sequences were aligned for comparison. Nucleotide sequences corresponding to the first 8 amino acid residues of the FR1 region had extremely high conservation not only within the same family but also between $V_{H-I}$ and $V_{H-III}$ families; which enabled the synthesis of a forward primer F-univ common for the two families as shown in Table 1. Sequences for family-specific reverse primers were independently chosen from conserved sequences in the FR2 region so that 3'-half of the primer sequence has 100% identity to known $V_H$ segments and, in particular, 3'-most nucleotide corresponds to the first letter of the highly conserved/invariant amino acid residues. More particularly, F-univ and I-R, and F-univ and III-R were used as primers for the screening. The DNA sequences of the primers are shown in Table 1.

(3) Optimal PCR Condition Check

Analytical experiments were carried out to determine the optimal condition for specific amplification. A reaction mixture (5 $\mu$l) was prepared in accordance with the protocol recommended by Perkin-Elmer/Cetus. Thermal cycling was performed using a DNA Thermal Cycler (Perkin-Elmer/Cetus). Reactions were carried out using 25 ng of template human DNA under various annealing temperatures (55° C., 56° C., 60° C. and 62° C.) and cycles (25, 30, and 35 cycles). As a result, it was found that the reaction under high annealing temperature, namely 94° C., 1 minute—62° C., 2 minutes—72° C., 2 minutes, regardless of cycles, produced specific amplification in human DNA sample but not in yeast strain AB1380 DNA. PCR under low annealing temperature sometimes gave false positive signals in negative control and therefore could not be used. Thus, the PCR was carried out under the above-described conditions.

(4) Polymerase Chain Reaction (PCR)

PCR-based first screening was performed using synthesized oligonucleotide primers described above against seven multi-filter DNA pools each of which represents the DNA from 1920 colonies (20×96-well) as described (E. D. Green and M. V. Olson, Proc. Natl. Acad. Sci. USA, 87, 1213–1217 (1990)). Positive multi-filter pools were divided into five pools each of which consists of 384 colonies (4×96-well), and further screened by the same procedure. 25 ng each of YAC pool DNAs were used for reaction. DNA of CGM1 whose DNA was used to construct the YAC library, and of the yeast strain AB1380 were included during the PCR analysis as positive and negative controls, respectively. After the amplification, the entire sample was analyzed by electrophoresis in 10% polyacrylamide gels containing 15% glycerol and visualized by ethidium bromide staining.

(5) Colony Hybridization

After PCR-based first and second screening, the location of the positive clone within the 384-clone array was established by conventional colony hybridization. The nylon filters consisting of 384 YAC clones were prepared by a known method (D. Burke and M. V. Olson, in "Guide to Yeast Genetics and Molecular Biology" (C. Guthrie and G. R. Fink, eds), p.253, Academic Press, Orlando, 1991). V266BL (Y. Nishida, et al., Proc. Natl. Acad. Sci. USA, 79, 3833–3837 (1992)) and $V_{HMV}$ (M. Kodaira et al., J. Mol. Biol., 19D, 529–541(1986)) were used for probes representative for human $V_{H-I}$ and $V_{H-III}$ families, respectively. These probes were labeled (5×10$^5$ cpm) with $^{32}$P-dCTP using oligolabeling Kit (Pharmacia) and subjected to colony hybridization according to standard procedure (D. Burke, et al., supra). After the hybridization for 12 hours at 65° C., filters were washed twice with 2×SSC (1×SSC is 0.15 M NaCl-15 mM sodium citrate) for 10 minutes at room temperature, then twice with 0.2×SSC-0.1% SDS for 30 minutes at 65° C. Filters were exposed overnight and corresponding positive YAC clones were picked up for further characterization.

(6) Insert Check by Colony PCR

To test the presence of specific DNA sequence in isolated YACs, simple and rapid rescreening of colony-purified clones was carried out by using PCR without DNA purification (E. D. Green and X. V. Olson, Proc. Natl. Acad. Sci. USA, 87, 1213–1217 (1990)). That is, the positive yeast clones were streaked onto AHC plates and grown. Four each of single colonies from each clone were transferred by toothpick into 5 $\mu$l of PCR mixture described above. PCR and following gel electrophoresis were performed for identification of the amplified bands under the same condition as that used for screening. In most of the clones, all of the four colonies gave rise to specific amplification of DNA fragments.

(7) Sizing of YAC Clones Using PFGE

Figure 2:
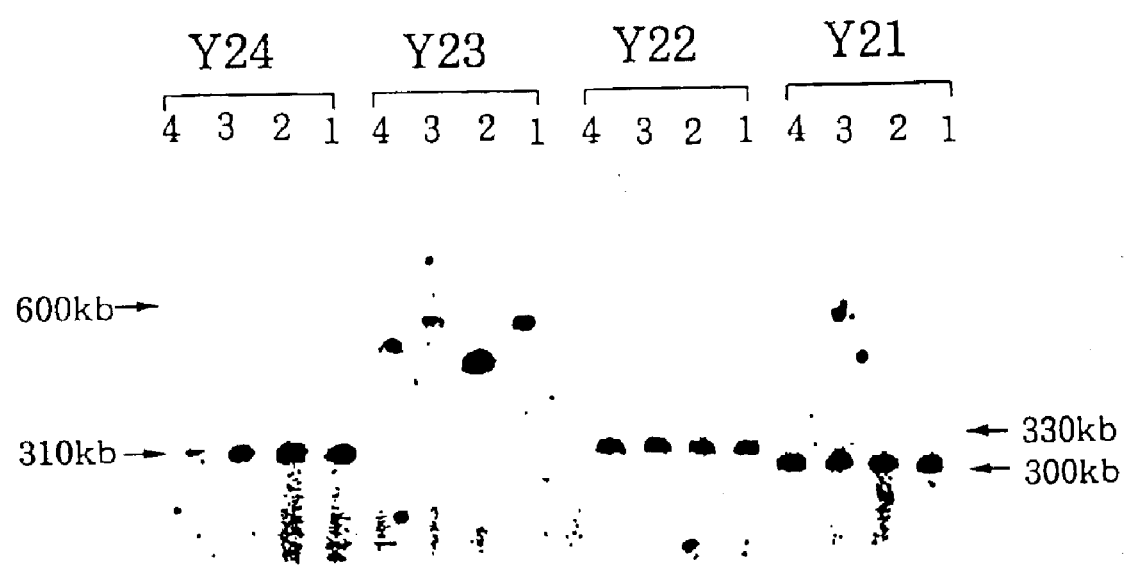
FIG. 2 shows the results of Southern hybridization of a representative DNA inserted in YAC.

Many researchers claimed that some YACs are clonally unstable due to intrachromosomal rearrangement during the growth in culture resulting in size variation of the human DNA insert. This artifact is considered to be often mediated by repetitive sequences or tandem repeat of homologous DNA sequences in the insert DNA. Since $V_H$ locus contains a number of homologous DNA fragments consisting of $V_H$ gene segments and their flanking regions, such kind of rearrangement can take place at considerable frequency. An additional problem is the presence of single yeast containing more than one insert YACs. In order to exclude the artifact clones for subsequent analysis and to identify YAC clones with multiple insert, the sizes of the YAC clones were first determined by pulse field gel electrophoresis (PFGE). The same four $V_H$-positive single colonies checked by PCR were selected from 17 colonies originating from a single well, and miniprepared from 5 ml culture in ARC medium to give low-gelling temperature agarose blocks by a known method (D. Burke et al., supra). Appropriate sized piece of agarose block was used for sizing the YACs by PFGE with a Pulsaphor (Pharmacia) ora Crossfield (ATTO, Tokyo, Japan) gel electrophoresis apparatus at 60 second pulse time. Concatamerized lambda DNA was also loaded as a size standard. After the electrophoresis, DNAs were transferred to nitrocellulose filter and subjected to Southern hybridization using pBR322 plasmid as a probe. Typical result is shown in FIG. 2. All of the four colonies selected from each of clones Y21, Y22 and Y24 having DNA inserts with a size of 300 kb, 330 kb and 310 kb, respectively exhibited the same size, so that they seemed to have no recombination. On the other hand, since four colonies selected from clone Y23 had DNA inserts with different sizes, the insert of the clone Y23 looked rather unstable due to frequent recombination. Therefore, the colony which did not cause recombination was selected for the subsequent analysis. All but 3 clones including clone Y23 of 17 $V_H$-carrying YAC clones including the analyzed $V_H$ displayed instability of human inserts. Subsequent analysis revealed that such recombination took place regardless of the number of $V_H$ segments in the insert DNA, indicating some other factors might be involved in homologous recombination. From 14 stable YAC clones among the 17 YAC clones containing $V_H$, Y20, Y103, Y21, Y6 and Y24 were selected and used for the subsequent physical mapping.

(8) Physical Mapping of YAC Clones with Rare Site Endonucleases

Gel blocks were prepared from the YAC clones after sizing and were used for physical map construction by PFGE. In general, detailed physical map using several enzymes might be required for long-range YAC analysis in this example, however, only two rare-site restriction enzymes (i.e., restriction enzymes whose restriction sites occur relatively rarely), namely Not I and Mlu I, were used for overlapping analysis of the YAC clones mainly by the following two reasons: 1) $V_H$-carrying YAC clones can be arrayed with several other information such as comparison of the size or the pattern of the fragments hybridized with $V_H$ probes or non-repetitive probes isolated from $V_H$-carrying cosmid clones, 2) it is necessary to subclone the YACs into cosmids for detailed structural analysis including construction of physical maps using ordinary restriction enzymes.

Gel blocks digested in completion with Not I or Mlu I were electrophoresed with a PPGE apparatus using a pulse time of 30 to 60 seconds depending on the length of YAC. Mixtures of lambda phage DNA, its Xho I digests and Hind III digests were also used as low molecular weight size markers. Southern filters were first hybridized with total human large molecular DNAs for detection of all restricted fragments. The sizes of detected bands were stummed up to fit the length of undigested YAC insert. Filters were hybridized consecutively with pBR322 DNA probes corresponding to each of the pYAC4 arms. A Pvu II and Bam HI double digest of pBR322 results in a 2.67-kb and 1.69-kb fragments which hybridize specifically to the left (trp) and the right (ura) end of YACs, respectively. Filters were also hybridized with six $V_H$ family-specific probes for the presence of $V_H$ segments in digested DNA fragments. Origin of $V_H$ family-specific probes for $V_{H-II}$, $V_{H-IV}$, $V_{H-V}$ and $V_{H-VI}$ families, respectively, are; $V_{CE-1}$ (N. Takahashi et al., Proc. Natl. Acad. Sci. USA, 81, 5194–5198 (1984)), $V_{71-2}$ (K. H. Lee et al., J. Mol. Biol., 195, 761–768 (1987)), 5-IRI (J. E. Bermanet al., EMBO J. 7, 727–1051 (1988) and 6-IRI (J. E. Berman et. al., EMBO J. 7, 727–1051 (1988)).

In order to array Mot I and Mlu I fragments detected by the complete digestion experiments, hybridization experiments using partially digested YAC DNA were carried out. Analytical experiment was necessary to determine the optimal condition for partial digestion since the efficiency of the restriction enzyme reaction is highly dependent on the purity of DNA. In the DNA preparation in this example, 6-hour incubation with 1 unit of restriction enzyme was, in most cases, sufficient for complete digestion of a gel block (about 500 ng of DNA). Partial cleavage of DNA was achieved by varying the time of digestion as follows:

1. Dialyze three gel blocks (about 50 µl each volume containing about 1 µg of DNA, stored in 0.5 M EDTA (pH 8.0)) for 1 hour against 50 ml of distilled water at room temperature with gentle agitation. Repeat this step for complete removal of EDTA.
2. Equilibrate the blocks with 10 ml appropriate digestion buffer at 37° C. for 30 minutes.
3. Transfer each block to 25-µl reaction mixture containing 1 unit each of restriction enzyme in 1× digestion buffer.
4. Incubate all three tubes for 10 minutes, 30 minutes and 1 hour at 37° C.
5. Stop the reaction by adding 100 µl of 0.5 M EDTA (pH 8.0).
6. Equilibrate the blocks with appropriate gel electrophoresis buffer 2–3 times over a 1 hour period and immediately perform PFGE using an appropriate pulse time.

Figure 3:
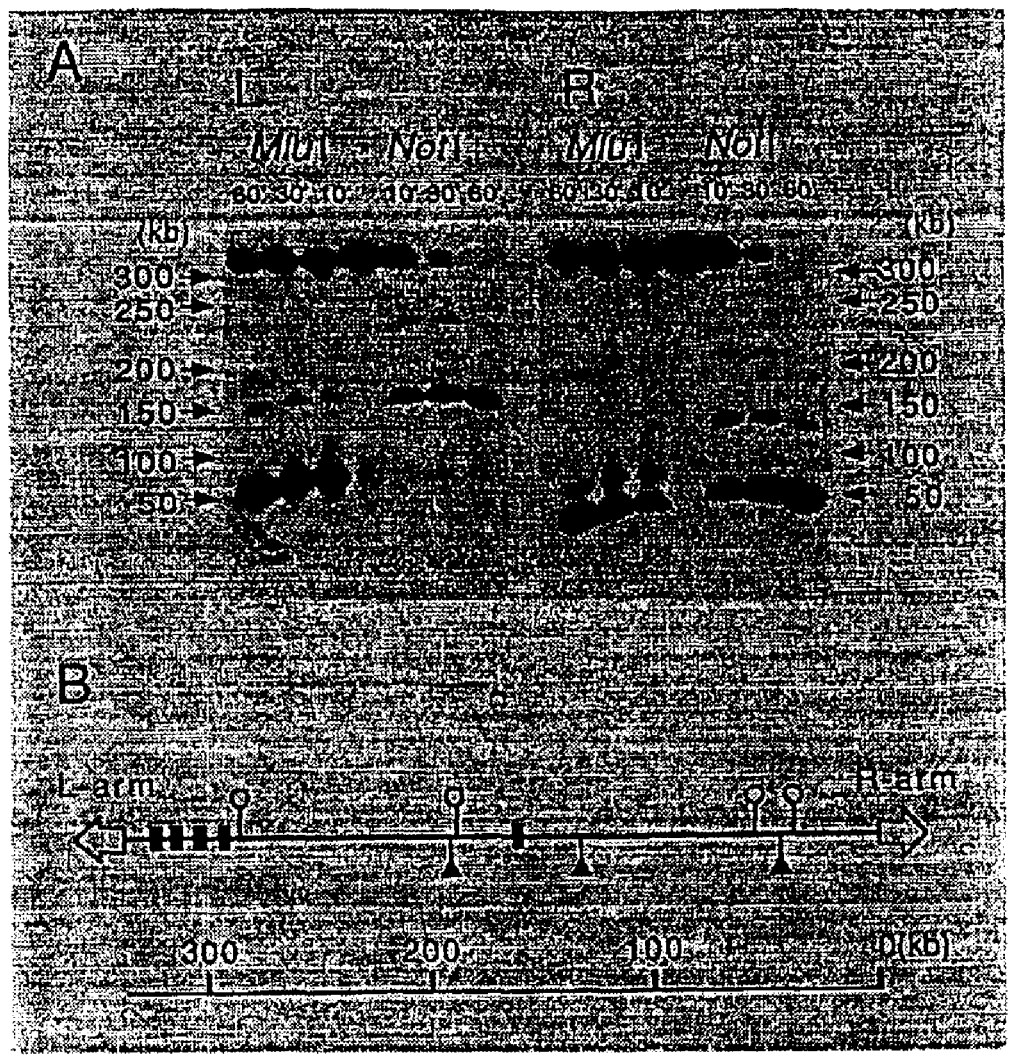
FIG. 3A shows the results of Southern hybridization of the fragment digested with restriction enzymes Mlu I and Not I.
FIG. 3B shows a physical map of a YAC clone constructed based on the results shown in FIG. 3A.

Filters were hybridized with the above-described right- or left-end probe of YAC vector and the size of the hybridized restriction fragments was determined by comparison with size standards (FIG. 3A). Results from complete and partial digestion experiments were combined to construct a physical map of YAC clones shown In FIG. 3B. Mapped clones were thus linked and classified into several contigs.

(9) Isolation of Insert-terminal Sequences from YACs

After isolated YAC clones were classified into several contigs based on their restriction maps, insert-terminal DNA segments were isolated from both ends of each contig to synthesize oligonucleotide primers. As is often pointed out, considerable percentage (up to 30%) of YAC clones in libraries contain noncontiguous DNA segments spliced together resulting in "chimeric clone". Since no good strategies have been developed to exclude coligation artifact during the construction of the library, it is necessary to check this possibility with appropriate method after isolation of YAC clones. In this example, the strategy to investigate the possibility by using PCR with synthesized insert-terminal primers was taken. The reason is that the synthesized primers would be useful not only to investigate chimeric clones but also to register resulting sequences as sequence tagged sites (STS) for rescreening the YAC library by PCR. In addition, they could be used to look for overlaps between contigs-which could not be found by comparison of their restriction maps.

For isolation of insert-terminal YAC segments, several different methods can be employed including more sophisticated and rapid method by inverse PCR and the Vectorette system (J. H. Riley et al., Nucleic Acids Res., 18, 2887–2890 (1990)). However, in this example, a rather classical way, that is, to subclone the fragments with plasmid or lambda phage vectors was taken. High molecular weight DNA from YAC clones was digested with restriction enzymes which have recognition sites both in right- and left-arm sequences. Gel electrophoresis was performed in a 0.7% agarose gel and Southern filter was hybridized with a 0.62-kb Hd III—Sal I fragment of pBR322 DNA ($Tet^R$) which specifically hybridizes with insert-vector boundary sequence of pYAC4 vector. The DNA fractions of interest were recovered from the gel using DE81 paper and ligated to either EMEL4 or pUC19 vector depending on the insert size. Isolated fragments with EMBL4 vector were subcloned into pUC19 vector for subsequent sequencing. The chain termination method with M13 forward or reverse primer was used for sequencing these plasmid clones. Sequences for insert-terminal primers were provided from the non-repetitive portion in the resulting sequence.

PCR experiments were achieved to investigate the above-mentioned artifact using primers at the both ends of YAC-DRA against the DNA from a human mouse somatic cell hybrid GM10479 line (Colier Institute) which carries human chromosome 14 alone in which the human IgH locus exists. DNA from CGM1 cells (source of YAC library) and Rag cells (mouse cell) were also used as positive and negative controls, respectively. PCR was carried out in 25-$\mu$l reactions according to a known method (H. S. Kim and O. Smithies, Nucleic Acids Res., 16, 8870–8903 (1988)). 200 ng each of DNA was used for the reaction. Incubations containing DNAs from GM10479, CGM1 and Rag, respectively were subjected to 35 to 40 cycles at 95° C., 1 minute—55 to 62° C., 2 minutes 72° C., 2 minutes according to the condition optimized by analytical experiment using CGM1 DNA. The YAC clones of which either of the two insert-terminal primers gave no specific amplification against GM10479 were concluded to be chimeric clones. Only one contig neither of which primers gave amplified bands was turned out to cover orphan $V_H$ locus on chromosome 16.

(10) Cosmid Subcloning and Construction of Physical Maps

Isolation of large chromosomal region using YAC system is advantageous for the initial step of physical mapping. However, subsequent step to analyze large DNA fragments in YAC can be problematic since exogenous DNA inserts cannot be easily separated from yeast chromosomal DNA and fragments up to several hundred kb are difficult to handle without mechanical shearing. In order to map $V_H$ segments of a large DNA fragment containing $V_H$ segments, detailed restriction map using common 6bp-site restriction enzyme is necessary. For this purpose, YAC clones were subcloned into cosmids. Cosmid libraries were constructed from whole YAC DNA without previous separation of cloned DNA from host chromosome. There are two major reasons for thist: 1) separation of intact insert DNA and their manipulation are difficult, 2) 4000 independent colonies are sufficient for complete coverage of YAC insert since the genome size of yeast is about $1.5 \times 10^4$ bp, 1/200 of that of human.

In general, there are two major difficulties in the construction of cosmid libraries. The first is self-ligation of vector DNAS, resulting in generation of clones carrying no inserts of foreign DNA, and the second is insertion of more than one DNA fragments in a single vector, namely co-ligation artifact. To overcome these problems, great efforts have been made including construction of better-designed vectors with two cos sites and modified method for ligation such as partial filling of vector and insert DNAs (J. Sambrook et al., A Laboratory Manual, Cold Spring Harbor Laboratory Press, Cold Spring Harbor, N.Y. (1989)). Size fractionated insert DNA usually contains smaller DNA molecules trapped among larger molecules especially when excess amount of DNA was loaded in the preparative gel. Alkaline phosphatase treatment of insert DNA is effective in order to exclude the co-ligation between inserts but gives rise to polymerized vector DNA during the ligation step, which causes high background of empty colonies under the antibiotic selection. In this example, however, less than 5 $\mu$g of YAC DNA was sufficient for insert preparation and thus preparative gel electrophoresis was successful without contamination of smaller DNA fragments. Most of the cosmid libraries were thus constructed with minimal steps in combination with alkaline phosphatase-treated cosmid vector and partially digested DNA of exact size range for cosmid insert (from 35 kb to 45 kb).

① Preparation of Yeast DNA Containing YAC

Since large DNA fragments are required as starting material for preparing the DNA, extraction of DNA from yeast cells with minimal shear damage is one of the most critical steps. Obviously, the best way is to manipulate DNA in-gel because DNA is fully protected from shear damage. The present inventors found, however, that gentle extraction of DNA in liquid from yeast cells gives sufficient length of. DNA (>200 kb) for partial digestion and subsequent size fractionation. In addition, liquid DNA is easier to control the condition for partial digestion than gel block DNA. With a simple and rapid (6 hours for total procedure) method described below, about 50 $\mu$g of large size DNA (>200 kb) can be routinely purified from 100-ml yeast culture.

(i) Spin down yeast calls and wash them with TE (10 mM, Tris HCl (pH 8.0)—1 mM EDTA) twice.

(ii) Resuspend the cells in 20 ml of 0.1 M EDTA (pH 7.5), 1 M sorbitol, 0.2 mg/ml of Zymolyase 100T (ICN Cat#152270), 15 mm 2-mercaptoethanol. Incubate at 37° C. for 1 hour to form spheroplasts.

(iii) Spin down the spheroplasts and resuspend in 9 ml of 0.1 M Tris HCl (pH 7.5), 50 mM EDTA (pH 7.5).

(iv) Add 1 ml (1/10 final volume) of 108 SDS and mix gently. Incubate at 60° C. for 10 to 20 minutes.

(v) Add 1/3 volume of 4 M potassium acetate and mix gently. Leave on ice for 30 minutes.

(vi) Centrifuge at 2000×g for 30 minutes and transfer the supernatant to a new tube. Add 3 volumes of isopropanol and mix gently. Leave at room temperature for 10 to 20 minutes for precipitation of DNA.

(vii) Centrifuge again at 2000×g for 30 minutes and discard supernatant. Dissolve the pellet in 10 ml of water.

From this step onwards, care should be taken not to give shear damage to the DNA.

(viii) Extract with phenol twice and with CIAA (chloroform:isoamyl alcohol=24:1) twice followed by ethanol precipitation at room temperature for 10 to 20 minutes.

(ix) Centrifuge at 2000×g for 30 minutes. Rinae the pellet with 70% ethanol and dry up the pellet.

(x) Dissolve with 1 ml of TE.

② Vector DNA Preparation

Lorist 2 DNA was linearized by digestion with Hind III or Bam HI. Linearized DNA was dephosphorylated by treatment with bacterial alkaline phosphatase. Small aliquots of DNA before and after phosphatase treatment were used for test ligation for phouphatase treatment according to a known method (J. Sambrook et al., supra).

③ Insert DNA Preparation

Analytical experiment of partial digestion of yeast DNA was performed according to standard procedure (J. Sambrook et al., supra) to determine the optimal enzyme concentration and reaction time. Preparation of size-fractionated DNA from the gel was achieved with LGT agarose and a agarase r. This very gentle method resulted in high recovery (>90%) of fractionated DNA without degradation. Scaled up cleavage reaction was done using 5 $\mu$g of DNA with optimal enzyme concentration. Digested samples were loaded in a preparative gel of 0.5% LGT agarose (Bio Rad preparative grade) at about 1 V/cm overnight. Linearized lambda DNA and its Xho I-digests which give 35-kb and 15-kb bands were also loaded as size markers. After visualizing the DNA under ultraviolet transilluminater, a small slice of agarose containing the fraction ranging from 35 kb to 45 kb was cut out. Recovery of the DNA from the gel slice was achieved using p agarase I (NEB) as follows:

(i) Equilibrate the gel block with water for complete removal of gel electrophoresis buffer.

(ii) Transfer the block to a new tube and add ⅑ volume of 10× β agarase I buffer.
(iii) Melt the gel at 68° C. for 10 minutes. Cool to 40° C. and incubate the molten agarose at 40° C. for 1 hour with optimal number of units of β agarase I.
(iv) Adjust the salt concentration of the solution to 0.5 M NaCl for ethanol precipitation. Chill on ice for 10 minutes.
3 (v) Centrifuge at 15,000×g for 15 minutes to pellet any remaining undigested carbohydrates.
(vi) Transfer the DNA-containing supernatant to a new tube. Precipitate the DNA with 3 volumes of ethanol at −80° C. for 10 minutes.
(vii) Centrifuge at 15,000×g for 15 minutes and remove the supernatant. Rinse the pellet with 70% ethanol and dry up the pellet.
(viii) Resuspend the pellet in appropriate volume of water for subsequent manipulation.
With this method, in average 100 to 300 ng of size-fractionated DNA can be recovered.

④ Ligation, in vitro Packaging and Infection to E. coli

This process was performed according to standard procedure (J. Sambrook et al., supra). By using lambda inn packaging kit (Nippon Gene) and ED8768 host strain, about 10,000 colonies were obtained from 25 ng of ligated DNA.

⑤ Screening of Commid Libraries

Initial screening was carried out using Lind III-partial cosmid libraries. About 10,000 colonies (500 colonies per φ10 cm plate×20) were plated on LB plates containing 50 μg/ml of kanamycin so that single colonies can be picked up after first screening. Colonies were then lifted from the plates with φ8.2 cm detergent-free nitrocellulose membranes (Advantec Toyo Membrane) and subjected to colony hybridization. Three different kinds of probes were used for screening, nasely mixture of six $V_H$-family specific probes to isolate $V_H$-containing cosmid clones, YAC vector probes (Tet$^R$ gene segment of pBR322, described above) for isolation of insert-terminal cosmid clones, and total human DNA for any remaining cosmid clones. In average, 50 to 100 clones from a YAC clone with approximately 300-kb insert were isolated with the probes.

⑥ Construction of Cosmid Contigs

DNA from cosmid clones was isolated by the alkaline lysis method by a conventional method (J. Sambrook et al., supra). Purified cosmid DNAs were digested with Eco RI or Hind III and subjected to agarose gel electrophoresis for restriction mapping. Overlaps between clones were easily found by comparing restriction patterns among cosmid clones. Ordered cosmid clones were then cleaved with Eco RI or Hd III and loaded in a 0.7% agarose gel. Southern filter were hybridized with six $V_H$-family specific probes for identification of location and number of $V_H$ segments in cosmid clones. Filters were washed three times for 30 minutes under standard conditions (at 50° C. in 1×SSC, 0.1% SDS) followed by stringent conditions (at 65° C. in 0.1×SSC, 0.1% SDS). Location of $V_H$ segments were determined by comparison between hybridization pattern of cosmids and their physical maps.

Figure 4:
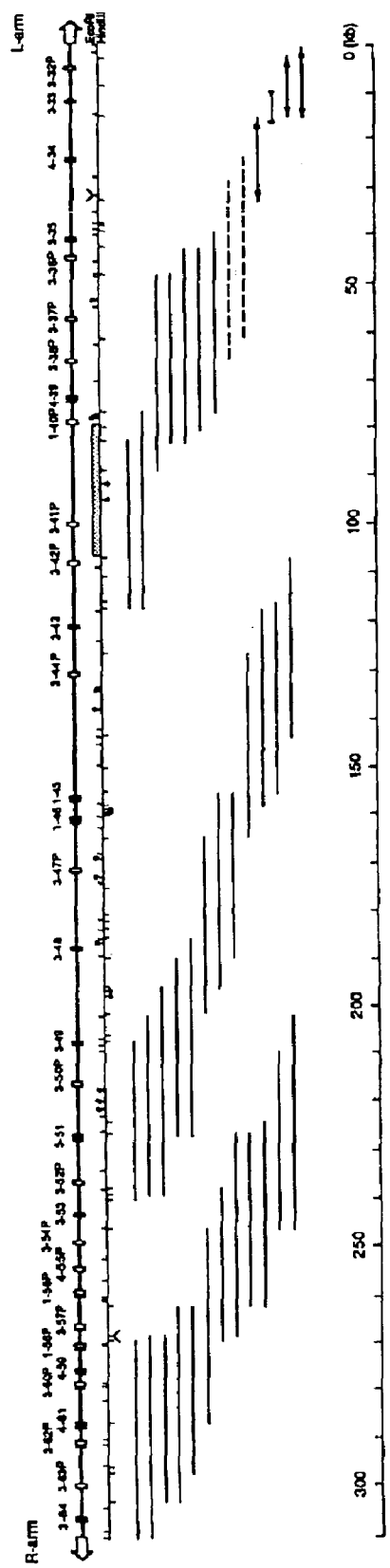
FIG. 4 shows a genetic map of YAC clone Y6.

Theoretically, approximately 50 independent cosmid clones (about 7 fold of the whole YAC insert) would be sufficient to cover the whole YAC insert of 300 kb in length. However, the distribution of cosmid clones were uneven and there still remained a few gaps. The clones corresponding to the gaps could not be isolated even after screening of Sau 3AI partial library or chromosomal walking by using the probes isolated from the edge of each contig. Regions not present in the cosmid libraries were subcloned with phage or plasmid vectors by isolation of DNA fragments of required size from YAC DNA as shown in FIG. 4. After the complete physical map was constructed, the present inventors found out that this was not due to the nonrandom distribution of restriction sites within the YAC insert. The presence of some classes of sequences such as palindromic or tandem repeat DNA might make these regions unclonable or under-represented by using cosmid system. The complete physical map of the 0.8-Mb region constructed in this example is shown in FIG. 1 as mentioned above. The distance from $J_H$ of each $V_H$ segment shown in FIG. 1 and the sizes of Eco RI and Hind III fragments are shown in Table 3.

Example 2

Construction of Cosmid Clones

A cosmid library was constructed from human high molecular DNAs as follows:

3-31: High molecular DNAs obtained from human placenta were partially digested with Taq I and the resultant was subjected to electrophoresis on 0.5% agarose gel. The 35–45-kb bands were recovered by using DEAE paper. The recovered DNAs were treated with alkaline phosphatase and the resultant was ligated to cosmid vector pJBB which had been completely digested with a restriction enzyme Cla I. The ligation product was subjected to in vitro packaging and the resultant was infected to host E. coli 490A, followed by the screening by the conventional colony hybridization to obtain the clone.

M131, M84 and M118: These fragments were obtained by the same method as for 3-31 except that the DNA used was human pro 8 cell line FLEB14-14, the vector and the host E. coli used were Lorist 2 and ED8767, respectively, the combination of restriction enzymes employed was Xba I and Hind III, and the edges of the fragments were modified by the partial repairing. The partial repairing was carried out according to a known method (J. Sambrook, E. F. Fritsch and T. Xaniatis, 1989, Molecular cloning; a Laboratory Manual, Cold Spring Harbor Laboratory Press, Cold Spring Harbor, N.Y.).

Example 3

Sequencing Analysis of $V_H$ Segments

Instead of sequencing subcloned $V_H$-containing DNA fragments using vector primers, $V_H$ family-specific oligonucleotide primers were synthesized. As mentioned above, nucleotide sequences of FR regions of $V_H$ segments are highly conserved within the same family, so the present inventors selected consensus sequences from the conserved portions and synthesized family-specific oligonucleotide primers for sequence analysis. For this purpose, automated fluorescence-based sequencing system Model 373A developed by Applied Biosystems was employed. Dye-Deoxy terminator sequencing kit supplied from the same company using fluorescent-dye labeled dideoxy nucleotides was suitable for our purpose'since synthesized $V_H$-specific primers could be directly used without fluorescence-label.

(1) Subcloning of $V_H$-containing Restriction Fragments

In order to use $V_H$-family specific primers for sequencing, it is essential to subclone $V_H$-containing DNA fragments so that each plasmid contains only one $V_H$ segment. Several other 6 bp-site enzymes than Eco RI and Hind III were used to isolate single $V_H$-carrying DNA fragments. Plasmid DNA of the subcloned fragments wan isolated by alkaline lysis method followed by ultracentrifugation twice to obtain high quality DNA samples for accurate sequences.

(2) Oligonucleotide Synthesis for Sequencing

To select consensus sequences for $V_H$ family-specific oligonucleotide primer synthesis, nucleotide sequences of framework regions and exon-intron boundaries of the known $V_H$ segments were aligned by family. Attention was paid so that 3'-half of them have 100% identities to reference sequences and 3'-most nucleotide corresponds to the first or the second letter of highly conserved/invariant amino acid residues. Nineteen additional primers were designed for five $V_H$ families as shown in Table 1 (described below).

(3) Sequencing Reaction and Gel Electrophoresis

The sequencing reaction was performed by PCR using Dye-Deoxy terminator sequencing kit (ABI) according to manufacturer's instruction. Gel electrophoresis and detection of signals were done in the sequencing apparatus according to the users manual of the system. In average, sequences of over 350 bases were obtained from each reaction.

(4) Evaluation of Synthesized $V_H$ Family-specific Primers

The primers F-univ and I-R were first chosen to sequence $V_{H-I}$ segments. An shown in Table 2, they annealed 11 of 12 $V_{H-I}$ segments analyzed. It is to be noted that all of 6 functional $V_{H-I}$ segments could be sequenced with these two primers. Two more primers, I-NF1 and I-NR1 were designed for V1-14P and V1-27P segments. These two primers were also used for some other $V_H$ segments to verify their sequences obtained by first two primers (Table 2).

Eight primers were designed and used for sequencing $V_{H-III}$ family segments. The first sequencing reaction of each $V_H$ segment was performed with F-univ and III-R primers. They annealed more-than 80% of the $V_{H-III}$ segments analyzed (25/30 for F-univ and 24/30 for III-R)(Table 2). Importantly, again, all the functional $V_{H-III}$ segments with one exception could be sequenced with this combination of primers, suggesting that they would be good for most of $V_{H-III}$ cDNA. Based on the nucleotide sequences obtained from first experiment, six additional primers (III-F3, III-R3, III-F4, III-R4, III-NF1 and III-F2) were designed and appropriate combination among them were used for further analysis. Among these, III-R3 and III-F4 were used to determine the sequence of 5' regulatory region and 3' flanking region, respectively. V3-29P and V3-32P were pseudogenes with extensive divergence in their sequences and thus all but III-NF1 failed to anneal these two $V_H$ segments. Sequences of V3-25P, V3-44P and V3-63P were determined using M13 vector primers from their internal restriction sites.

Five each of synthesized primers were used to determine the sequences of $V_H$ segments belonging to $V_{H-II}$, $V_{H-IV}$ and $V_{H-V}$ families. Since $V_H$ segments belonging to each of these three families are highly homologous with each other, it was thought that four each of the primers are enough for most of the $V_H$ segments belonging to these smaller $V_H$ families. In fact, all four $V_{H-II}$ family-specific primers annealed three $V_{H-II}$ segments (V2-5, V2-10P and V2-26). In brief, in total 11 primers (F-univ and I-R for $V_{H-I}$; II-R1, Ir-F2 and II-R2 for $V_{H-II}$; F-univ and III-R for $V_{H-III}$; IV-R1, IV-F2 and IV-R2 for $V_{H-IV}$; V-R2 and V-R3 for $V_{H-V}$) would be sufficient for sequencing most of the $V_H$ segments belonging to five $V_H$ families. The I-F1, III-NF2 and IV-F1 primers contain intron sequences and thus cannot be used for cDNA sequencing.

By this procedure, the DNA sequences of the 64 $V_H$ segments were determined and they are shown in Sequence ID Noe. 1–64 as mentioned above. The distance of each $V_H$ segment from $J_H$ and the sizes of Eco RI and Hind III fragments are summarized in Table 3.

(5) Transcriptional Polarities of $V_H$ Segments

The strategy for sequencing $V_H$ segments with family-specific primers was not suitable for determination of transcriptional polarities of the $V_H$ segments because it did not require restriction map of single $V_H$-containing subcloned fragments. The present inventors could not determine orientations of all the $V_H$ segments within this region for that reason. The present inventors found, however, that 8 regions containing 21 $V_H$ segments were already isolated in cosmid or phage clones since sequences between corresponding $V_H$ segments as well as their restriction maps were identical with each other. As the relative orders of these 21 $V_H$ segments within these clones are identical to those in the 0.8-mb region, it was concluded that the orientation of these 21 $V_H$ segments are the same as those of the $J_H$ segments.

TABLE 1

VH family-specific primers used for screening and sequencing

| FAMILY | NAME | SEQUENCE (5' to 3') | *LOCATION | DIRECTION | SEQ ID NOS |
|---|---|---|---|---|---|
| I, III, V | F — univ | AGGTGCAGCTGGTGCAGTCTG | 1–8 | forward | 65 |
| I | I — R | CCAGGGGCCTGTCGCACCCA | 36–42 | reverse | 66 |
| | I — N F 1 | TGGGGCCTCAGTGAAGGTCTCCTG | 14–22 | forward | 67 |
| | I — N R 1 | GATCC(A/G)TCCCATCCACTCAAG | 45–51 | reverse | 68/69 |
| II | II — F 1 | TGTCTTCTCCACAGGGGTCTT | intron–(−2) | forward | 70 |
| | II — F 2 | GGGAAGGCCCTGGAGTGGCT | 42–48 | forward | 71 |
| | II — R 1 | GTGCAGGTCAGCGTGAGGGT | 17–23 | reverse | 72 |
| | II — R 2 | TGGTTTTTGGAGGTGTCCTTGG | 70–77 | reverse | 73 |
| III | III — R | CACTCCAGCCCCTTCCCTGGAGC | 40–47 | reverse | 74 |
| | III — F 3 | GTGAGGTTCAGCTGGTGGAGT | (−I)–7 | forward | 75 |
| | III — R 3 | AGCTGAACCTCACACTGGAC | (−3)–4 | reverse | 76 |
| | III — F 4 | AAGGGCCGATTCACCATCT | 64–70 | Forward | 77 |
| | III — R 4 | TTGTCTCTGGAGATGGTGAA | 68–73 | reverse | 78 |
| | III — N F 1 | TGAGACTCTCCTGTGCAGCCTCTG | 18–26 | forward | 79 |
| | III — N F 2 | TCT(T/C)TGTGTTTGCAGGTGT | intron–(−3) | forward | 80/81 |
| IV | IV — F 1 | TCTGTTCACAGGGGTCCTGTC | intron–(−I) | forward | 82 |
| | IV — F 2 | TCCGGCAGCCCCCAGGGAA | 37–43 | forward | 83 |
| | IV — R 1 | GCAGGTGAGGGACAGGGT | 17–22 | reverse | 84 |
| | IV — R 2 | CAGGGAGAACTGGTTCTTGGA | 74–80 | reverse | 85 |
| V | V — R 1 | CCCGGGCATCTGGCGCACCCA | 36–42 | reverse | 86 |
| | V — R 2 | GCTGCTCCACTGCAGGTAGGC | 78–82R | reverse | 87 |
| | V — R 3 | CTTCAGGCTGCTCCACTGCAG | 74–83 | reverse | 88 |

*Locations of the primers are indicated as amino acid residue number according to Kabat et al. Bases with redundancy are shown in the parentheses. Directions relative to coding sequence are also shown.

TABLE 2

List of useful primers for sequencing $V_H$ clones

| | | $V_{H-I}$ primers | | | | $V_{H-III}$ primers | | | | | | | | $V_{H-IV}$ primers | | | |
|---|---|---|---|---|---|---|---|---|---|---|---|---|---|---|---|---|---|
| $V_H$ segments | | univ | R | NF1 | NR1 | univ | R | F3 | R3 | F4 | R4 | NF1 | NF2 | F1 | R1 | F2 | R2 |
| $V_H$I | 1-2 | + | + | | | | | | | | | | | | | | |
| | 1-3 | + | + | | | | | | | | | | | | | | |
| | 1-8 | + | + | | | | | | | | | | | | | | |
| | 1-12P | + | + | | | | | | | | | | | | | | |
| | 1-14P | − | + | + | | | | | | | | | | | | | |
| | 1-17P | + | + | + | + | | | | | | | | | | | | |
| | 1-18 | + | + | + | | | | | | | | | | | | | |
| | 1-24P | + | + | + | + | | | | | | | | | | | | |
| | 1-27P | + | − | + | + | | | | | | | | | | | | |
| | 1-40P | + | + | | | | | | | | | | | | | | |
| | 1-45 | + | + | | | | | | | | | | | | | | |
| | 1-46 | + | + | | | | | | | | | | | | | | |
| $V_H$III | 3-6P | | | | | − | + | − | + | − | + | + | + | | | | |
| | 3-7 | | | | | + | + | | + | + | | | | | | | |
| | 3-9 | | | | | + | + | | + | | | | | | | | |
| | 3-11 | | | | | + | + | | | | | + | + | | | | |
| | 3-13 | | | | | + | − | + | + | + | + | | | | | | |
| | 3-15 | | | | | + | + | | + | + | | | | | | | |
| | 3-16P | | | | | + | + | | + | | + | | | | | | |
| | 3-19P | | | | | + | + | | | | + | | | | | | |
| | 3-20 | | | | | + | + | | + | + | + | | | | | | |
| | 3-21 | | | | | + | | + | + | | | + | | | | | |
| | 3-22P | | | | | + | + | | + | | | | | | | | |
| | 3-23 | | | | | + | + | | + | + | + | | | | | | |
| | 3-29P | | | | | − | − | − | − | − | − | + | − | | | | |
| | 3-30 | | | | | + | + | | + | + | + | | | | | | |
| | 3-32P | | | | | − | − | − | − | − | − | + | − | | | | |
| | 3-33 | | | | | + | + | | | + | + | + | | | | | |
| | 3-35 | | | | | + | + | | | | | | | | | | |
| | 3-36P | | | | | − | + | + | | | | | | | | | |
| | 3-37P | | | | | + | − | | | | + | | | | | | |
| | 3-38P | | | | | + | + | | | | | | | | | | |
| | 3-41P | | | | | + | + | | | | | | | | | | |
| | 3-42P | | | | | + | − | | + | | + | | | | | | |
| | 3-43 | | | | | + | + | | | | | | | | | | |
| | 3-47P | | | | | + | + | | | | | | | | | | |
| | 3-48 | | | | | + | + | | | | | | | | | | |
| | 3-49 | | | | | + | + | | | | | | | | | | |
| | 3-50P | | | | | − | + | | | | | + | | | | | |
| | 3-52P | | | | | + | + | | | | | | | | | | |
| | 3-53 | | | | | + | + | | | | | | | | | | |
| | 3-54P | | | | | + | + | | | + | | | | | | | |
| | 3-64 | | | | | + | + | | | | | | | | | | |
| $V_H$IV | 4-4 | | | | | | | | | | | | | + | + | + | + |
| | 4-31 | | | | | | | | | | | | | + | + | − | + |
| | 4-34 | | | | | | | | | | | | | + | + | + | + |
| | 4-39 | | | | | | | | | | | | | + | + | | |
| | 4-55P | | | | | | | | | | | | | + | + | | |

TABLE 3

| $V_H$ | kb from $J_H$ | Fragment size (kb) EcoRI | Fragment size (kb) Hind III | $V_H$ | kb from $J_H$ | Fragment size (kb) EcoRI | Fragment size (kb) Hind III |
|---|---|---|---|---|---|---|---|
| 6-1 | 75 | 0.9 | 25 | 3-15 | 280 | 4.8 | 13.0 |
| 1-2 | 125 | 7.2 | 12.5 | 3-16P | 290 | 5.4 | 1.8 |
| 1-3 | 150 | 3.4 | 1.7 | 1-17P | 295 | 5.4 + 1.6 | 10.2 |
| 4-4 | 160 | 5.1 | 8.0 | 1-18 | 315 | 3.4 | 8.8 |
| 2-5 | 175 | 5.4 | 16.0 | 3-19P | 330 | 4.3 | 14.7 |
| 3-6P | 185 | 11.8 | 16.0 | 3-20 | 345 | 11.8 | 12.8 |
| 3-7 | 190 | 2.2 | 5.0 | 3-21 | 360 | 2.2 | 6.8 |
| 1-8 | 215 | 3.8 | 2.0 | 3-22P | 385 | 5.7 | 7.0 |
| 3-9 | 230 | 2.6 | 5.4 | 3-23 | 395 | 2.0 | 5.7 |
| 2-10P | 235 | 13.5 | 18.5 | 1-24P | 410 | 3.0 | 5.2 |
| 3-11 | 245 | 1.6 | 18.5 | 3-25P | 420 | 10.0 | 7.3 |
| 1-12P | 250 | 4.5 | 2.8 | 2-26 | 430 | 8.1 | 6.6 |
| 3-13 | 260 | 1.7 | 5.8 | 1-27P | 450 | 8.3 | 11.3 |
| 1-14P | 275 | 2.9 | 13.0 | 4-28 | 455 | 8.3 | 5.4 |

TABLE 3-continued

| V_H | kb from J_H | Fragment size (kb) EcoRI | Hind III |
|---|---|---|---|
| 3-29P | 460 | 3.5 | 5.8 |
| 3-30 | 470 | 9.8 | 6.8 |
| 4-31 | 475 | 10.3 | 13.0 |
| 3-32P | 485 | 13.3 | 5.6 |
| 3-33 | 490 | 13.3 | 6.8 |
| 4-34 | 505 | 11.5 | 16.2 |
| 3-35 | 520 | 5.3 | 3.2 |
| 3-36P | 525 | 5.3 | 5.7 |
| 3-37P | 540 | 7.5 | 13.2 |
| 3-38P | 545 | 8.0 | 15.4 |
| 4-39 | 555 | 7.0 | 15.4 |
| 1-40P | 560 | 1.4 | 3.2 |
| 3-41P | 580 | 4.4 | 11.9 |
| 3-42P | 590 | 3.0 | 3.8 |
| 3-43 | 600 | 6.5 | 8.1 |
| 3-44P | 610 | 8.8 | 17.0 |
| 1-45 | 635 | 10.7 | 2.7 |
| 1-46 | 640 | 2.0 | 4.6 |
| 3-47P | 650 | 2.7 | 10.5 |
| 3-48 | 670 | 2.7 | 3.9 |
| 3-49 | 690 | 1.6 | 16.5 |
| 3-50P | 695 | 10.0 | 16.5 |
| 5-51 | 710 | 8.0 | 11.0 |
| 3-52P | 715 | 4.0 | 11.0 |
| 3-53 | 725 | 8.3 | 6.3 |
| 3-54P | 730 | 6.4 | 15.4 |
| 4-55P | 735 | 3.9 | 15.4 |
| 1-56P | 740 | 3.4 | 15.4 |
| 3-57P | 745 | 9.7 | 6.6 |
| 1-58P | 750 | 8.3 | 17.5 |
| 4-59 | 755 | 8.3 | 17.5 |
| 3-60P | 760 | 0.8 + 3.0 | 17.5 |
| 4-61 | 770 | 8.1 | 9.0 |
| 3-62P | 775 | 4.6 | 9.0 |
| 3-63P | 780 | 8.9 | 6.2 |
| 3-64 | 790 | 4.4 | >7.4 |

What is claimed is:

1. An isolated polynucleotide consisting of a nucleic acid sequence, wherein said nucleic acid sequence is that of the insert of a clone selected from the group consisting of:
   (a) a yeast artificial chromosome clone that is isolable from a transformant identified by international deposit number FERM BP-4271;
   (b) a yeast artificial chromosome clone that is isolable from a transformant identified by international deposit number FERM BP-4274;
   (c) a yeast artificial chromosome clone that is isolable from a transformant identified by international deposit number FERM BP-4273;
   (d) a cosmid vector clone that is isolable from a transformant identified by international deposit number FERM BP-4278;
   (e) a cosmid vector clone that is isolable from a transformant identified by international deposit number FERM BP-4277;
   (f) a cosmid vector clone that is isolable from a transformant, identified by international deposit number FERM BP-4279; and
   (g) a cosmid vector clone that is isolable from a transformant identified by international deposit number FERM BP-4276.

2. The polynucleotide of claim 1, where in the clone is a yeast artificial chromosome clone that is isolable from a transformant identified by international deposit number FERM BP-4271.

3. The polynucleotide of claim 1, wherein the clone is a yeast artificial chromosome clone that is isolable from a transformant identified by international deposit number FERM BP-4273.

4. The polynucleotide of claim 1, wherein the clone is a cosmid vector clone that is isolable from a transformant identified by international deposit number FERM BP-4278.

5. The polynucleotide of claim 1, wherein the clone is a cosmid vector clone that is isolable from a transformant identified by international deposit number FERM BP-4277.

6. The polynucleotide of claim 1, wherein the clone is a cosmid vector clone that is isolable from a transformant identified by international deposit number FERM BP-4279.

7. The polynucleotide of claim 1, wherein the clone is a cosmid vector clone that is isolable from a transformant identified by international deposit number FERM BP-4276.

8. A yeast artificial chromosome comprising a nucleic acid sequence insert, wherein said nucleic acid sequence insert consists of a sequence that is that of the insert of a clone selected from the group consisting of:
   (a) a yeast artificial chromosome clone that is isolable from a transformant identified by international deposit number FERM BP-4271;
   (b) a yeast artificial chromosome clone that is isolable from a transformant identified by international deposit number FERM BP-4274; and
   (c) a yeast artificial chromosome clone that is isolable from a transformant identified by international deposit number FERM BP-4273.

9. The yeast artificial chromosome of claim 8, wherein the yeast artificial chromosome is a clone selected from the group consisting of:
   (a) a yeast artificial chromosome clone that is isolable from a transfonnant identified by international deposit number FERM BP-4271;
   (b) a yeast artificial chromosome clone that is isolable from a transformant identified by international deposit number FERM BP-4274; and
   (c) a yeast artificial chromosome clone that is isolable from a transformant identified by international deposit number FERM BP-4273.

10. A cosmid vector comprising a nucleic acid sequence insert, wherein said nucleic acid sequence insert consists of a sequence that is that of the insert of a clone selected from the group consisting of:
   (a) a cosmid vector clone that is isolable from a transfornant identified by international deposit number FERM BP-4278;
   (b) a cosmid vector clone that is isolable from a transformant identified by international deposit number FERM BP-4277;
   (c) a cosmid vector clone that is isolable from a transformant identified by international deposit number FERM BP-4279; and
   (d) a cosmid vector clone that is isolable from a transformant identified by international deposit number FERM BP-4276.

11. The cosmid vector of claim 10, wherein the cosmid vector is a clone selected from the group consisting of:
   (a) a cosmid vector clone that is isolable from a transformant identified by international deposit number FERM BP-4278;
   (b) a cosmid vector clone that is isolable from a transformant identified by international deposit number FERM BP-4277;
   (c) a cosmid vector clone that is isolable from a transformant identified by international deposit number FERM BP-4279; and
   (d) a cosmid vector clone that is isolable from a transformant identified by international deposit number FERM BP-4276.

12. An isolated cell transformed by a nucleic acid sequence, wherein said nucleic acid sequence is that of the insert of a clone selected from the group consisting of:
   (a) a yeast artificial chromosome clone that is isolable from a transformant identified by international deposit number FERM BP-4271;
   (b) a yeast artificial chromosome clone that is isolable from a transformant identified by international deposit number FERM BP-4274;
   (c) a yeast artificial chromosome clone that is isolable from a transformant identified by international deposit number FERM BP4273;
   (d) a cosmid vector clone that is isolable from a transformant identified by international deposit number FERM BP-4278;
   (e) a cosmid vector clone that is isolable from a transformant identified by international deposit number FERM BP-4277;
   (f) a cosmid vector clone that is isolable from a transfornant identified by international deposit number FERM BP-4279; and
   (g) a cosmid vector clone that is isolable from a transfonnant identified by international deposit number FERM BP-4276.

13. An isolated cell transformed by a clone selected from the group consisting of:
   (a) a yeast artificial chromosome clone that is isolable from a transformant identified by international deposit number FERM BP-4271;
   (b) a yeast artificial chromosome clone that is isolable from a transformant identified by international deposit number FERM BP-4274;
   (c) a yeast artificial chromosome clone that is isolable from a transformant identified by international deposit number FERM BP-4273;
   (d) a cosmid vector clone that is isolable from a transformant identified by international deposit number FERM BP4278;
   (e) a cosmid vector clone that is isolable from a transforinant identified by international deposit number FERM BP-4277;
   (f) a cosmid vector clone that is isolable from a transformant identified by international deposit number FERM BP-4279; and
   (g) a cosmid vector clone that is isolable from a transformant identified by international deposit number FERM BP-4276.

14. The isolated cell of claim 12 wherein the cell is a transformant selected from the group consisting of:
   (a) a transformant identified by international deposit number FERM BP-4271;
   (b) a transformant identified by international deposit number FERM BP-4273;
   (c) a transformant identified by international deposit number FERM BP4274;
   (d) a transformant identified by international deposit number FERM BP-4276;
   (e) a transformant identified by international deposit number FERM BP4277;
   (f) a transformant identified by international deposit number FERM BP-4278; and
   (g) a transformant identified by international deposit number FERM BP-4279.

* * * * *

UNITED STATES PATENT AND TRADEMARK OFFICE
CERTIFICATE OF CORRECTION

PATENT NO. : 6,936,705 B1
APPLICATION NO. : 09/515697
DATED : August 30, 2005
INVENTOR(S) : Tasuku Honjo and Fumihiko Matsuda It is certified that error appears in the above-identified patent and that said Letters Patent is hereby corrected as shown below:

On the title page, item [57]:

Abstract
Replace "immunoglobulln" with --immunoglobulin--.

Column 145
Line 48, replace "where in" with --wherein--.

Column 147
Line 42, replace "transfonnant" with --transformant--.

Column 148
Line 15, replace "BP4278" with --BP-4278--.
Line 33, replace "BP4274" with --BP-4274--.
Line 37, replace "BP4277" with --BP-4277--.

Signed and Sealed this

Twelfth Day of December, 2006

JON W. DUDAS
*Director of the United States Patent and Trademark Office*

Disclaimer 6,936,705—Tasuku Honjo, Kyoto (JP); Fumihiko Matsuda, Kyoto (JP). HUMAN IMMUNOGLOBULIN VH GENE SEGMENTS AND DNA FRAGMENTS CONTAINING THE SAME, Patent dated August 30, 2005. Disclaimer filed by the assignee Japan Tobacco Inc.

Hereby enter this disclaimer to claims 1-14 of said patent.

(*Official Gazette* February 22, 2011)

SEQUENCE LISTING (1) GENERAL INFORMATION:

(iii) NUMBER OF SEQUENCES: 145

(2) INFORMATION FOR SEQ ID NO: 1:

(i) SEQUENCE CHARACTERISTICS:
      (A) LENGTH: 1429 base pairs
      (B) TYPE: nucleic acid
      (C) STRANDEDNESS: double
      (D) TOPOLOGY: linear (ii) MOLECULE TYPE: Genomic DNA (vi) ORIGINAL SOURCE:
      (A) ORGANISM: Homo sapiens
      (G) CELL TYPE: human lymphoblast
      (H) CELL LINE: CGM1

(xi) SEQUENCE DESCRIPTION: SEQ ID NO: 1:

```
CTGATCTATG AATAAGGGTA TATAGACCAG TTTGGCCTGA TGTAGGGAAC GCCAAAGTGC      60

TGGAATTTCA GAGTCATCAC ACCCAGGGGC CCTGCCTCTG AGCTCCTCTT TGCATCCAAT     120

CTGCTGAAGA ACATGGCTCT AGGGAAACCC AGTTGTAGAC CTGAGGGCCC CGGCTCTTCA     180

ATGAGCCATC TCCGTCCCGG GGCCTTATAT CAGCAAGTGA CGCACACAGG CAAATGCCAG     240

GGTGTGGTTT CCTGTTTAAA TGTAGCCTCC CCCGCTGCAG AACTGCAGAG CCTGCTGAAT     300

TCTGGCTGAC CAGGGCAGTC ACCAGAGCTC CAGACAATGT CTGTCTCCTT CCTCATCTTC     360

CTGCCCGTGC TGGGCCTCCC ATGGGGTCAG TGTCAGGGAG ATGCCGTATT CACAGCAGCA     420

TTCACAGACT GAGGGGTGTT TCACTTTGCT GTTTCCTTTT GTCTCCAGGT GTCCTGTCAC     480

AGGTACAGCT GCAGCAGTCA GGTCCAGGAC TGGTGAAGCC CTCGCAGACC CTCTCACTCA     540

CCTGTGCCAT CTCCGGGGAC AGTGTCTCTA GCAACAGTGC TGCTTGGAAC TGGATCAGGC     600

AGTCCCCATC GAGAGGCCTT GAGTGGCTGG GAAGGACATA CTACAGGTCC AAGTGGTATA     660
```

```
ATGATTATGC AGTATCTGTG AAAAGTCGAA TAACCATCAA CCCAGACACA TCCAAGAACC      720

AGTTCTCCCT GCAGCTGAAC TCTGTGACTC CCGAGGACAC GGCTGTGTAT TACTGTGCAA      780

GAGACACAGT GAGGGAAGT CAGTGTGAGC CCAGACACAA ACCTCCCTGC AGGGATGCTC       840

AGGACCCCAG AAGGCACCCA GCACTACCAG CGCAGGGCCC AGACCAGGAG CAGGTGTGGA      900

GTTAAGCCAA AATGGAACTT CTTGCTGTGT CTTAAACTGT TGTTGTTTTT TTTTTTTTTT      960

TGGCTCAGCA ACAGAGATCA TAGAAAACCC TTTTTCATAT TTTTCAAATC TGTTCTTAGT     1020

CTAATGGAGA TTCTCTAATA TGTGACATTG TTTTTCTCTT GCTTGTTTTT GGAATTCTTT     1080

GTCTTTGACT TTTGACAACT TGACTTTTGA CAGTGTGCCT CAAAGAAGTT CTATTTTGGG     1140

TTCTGTGAAC CTCCTGGATC TGGGAAGTTT TCAGCTATGA TTTCATTAAA CGTGTTTTCT     1200

ACACCATTTC CCTACTTCTT TCCAATACCC ATAATGCAAA TATTTGTTCA CTTAATTGTG     1260

TCCCATAAAT GCCTGGGGAT TTTCTTCATT CCTTTTTACT CTTTTTTTCT TTTTATTCAT     1320

CTGCCTGAAT TATTTCAAAA GATCTGTCTT CAACTTCAGA AACTCTTTGG CTTGGCCTAG     1380

TCTAATCTTG AAGGTCTCAA TTGTACTTTT AATTTCATTC ATTGAATTC                 1429

(2) INFORMATION FOR SEQ ID NO: 2:

(i) SEQUENCE CHARACTERISTICS:
        (A) LENGTH: 512 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 2:

TGAGAGCTCC GTTCCTCACC ATGGACTGGA CCTGGAGGAT CCTCTTCTTG GTGGCAGCAG       60

CCACAGGTAA GAGGCTCCCT AGTCCCAGTG ATGAGAAAGA GATTGAGTCC AGTCCAGGGA      120

GATCTCATCC ACTTCTGTGT TCTCTCCACA GGAGCCCACT CCCAGGTGCA GCTGGTGCAG      180

TCTGGGGCTG AGGTGAAGAA GCCTGGGGCC TCAGTGAAGG TCTCCTGCAA GGCTTCTGGA      240

TACACCTTCA CCGGCTACTA TATGCACTGG GTGCGACAGG CCCCTGGACA AGGGCTTGAG      300

TGGATGGGAT GGATCAACCC TAACAGTGGT GGCACAAACT ATGCACAGAA GTTTCAGGGC      360

AGGGTCACCA TGACCAGGGA CACGTCCATC AGCACAGCCT ACATGGAGCT GAGCAGGCTG      420

AGATCTGACG ACACGGCCGT GTATTACTGT GCGAGAGACA CAGTGTGAAA ACCCACATCC      480

TGAGGGTGTC AGAAACCCAA GGGAGGAGGC AG                                   512

(2) INFORMATION FOR SEQ ID NO: 3:

(i) SEQUENCE CHARACTERISTICS:
        (A) LENGTH: 496 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1
```

(xi) SEQUENCE DESCRIPTION: SEQ ID NO: 3:

```
CACAACTCCT CACCATGGAC TGGACCTGGA GGATCCTCTT TTTGGTGGCA GCAGCCACAG    60

GTAAGGGGCT GCCAAATCCC AGTGAGGAGG AAGGGACTGA AGCCAGTCAA GGGGGCTTCC   120

ATCCACTCCT GTGTCTTCTC TACAGGTGTC CACTCCCAGG TTCAGCTGGT GCAGTCTGGG   180

GCTGAGGTGA AGAAGCCTGG GGCCTCAGTG AAGGTTTCCT GCAAGGCTTC TGGATACACC   240

TTCACTAGCT ATGCTATGCA TTGGGTGCGC CAGGCCCCCG GACAAAGGCT TGAGTGGATG   300

GGATGGAGCA ACGCTGGCAA TGGTAACACA AAATATTCAC AGGAGTTCCA GGGCAGAGTC   360

ACCATTACCA GGGACACATC CGCGAGCACA GCCTACATGG AGCTGAGCAG CCTGAGATCT   420

GAGGACATGG CTGTGTATTA CTGTGCGAGA GACACAGTGT GAAAACCCAC ATCCTGAGAG   480

TGTCAGAAAC CCCAGG                                                   496
```

(2) INFORMATION FOR SEQ ID NO: 4:

(i) SEQUENCE CHARACTERISTICS:
        (A) LENGTH: 650 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 4:

```
CACAGGAAAC CACCACACAT TTCCTTAAAT TCAGGGTCCA GCTCACATGG GAAATACTTT    60

CTGAGACTCA TGGACCTCCT GCACAAGAAC ATGAAACACC TGTGGTTCTT CCTCCTGCTG   120

GTGGCAGCTC CCAGATGTGA GTGTCTCAAG GCTGCAGACA TGGGATATGG GAGGTGCCTC   180

TGATCCCAGG GCTCACTGTG GGTCTCTCTG TTCACAGGGG TCCTGTCCCA GGTGCAGCTG   240

CAGGAGTCGG GCCCAGGACT GGTGAAGCCT TCGGAGACCC TGTCCCTCAC CTGCACTGTC   300

TCTGGTGGCT CCATCAGTAG TTACTACTGG AGCTGGATCC GGCAGCCCGC CGGGAAGGGA   360

CTGGAGTGGA TTGGGCGTAT CTATACCAGT GGGAGCACCA ACTACAACCC CTCCCTCAAG   420

AGTCGAGTCA CCATGTCAGT AGACACGTCC AAGAACCAGT TCTCCCTGAA GCTGAGCTCT   480

GTGACCGCCG CGGACACGGC CGTGTATTAC TGTGCGAGAG ACACAGTGAG GGGAGGTGAG   540

TGTGAGCCCA GACACAAACC TCCCTGCAGG GAGGCGGAGG GGACCGGCGC AGGTGCTGCT   600

CAAGACCAGC AGGGGGCGCG CGGGGCCCAC AGAGCAAGAG GCCGGGTCAG              650
```

(2) INFORMATION FOR SEQ ID NO: 5:

(i) SEQUENCE CHARACTERISTICS:
        (A) LENGTH: 613 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 5:

```
CCAGCTCCAC CCTCCTCTGG GTTGAAAAAG CCGAGCACAG GTACCAGCTC AGTGACTCCT    60
```

```
GTGCACCACC ATGGACACAC TTTGCTCCAC GCTCCTGCTG CTGACCATCC CTTCATGTGA      120

GTGCTGTGGT CAGGGACTCC TTCACGGGTG AAACATCAGT TTTCTTGTTT GTGGGCTTCA      180

TCTTCTTATG CTTTCTCCAC AGGGGTCTTG TCCCAGATCA CCTTGAAGGA GTCTGGTCCT      240

ACGCTGGTGA AACCCACACA GACCCTCACG CTGACCTGCA CCTTCTCTGG GTTCTCACTC      300

AGCACTAGTG GAGTGGGTGT GGGCTGGATC CGTCAGCCCC CAGGAAAGGC CCTGGAGTGG      360

CTTGCACTCA TTTATTGGAA TGATGATAAG CGCTACAGCC CATCTCTGAA GAGCAGGCTC      420

ACCATCACCA AGGACACCTC CAAAAACCAG GTGGTCCTTA CAATGACCAA CATGGACCCT      480

GTGGACACAG CCACATATTA CTGTGCACAC AGACCACAAA GACACAGCCC AGGGCACCTC      540

CTGTACAAAA ACCCAGGCTG CTTCTCATTG GTGCTCCCTC CCCACCTCTG CAGAACAGGA      600

AAGTCTGTCT GCT                                                        613

(2) INFORMATION FOR SEQ ID NO: 6:

(i) SEQUENCE CHARACTERISTICS:
        (A) LENGTH: 594 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 6:

ACAGGATTCA CCATGGAGTT GGGGCTGAGG TGGGTTTTCC TTGCTGCTAT TTTAAAAGGT       60

GATTTATGGT TAACTAGAGC TATTGAGTGT GAATGGACAT AAGTGAGCGA AACAGTGGAT      120

ATGTGTGGCA GTTTCTTACC AGGATGTCTC TGTGTTTGCA GGTGTCCAGT GTGAGATGCA      180

GCTGGTAGAG TCTGGAGCAA ACTTGACAAA GCCTGGGTGT CCCTGAGACT CTCCTGTGCA      240

GCCTCTGGAT TCACCTTCAG TAGCCATAGC ACGCACTGGG TCCCCCAGGC TCCAGGAAG       300

GGTCTGCAGT GGGTCCCAGT TATTAGTGGT AGTGGTAGTA CCATGTACTA CGCAGACTCT      360

GTGAAGGGCC GATTCACCAT TTCCAGAGAC AATACCAAAA ACTCACTGTA TCTGCAAATG      420

AACAGACTGA GGGCAGAGGA TGCAGCTGCA TATGACTCTG TGAGAGATAC GGTAAGGAGA      480

AGTCAGTGTG AGCCCAGACA CAAACCTCCC TTCAGGGTAC CTGGGACAAC CAGGGAAAGC      540

CTGGGACACT GTGCACTGTG CTGACCCCAG GGGCAAGTGC AGGTGCTACA AGGG           594

(2) INFORMATION FOR SEQ ID NO: 7:

(i) SEQUENCE CHARACTERISTICS:
        (A) LENGTH: 877 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 7:

ACAGCCTATT CCTCCAGCAT CCCACTAGAG CTTCTTATAT AGTAGGAGAC ATGCAAATAG       60
```

```
GGCCCTCCCT CTACTGATGA AAACCAACCC AACCCTGACC CTGCAGGTCT CAGAGAGGAG      120

CCTTAGCCCT GGACTCCAAG GCCTTTCCAC TTGGTGATCA GCACTGAGCA CAGAGGACTC      180

ACCATGGAAT TGGGGCTGAG CTGGGTTTTC CTTGTTGCTA TTTTAGAAGG TGATTCATGG      240

AAAACTAGGA AGATTGAGTG TGTGTGGATA TGAGTGTGAG AAACAGTGGA TTTGTGTGGC      300

AGTTTCTGAC CTTGGTGTCT CTTTGTTTGC AGGTGTCCAG TGTGAGGTGC AGCTGGTGGA      360

GTCTGGGGGA GGCTTGGTCC AGCCTGGGGG GTCCCTGAGA CTCTCCTGTG CAGCCTCTGG      420

ATTCACCTTT AGTAGCTATT GGATGAGCTG GGTCCGCCAG GCTCCAGGGA AGGGGCTGGA      480

GTGGGTGGCC AACATAAAGC AAGATGGAAG TGAGAAATAC TATGTGGACT CTGTGAAGGG      540

CCGATTCACC ATCTCCAGAG ACAACGCCAA GAACTCACTG TATCTGCAAA TGAACAGCCT      600

GAGAGCCGAG GACACGGCTG TGTATTACTG TGCGAGAGAC ACAGTGAGGG GAAGTCAGTG      660

TGAGCCCAGA CACAAACCTC CCTGCAGGGG TCCCTTGGGA CCACCAGGGG GCGACAGGGC      720

ATTGAGCACT GGGCTGTCTC CAGGGCAGGT GCAGGTGCTG CTGAGGGCTG GCTTCCTGTC      780

GCGGTCTGGG GCTGCCTCGT CGTCAAATTT CCCCAGGAAC TTCTCCAGAT TTACAATTCT      840

GTACTGACAT TTCATGTCTC TAAATGCAAT ACTTTTT                               877
```

(2) INFORMATION FOR SEQ ID NO: 8:

(i) SEQUENCE CHARACTERISTICS:
        (A) LENGTH: 564 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 8:

```
CACTCCACCA ACCACATCTG TCCTCTAGAG AAAACCCTGT GAGCACACCT CCTCACCATG       60

GACTGGACCT GGAGGATCCT CTTCTTGGTG GCAGCAGCTA CAAGTAAGGG GCTTCCTAGT      120

CTCAAAGCTG AGGAACGGAT CCTGGTTCAG TCAAAGAGGA TTTTATTCTC TCCTGTGTTC      180

TCTCCACAGG TGCCCACTCC CAGGTGCAGC TGGTGCAGTC TGGGGCTGAG GTGAAGAAGC      240

CTGGGGCCTC AGTGAAGGTC TCCTGCAAGG CTTCTGGATA CACCTTCACC AGTTATGATA      300

TCAACTGGGT GCGACAGGCC ACTGGACAAG GCTTGAGTG GATGGGATGG ATGAACCCTA       360

ACAGTGGTAA CACAGGCTAT GCACAGAAGT TCCAGGGCAG AGTCACCATG ACCAGGAACA      420

CCTCCATAAG CACAGCCTAC ATGGAGCTGA GCAGCCTGAG ATCTGAGGAC ACGGCCGTGT      480

ATTACTGTGC GAGAGGCACA GTGTGAAAAA CCACATCCTC AGAGAGTCAG AAACCCCTAG      540

GGGAGAAGGC AGCTTCTGCT GGGC                                             564
```

(2) INFORMATION FOR SEQ ID NO: 9:

(i) SEQUENCE CHARACTERISTICS:
        (A) LENGTH: 640 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens (G) CELL TYPE: human lymphoblast
(H) CELL LINE: CGM1

(xi) SEQUENCE DESCRIPTION: SEQ ID NO: 9:

```
CAAATAGGGC CCTCCCTCTG CTGATGAAAA CCAGCCCAGC CCTGACCCTG CAGCTCTGGG      60
AGAGGAGCCC CAGCCCTGAG ATTCCCAGGT GTTTCCATTC AGTGATCAGC ACTGAACACA     120
GAGGACTCAC CATGGAGTTG GGACTGAGCT GGATTTTCCT TTTGGCTATT TTAAAAGGTG     180
ATTCATGGAG AAATAGAGAG ATTGAGTGTG AGTGGACATG AGTGGATTTG TGTGGCAGTT     240
TCTGACCTTG GTGTCTCTGT GTTTGCAGGT GTCCAGTGTG AAGTGCAGCT GGTGGAGTCT     300
GGGGGAGGCT TGGTACAGCC TGGCAGGTCC CTGAGACTCT CCTGTGCAGC CTCTGGATTC     360
ACCTTTGATG ATTATGCCAT GCACTGGGTC CGGCAAGCTC CAGGGAAGGG CCTGGAGTGG     420
GTCTCAGGTA TTAGTTGGAA TAGTGGTAGC ATAGGCTATG CGGACTCTGT GAAGGGCCGA     480
TTCACCATCT CCAGAGACAA CGCCAAGAAC TCCCTGTATC TGCAAATGAA CAGTCTGAGA     540
GCTGAGGACA CGGCCTTGTA TTACTGTGCA AAAGATACAC AGTGAGGGGA AGTCAGCGAG     600
AGCCCAGACA AAAACCTCCT GCAGGAAGAC AGGAGGGGCC                           640
```

(2) INFORMATION FOR SEQ ID NO: 10:

(i) SEQUENCE CHARACTERISTICS:
(A) LENGTH: 630 base pairs
(B) TYPE: nucleic acid
(C) STRANDEDNESS: double
(D) TOPOLOGY: linear (ii) MOLECULE TYPE: Genomic DNA (vi) ORIGINAL SOURCE:
(A) ORGANISM: Homo sapiens
(G) CELL TYPE: human lymphoblast
(H) CELL LINE: CGM1

(xi) SEQUENCE DESCRIPTION: SEQ ID NO: 10:

```
AGCTCCACCC TTCTCTGTGT TGAAAAGCCG AGCATGGGGA CCTAGTTCAG TGACTCCTGC      60
GCCCCACCAC ATGGAGCTTT ACTCCACGCT TCTCCTGCTG ACTGTCCCTT CCTGTGAGTT     120
CAGTGGTCAG GGAATCCTTC AGGGGTGAAA CACCTGTTCT TTTCTTTGTG GGCTTCATCT     180
TCTTATGCTT TCTCCACAGG GGTCTTATCC CAGGTCACCT TGAAGGAGTC TGGTCCTGCA     240
CTGGTGAAAC CCACACAGAC CCTCATGCTG ACCTGCACCT TCTCTGGGTT CTCACTCAGC     300
ACTTCTGGAA TGGGTGTGGG TTAGATCTGT CAGCCCTCAG CAAAGGCCCT GGAGTGGCTT     360
GCACACATTT ATTAGAATGA TAATAAATAC TACAGCCCAT CTCTGAAGAG TAGGCTCATT     420
ATCTCCAAGG ACACCTCCAA GAATGAAGTG GTTCTAACAG TGATCAACAT GGACATTGTG     480
GACACAGCCA CACATTACTG TGCAAGGAGA CCACAGAGAC AGAGCCCAGG GTGCCTCTTG     540
TACAAGACCC AGGCTGCTTC TCAGTGGCGC TCCCTCCCCA CCTCTGCAGA ACAGGAAAGT     600
GTGGCTGAGA TGCCATTTCC TGTCAGGGTC                                      630
```

(2) INFORMATION FOR SEQ ID NO: 11:

(i) SEQUENCE CHARACTERISTICS:
(A) LENGTH: 715 base pairs
(B) TYPE: nucleic acid
(C) STRANDEDNESS: double
(D) TOPOLOGY: linear (ii) MOLECULE TYPE: Genomic DNA (vi) ORIGINAL SOURCE:

(A) ORGANISM: Homo sapiens
    (G) CELL TYPE: human lymphoblast
    (H) CELL LINE: CGM1

(xi) SEQUENCE DESCRIPTION: SEQ ID NO: 11:

```
CACCCCAGGC TTTACACTTT ATGCTTCCGG CTCGTATGTT GTGTGGAATT GTGAGCGGAT    60

AACAATTTCA CACAGGAAAC AGCTATGACC ATGATTACGC CAAGCTTGCA TGCCTGCAGG   120

TCGACTCTAG AGGATCCCCG GGTACCGAGC TCGAATTCCC AGGAGTTTCC ATTCGGTGAT   180

CAGCACTGAA CACAGAGGAC TCACCATGGA GTTTGGGCTG AGCTGGGTTT TCCTTGTTGC   240

TATAATAAAA GGTGATTTAT GGAGAACTAG AGACATTGAG TGGACGTGAG TGAGATAAGC   300

AGTGAATATA TGTGGCAGTT TCTGACTAGG TTGTCTCTGT GTTTGCAGGT GTCCAGTGTC   360

AGGTGCAGCT GGTGGAGTCT GGGGGAGGCT TGGTCAAGCC TGGAGGGTCC CTGAGACTCT   420

CCTGTGCAGC CTCTGGATTC ACCTTCAGTG ACTACTACAT GAGCTGGATC CGCCAGGCTC   480

CAGGGAAGGG GCTGGAGTGG GTTTCATACA TTAGTAGTAG TGGTAGTACC ATATACTACG   540

CAGACTCTGT GAAGGGCCGA TTCACCATCT CCAGGGACAA CGCCAAGAAC TCACTGTATC   600

TGCAAATGAA CAGCCTGAGA GCCGAGGACA CGGCCGTGTA TTACTGTGCG AGAGACACAG   660

TGAGGGGAAG TCAGTGTGAG CCCAGACACA AACCTCCCTG CAGGGGGTCC CTTGG        715
```

(2) INFORMATION FOR SEQ ID NO: 12:

(i) SEQUENCE CHARACTERISTICS:
        (A) LENGTH: 660 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 12:

```
GGATTGGGCT TTGAGCTAAG GANAGGCTTT GTCNNATGAA TATNCGAATA TACTGATATC    60

CACTGAGNTG AAATATGTTCT GTNCCCTGAG AGAATCACCT GAGAGAATCC CCTGAGAGCA  120

CATCTCCTCA TGGNCTGGAC CTACAAGATC CTCTTCTTGG TGGCAGCAGC CACAGGTAAG   180

CAGTTCCCAG GTCCAAGTAA TGAGGAGGGG ATTGAGTCCA GTCAAGGGGG CTTTCATCCA   240

CTCCTGTGTC CTCCCCACAG GTGCCCACTC CCAGGTGCAG CTGGTGCAAT CTGGGGCTGA   300

GGTGAAGAAG CCTGGGGCCT CAGTGAAGGT CTCCTGCAAG GCTTCTGGAT ACACCTTCAC   360

CTACTGCTAC TTGCACTGGG TATGACAGGC CCCTGGACAA GGGCTTGAAT GGACAGGATT   420

TTAGTTATTT GAGAGATTTT TCATACAACA TTTATTCTGT AAGCAAATTT CAGGGATTGT   480

AGAATGAATC ATATTAACAA ATCTGACACA GAACTTCCTC TGAATCAATC TTTGTAAACA   540

TCAATTTCTG AATCAATGTT GTNAATATTT CAGAACACAA GCACAANTTC ACATTTNAAC   600

TCTACTTTNA TCTCTATTTA AAANATATCA AAAANTCTCA TCNNGTGCAT GTAACGTTTG   660
```

(2) INFORMATION FOR SEQ ID NO: 13:

(i) SEQUENCE CHARACTERISTICS:
        (A) LENGTH: 819 base pairs
        (B) TYPE: nucleic acid
        (C) STRANDEDNESS: double
        (D) TOPOLOGY: linear -continued (ii) MOLECULE TYPE: Genomic DNA (vi) ORIGINAL SOURCE:
    (A) ORGANISM: Homo sapiens
    (G) CELL TYPE: human lymphoblast
    (H) CELL LINE: CGM1

(xi) SEQUENCE DESCRIPTION: SEQ ID NO: 13:

```
AATAAAAAAA TGATAGTTGT TAAATGTTTA TCGCAGAACA ATTCCAAATA AGGCAGCATT      60
TTCCCCAAAT ACAATCATTG TCATCCAAAA TCCCCCAGGA CGCTCTCATC TACTCTGCCC     120
CTGCCTTCAC CTCAGATGTC CCACCCCAGA GCTTGCTATA TAGTAACAGA CATGCAAATA     180
GTTGACTCCC TCTCCTGATG AAAACCAGCC CAGCCCTGAC CCTGCAGCTC TGGGAGTGGA     240
GCCCCAGCCT TGGGATTCCC AAGTGTTTGT ATTCAGTGAT CAGGACTGAA CACACAGGAC     300
TCACCATGGA GTTGGGGCTG AGCTGGGTTT TCCTTGTTGC TATATTAGAA GGTGATTCAT     360
GGAGAACTAG AGATATTGAG TGTGAATGGG CATGAATGAG AGAAACAGTG GGTATGTGTG     420
GCAATTTCTG ACTTTTGTGT CTCTGTGCCT TGCAGGTGTC CAGTGTGAGG TGCATCTGGT     480
GGAGTCTGGG GGAGGCTTGG TACAGCCTGG GGGGGCCCTG AGACTCTCCT GTGCAGCCTC     540
TGGATTCACC TTCAGTAACT ACGACATGCA CTGGGTCCGC CAAGCTACAG GAAAAGGTCT     600
GGAGTGGGTC TCAGCCAATG GTACTGCTGG TGACACATAC TATCCAGGCT CCGTGAAGGG     660
GCGATTCACC ATCTCCAGAG AAAATGCCAA GAACTCCTTG TATCTTCAAA TGAACAGCCT     720
GAGAGCCGGG GACACGGCTG TGTATTACTG TGCAAGAGAC ACAGTGAGGG GAAGTCAGTA     780
TGAGCCCAGA CACAAACCTC CCTGCAGAAT GCCTGGGGG                           819
```

(2) INFORMATION FOR SEQ ID NO: 14:

(i) SEQUENCE CHARACTERISTICS:
        (A) LENGTH: 816 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 14:

```
AGNGANGAAG GNAGTGATCA CTGTGATCTT TTCNCCAAGT TCACCATTTC NCTGAAGGTG      60
AGCACAGGTC CTCCTGCATG TGTTCAAACA AAAGNNNNAG AGACTACCTG GTAAGTGAGG     120
TGCTCACCTG GTTCTGGATG TTTGGTCTGT CTCCTCCCCT CTGTTGCCCC ACACAAGGTC     180
AGCCCACTCT TTCCAGGTCC GAAGAAGAGA GCACAGGTTT GTCCTGATTA TATGACTCAC     240
CCAGCTTCTG ATGACTCTCC TGTTGCCAGC GTCCATGGCC TCAGTGAAGG TCTCCTGCAA     300
AGCTCTGGAT ACACCTTCGC CAGCTACGAC ATTCACTGTG TGTGACAGGC CCCTGGATAA     360
GGGTTTGANT GGATGGTAGG GAGCTACTCT GGCAATGGTA ACACAGGCTA TGCACAGAAG     420
TTTCAGGGCA GAGTCACCAT GACCAGGGAC ACGTCCACGA GCACAGCCTA CATGGAGCTG     480
AGCAGTCAGA GATCTGAGGA CATAGATGTG TACTACTGTG CGANACACAC AGTGTGACAN     540
CCCACATCCT GAGAGAGTCA GAAATCCTGA GGGAGGTGGC AGCAGTGCTA GGCTTGAGAG     600
ATGACAGGGA TTTTATTTGC TTTNNCGGCT TTTTTTNGNN AGCGAGGTTA NTTCATTACA     660
GANNNNNGGA AAATAGAAAT GTGTATGGAC TCTAATTATG TGGGAAATTT CCATACAACT     720
```

```
TTGGTTCTCT TNGNNNNTTC AGGGGTNGGA NNCAATCAAT TAATAACCTG ATAAAGATTC      780

GAGTCGTACC CNGGATCCCT GNTTCGCCTG AGNATA                                816
```

(2) INFORMATION FOR SEQ ID NO: 15:

(i) SEQUENCE CHARACTERISTICS:
        (A) LENGTH: 535 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 15:

```
CACAGAGGAC TCACCATGGA GTTTGGGCTG AGCTGGATTT TCCTTCCTGC TATTTTAAAA       60

GGTGATTTAT GGAGAACTAG AGAGATTAAG TGTGAGTGGA CGTGAGTGAG AGAAACAGTG      120

GATATGTGTG GCAGTTTCTG ATCTTAGTGT CTCTGTGTTT GCAGGTGTCC AGTGTGAGGT      180

GCAGCTGGTG GAGTCTGGGG GAGCCTTGGT AAAGCCTGGG GGGTCCCTTA GACTCTCCTG      240

TGCAGCCTCT GGATTCACTT TCAGTAACGC CTGGATGAGC TGGGTCCGCC AGGCTCCAGG      300

GAAGGGGCTG GAGTGGGTTG GCCGTATTAA AAGCAAAACT GATGGTGGGA CAACAGACTA      360

CGCTGCACCC GTGAAAGGCA GATTCACCAT CTCAAGAGAT GATTCAAAAA ACACGCTGTA      420

TCTGCAAATG AACAGCCTGA AAACCGAGGA CACAGCCGTG TATTACTGTA CCACAGACAC      480

AGTGAGGGGA GGTCAGTGTG AGCCCGGACA CAAACCTCCC TGCAGGGGCG CGCGG          535
```

(2) INFORMATION FOR SEQ ID NO: 16:

(i) SEQUENCE CHARACTERISTICS:
        (A) LENGTH: 542 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 16:

```
ATTGGGTCAA CAGCAATAAA CAAATTACCA TGGAATTTGG GCTGAGCTGG GTTTTTCTTG       60

CTGGTATTTT AAAAGGTGAT TCATGGAGAA CTAAGGATAT TGAGTGAGTG GACATGAGTG      120

AGAGAAACAG TGGATATGTG TGGCAGTTTC TGACCAGGGT GTCTCTGTGT TTGCAGGTGT      180

CCAGTGTGAG GTACAACTGG TGGAGTCTGG GGGAGGCTTG GTACAGCCTG GGGGGTCCCT      240

GAGACTCTCC TGTGCAGCCT CTGGATTCAC CTTCAGTAAC AGTGACATGA ACTGGGCCCG      300

CAAGGCTCCA GGAAAGGGGC TGGAGTGGGT ATCGGGTGTT AGTTGGAATG GCAGTAGGAC      360

GCACTATGTG GACTCCGTGA AGCGCCGATT CATCATCTCC AGAGACAATT CCAGGAACTC      420

CCTGTATCTG CAAAAGAACA GACGGAGAGC CGAGGACATG GCTGTGTATT ACTGTGTGAG      480

AAATCCTGTG AGGGGACACA AGTGCGAGCC CAGACACAAA CCTCCTGCAG GAACACTGGG      540

CG                                                                     542
```

(2) INFORMATION FOR SEQ ID NO: 17:

(i) SEQUENCE CHARACTERISTICS:
        (A) LENGTH: 591 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 17:

```
ACATCCCTCC TCTATAGAAG CCCCTGAGAG CACAGCTCCT CACCATGGAC TGTACCTGGG    60
GGATCCTCTT CTTGGTGGCA TCTNCCACAG GTAAGGGGCT CCCAAGTCCT AGTGATGAGG   120
AGGGGATTGA GTCCAGTCAA GGGGGCTTTT ATCATCTCCT CCCTTCTCCT CACAGATGTC   180
CATTCCCAGG TTCAGCTGTT GCAGCCTGGG GCTGAGGTGA AGAAGCCTGC GTCCTCAGTG   240
AAGGTCTCCT GGCCAGGCTT CCAGATACAC CTTCACCAAA TACTTTACAC AGTGGGTGCG   300
ACAGGGCCCT GGACAAGGGC ATAGTGGTTG GGATGCATCA ACCCTTACAA TGATAACACA   360
CACTACGCAC AGAAGTTCCG GGGCAGAGTC ACCATTACCA GTGACAGGTC CGTGAGCACA   420
GCCTACATGG AGCTGAGCAG TCTGAGATCT GAAGACATGG TCGTGTATTC CTGTGTGAGA   480
GACACAGTGC GAAAACCCAC ATCCTGAGAG TGTCAGAAAC CCAGGAAGG AGGCACCTGT    540
GCTGACACAG AGGGAGATGA CAAAGATTAT TAGATTAACG ATTTTCTTAG A            591
```

(2) INFORMATION FOR SEQ ID NO: 18:

(i) SEQUENCE CHARACTERISTICS:
        (A) LENGTH: 539 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 18:

```
CAAACACCCC TCCTTGGGAG AATCCCCTAG ATCACAGCTC CTCACCATGG ACTGGACCTG    60
GAGCATCCTT TTCTTGGTGG CAGCACCAAC AGGTAACGGA CTCCCCAGTC CCAGGGCTGA   120
GAGAGAAACC AGGCCAGTCA TGTGAGACTT CACCCACTCC TGTGTCCTCT CCACAGGTGC   180
CCACTCCCAG GTTCAGCTGG TGCAGTCTGG AGCTGAGGTG AAGAAGCCTG GGGCCTCAGT   240
GAAGGTCTCC TGCAAGGCTT CTGGTTACAC CTTTACCAGC TATGGTATCA GCTGGGTGCG   300
ACAGGCCCCT GGACAAGGGC TTGAGTGGAT GGGATGGATC AGCGCTTACA ATGGTAACAC   360
AAACTATGCA CAGAAGCTCC AGGGCAGAGT CACCATGACC ACAGACACAT CCACGAGCAC   420
AGCCTACATG GAGCTGAGGA GCCTGAGATC TGACGACACG GCCGTGTATT ACTGTGCGAG   480
AGACACAGTG TGAAAACCCA CATCCTGAGG GTTTCAGAAA CCCCAGGGAG GAGGCAGCT    539
```

(2) INFORMATION FOR SEQ ID NO: 19:

(i) SEQUENCE CHARACTERISTICS:
        (A) LENGTH: 727 base pairs
        (B) TYPE: nucleic acid (C) STRANDEDNESS: double
            (D) TOPOLOGY: linear (ii) MOLECULE TYPE: Genomic DNA (vi) ORIGINAL SOURCE:
            (A) ORGANISM: Homo sapiens
            (G) CELL TYPE: human lymphoblast
            (H) CELL LINE: CGM1

(xi) SEQUENCE DESCRIPTION: SEQ ID NO: 19:

```
AGATTTAAGA ACCTTGCACC TGGTACCCGT TGCTCTTCTT GTAACCATTT GTCTTTTAAG      60

TTGTTTATCA CTCTGTAACT ATTTTGATTA TTTTGATTCT TGCATGTTTT TACTTCTGTA     120

AAATTATTAC ATTTGAGTCC CTCTCCCCTT CCTAAACCTA GGTATAAAAT TTACTCGAGC     180

CCCTTCCTCG TGGCCGAGAG AATTTTGAGC ATGAGCTGTC TCTTTGGCAG CCGGCTTAAT     240

AAAGGACTCT TAATTCGTCT CAAAGTGTGG CGTTTTCTTA ACTCACCTGG GTACAACAGT     300

GCAGCTGGTG GAGTCTGGGG GAGGCTTGGT AGAGCCTGGG GGGTCCCTGA GACTCTCCTG     360

TGCAGCCTCT GGATTCACCT TCAGTAACAG TGACATGAAC TGGGTCCGCC AGGCTCCAGG     420

AAAGGGGCTG GAGTGGGTAT CGGGTGTTAG TTGGAATGGC AGTAGGACGC ACTATGCAGA     480

CTCTGTGAAG GGCCGATTCA TCATCTCCAG AGACAATTCC AGGAACTTCC TGTATCAGCA     540

AATGAACAGC CTGAGGCCCG AGGACATGGC TGTGTATTAC TGTGTGAAA  ACACTGTGAG     600

AGGACGGAAG TGTGAGCCCA GACACAAACC TCCTGCAGGA ACGTTGGGGG AAATCAGCTG     660

CAGGGGGCGC TCAAGACCCA CTCATCAGAG TCAACCCCAG AGCAGGTGCA CATGGAGGCT     720

GGGTTTT                                                              727
```

(2) INFORMATION FOR SEQ ID NO: 20:

(i) SEQUENCE CHARACTERISTICS:
            (A) LENGTH: 514 base pairs
            (B) TYPE: nucleic acid
            (C) STRANDEDNESS: double
            (D) TOPOLOGY: linear (ii) MOLECULE TYPE: Genomic DNA (vi) ORIGINAL SOURCE:
            (A) ORGANISM: Homo sapiens
            (G) CELL TYPE: human lymphoblast
            (H) CELL LINE: CGM1

(xi) SEQUENCE DESCRIPTION: SEQ ID NO: 20:

```
GGACTCGCCA TGGAGTTTGG GCTGAGCTGG GTTTTCCTTG TTGCTATTTT AAAAGGTGAT      60

TCATGGATCA ATAGAGATGT TGAGTGTGAG TGAACACGAG TGAGAGAAAC AGTGGATTTG     120

TGTGGCAGTT TCTGACCAGG GTGTCTCTGT GTTTGCAGGT GTCCAGTGTG AGGTGCAGCT     180

GGTGGAGTCT GGGGGAGGTG TGGTACGGCC TGGGGGGTCC CTGAGACTCT CCTGTGCAGC     240

CTCTGGATTC ACCTTTGATG ATTATGGCAT GAGCTGGGTC CGCCAAGCTC AGGGAAGGG     300

GCTGGAGTGG GTCTCTGGTA TTAATTGGAA TGGTGGTAGC ACAGGTTATG CAGACTCTGT     360

GAAGGGCCGA TTCACCATCT CCAGAGACAA CGCCAAGAAC TCCCTGTATC TGCAAATGAA     420

CAGTCTGAGA GCCGAGGACA CGGCCTTGTA TCACTGTGCG AGAGACACAG TGAGGGGAAG     480

CCAGTGAGAG CCCAGACACA AACGTCCCTG CAGG                                514
```

(2) INFORMATION FOR SEQ ID NO: 21:

(i) SEQUENCE CHARACTERISTICS:
            (A) LENGTH: 519 base pairs (B) TYPE: nucleic acid
          (C) STRANDEDNESS: double
          (D) TOPOLOGY: linear (ii) MOLECULE TYPE: Genomic DNA (vi) ORIGINAL SOURCE:
          (A) ORGANISM: Homo sapiens
          (G) CELL TYPE: human lymphoblast
          (H) CELL LINE: CGM1

(xi) SEQUENCE DESCRIPTION: SEQ ID NO: 21:

AGGATTCACC ATGGAACTGG GGCTCCGCTG GGTTTTCCTT GTTGCTATTT TAGAAGGTGA      60

ATCATGGAAA AGTAGAGAGA TTTAGTGTGT GTGGATATGA GTGAGAGAAA CGGTGGATGT     120

GTGTGACAGT TTCTGACCAA TGTCTCTCTG TTTGCAGGTG TCCAGTGTGA GGTGCAACTG     180

GTGGAGTCTG GGGGAGGCCT GGTCAAGCCT GGGGGGTCCC TGAGACTCTC CTGTGCAGCC     240

TCTGGATTCA CCTTCAGTAG CTATAGCATG AACTGGGTCC GCCAGGCTCC AGGGAAGGGG     300

CTGGAGTGGG TCTCATCCAT TAGTAGTAGT AGTAGTTACA TATACTACGC AGACTCAGTG     360

AAGGGCCGAT TCACCATCTC CAGAGACAAC GCCAAGAACT CACTGTATCT GCAAATGAAC     420

AGCCTGAGAG CCGAGGACAC GGCTGTGTAT TACTGTGCGA GAGACACAGT GAGGGGAAGT     480

CAGTGTGAGC CCAGACACAA ACCTCCCTGC AGGGGTCCC                            519

(2) INFORMATION FOR SEQ ID NO: 22:

(i) SEQUENCE CHARACTERISTICS:
          (A) LENGTH: 606 base pairs
          (B) TYPE: nucleic acid
          (C) STRANDEDNESS: double
          (D) TOPOLOGY: linear (ii) MOLECULE TYPE: Genomic DNA (vi) ORIGINAL SOURCE:
          (A) ORGANISM: Homo sapiens
          (G) CELL TYPE: human lymphoblast
          (H) CELL LINE: CGM1

(xi) SEQUENCE DESCRIPTION: SEQ ID NO: 22:

CTACAGCTCT GGGAGAGGAC CCCCAGCCCT GGGATTTTCA GATGTTTTCA TTTGGTGATC      60

AGGACTGAAC ACAGAGGACT CACCATGGAG TCATGGCTGA GCTGGGTTTT TCTTGCCGCT     120

ATTTTAAAAG GTAATTCATT GAGAACTATT GAAATTGAGT GTGAGCGGAT AAGAGTGAGA     180

GAAACAGTGG ATACGTGTGG CAGTTTCTGA CCAGGGTTTC TTTTTGTTTG CAGGTGTCCA     240

GTGTGAGGTG CATCTGGTGG AGTCTGGGGG AGCCTTGGTA CAGCCTGGGG GGTCCCTGAG     300

ACTCTCCTGT GCAGCCTCTG GATTCACCTT CAGTTACTAC TACATGAGCG GGTCCGCCA     360

GGCTCCCGGG AAGGGGCTGG AATGGGTAGG TTTCATTAGA AACAAAGCTA ATGGTGGGAC     420

AACAGAATAG ACCACGTCTG TGAAAGGCAG ATTCACAATC TCAAGAGATG ATTCCAAAAG     480

CATCACCTAT CTGCAAATGA AGAGCCTGAA AACCGAGGAC ACGGCCGTGT ATTACTGTTC     540

CAGAGACACA GTGAGGGGAG GTCAGTGTGA GCCCGGACAC AAACCTCCCT GCAGGGGCGC     600

GCGGGG                                                                606

(2) INFORMATION FOR SEQ ID NO: 23:

(i) SEQUENCE CHARACTERISTICS:
          (A) LENGTH: 514 base pairs
          (B) TYPE: nucleic acid
          (C) STRANDEDNESS: double
          (D) TOPOLOGY: linear

```
      (ii) MOLECULE TYPE: Genomic DNA (vi) ORIGINAL SOURCE:
           (A) ORGANISM: Homo sapiens
           (G) CELL TYPE: human lymphoblast
           (H) CELL LINE: CGM1

(xi) SEQUENCE DESCRIPTION: SEQ ID NO: 23:

GAACTCACCA TGGAGTTTGG GCTGAGCTGG CTTTTTCTTG TGGCTAAAAT AAAAGGTAAT     60

TCATGGAGAA ATAGAAAAAT TGAGTGTGAA TGGATAAGAG TGAGAGAAAC AGTGGATACG    120

TGTGGCAGTT TCTGACCAGG GTTTCTTTTT GTTTGCAGGT GTCCAGTGTG AGGTGCAGCT    180

GTTGGAGTCT GGGGGAGGCT TGGTACAGCC TGGGGGGTCC CTGAGACTCT CCTGTGCAGC    240

CTCTGGATTC ACCTTTAGCA GCTATGCCAT GAGCTGGGTC CGCCAGGCTC CAGGGAAGGG    300

GCTGGAGTGG GTCTCAGCTA TTAGTGGTAG TGGTGGTAGC ACATACTACG CAGACTCCGT    360

GAAGGGCCGG TTCACCATCT CCAGAGACAA TTCCAAGAAC ACGCTGTATC TGCAAATGAA    420

CAGCCTGAGA GCCGAGGACA CGGCCGTATA TTACTGTGCG AAAGACACAG TGAGGGGAAG    480

TCATTGTGAG CCCAGACACA AACCTCCCTG CAGG                                514

(2) INFORMATION FOR SEQ ID NO: 24:

(i) SEQUENCE CHARACTERISTICS:
           (A) LENGTH: 600 base pairs
           (B) TYPE: nucleic acid
           (C) STRANDEDNESS: double
           (D) TOPOLOGY: linear (ii) MOLECULE TYPE: Genomic DNA (vi) ORIGINAL SOURCE:
           (A) ORGANISM: Homo sapiens
           (G) CELL TYPE: human lymphoblast
           (H) CELL LINE: CGM1

(xi) SEQUENCE DESCRIPTION: SEQ ID NO: 24:

CCCAGAGACC ATCACACAAC AGCCACATCC CTCCCCTACA GAAGCCCCCA GAGCGCAGCA     60

CCTCACCATG GACTGCACCT GGAGGATCCT CTTCTTGGTG GCAGCAGCTA CAGGCAAGAG    120

AATCCTGAGT TCCAGGTCTG ATGAGGGGAC TGGGTCCAGT TAAGTGGTGT CTCATCCACT    180

CCTCTGTCCT CTCCACAGGC ACCCACGCCC AGGTCCAGCT GGTACAGTCT GGGGCTGAGG    240

TGAAGAAGCC TGGGGCCTCA GTGAAGGTCT CCTGCAAGGT TTCCGGATAC ACCCTCACTG    300

AATTATCCAT GCACTGGGTG CGACAGGCTC CTGGAAAAGG GCTTGAGTGG ATGGGAGGTT    360

TTGATCCTGA AGATGGTGAA ACAATCTACG CACAGAAGTT CCAGGGCAGA GTCACCATGA    420

CCGAGGACAC ATCTACAGAC ACAGCCTACA TGGAGCTGAG CAGCCTGAGA TCTGAGGACA    480

CGGCCGTGTA TTACTGTGCA ACAGACACAG TGTGAAAACC CACATCCTGA GAGCGTCAGA    540

AACCCTGAGG AATGAGGCAG CTGTGCTGAG GCTGAGGAGA TGACAGGATT TATGAAGTTT    600

(2) INFORMATION FOR SEQ ID NO: 25:

(i) SEQUENCE CHARACTERISTICS:
           (A) LENGTH: 655 base pairs
           (B) TYPE: nucleic acid
           (C) STRANDEDNESS: double
           (D) TOPOLOGY: linear (ii) MOLECULE TYPE: Genomic DNA (vi) ORIGINAL SOURCE:
           (A) ORGANISM: Homo sapiens
```

(G) CELL TYPE: human lymphoblast
(H) CELL LINE: CGM1

(xi) SEQUENCE DESCRIPTION: SEQ ID NO: 25:

| | | | | | |
|---|---|---|---|---|---|
| ATTCACGTTT | TCGAGCTCGG | TACCCGGGGG | ATCCTCTAGA | GTCGACCTGC | AGCTCTGGGA | 60
| GAGGAGCCCA | GCCCCCGAAT | TCCCAGGTGT | TTTCATCTGG | TGATCAGCAC | CGAACACAGA | 120
| GGACTCACCA | TGGAGTTTGT | GCTGAGCTGG | GTTTTCCTTG | TTGCTATTTT | AAAACGTGAT | 180
| CTATAGAGAA | CTAGAGATAT | TGAGTATGAA | TGGATATGAG | TGAGAAACAG | TGGATACGTG | 240
| TGGCAGTTTC | TGACCGGGGT | GTCTCTGTGT | TTGCAGGTAT | CCAGTGTGAG | ATGCAGCTGG | 300
| TGGAGTCTGG | GGGAGGCTTG | CAAAAGCCTG | CGTGGTCCCC | GAGACTCTCC | TGTGCAGCCT | 360
| CTCAATTCAC | CTTCAGTAGC | TACTACATGA | ACTGTGTCCG | CCAGGCTCCA | GGGAATGGGC | 420
| TGGAGTTGGT | TTGACAAGTT | AATCCTAATG | GGGGTAGCAC | ATACCTCATA | GACTCCGGTA | 480
| AGGACCGATT | CAATACCTCC | AGAGATAACG | CCAAGAACAC | ACTTCATCTG | CAAATGAACA | 540
| GCCTGAAAAC | CGAGGACACG | GCCCTCTATT | AGTGTACCAG | AGACACAGTG | AGGGGAGGTC | 600
| AGTGTGAGCC | CAGACACAAA | CCTCCCTGCA | GGCATGCAAG | CTTGGCACTG | ACCGT | 655

(2) INFORMATION FOR SEQ ID NO: 26:

(i) SEQUENCE CHARACTERISTICS:
       (A) LENGTH: 546 base pairs
       (B) TYPE: nucleic acid
       (C) STRANDEDNESS: double
       (D) TOPOLOGY: linear (ii) MOLECULE TYPE: Genomic DNA (vi) ORIGINAL SOURCE:
       (A) ORGANISM: Homo sapiens
       (G) CELL TYPE: human lymphoblast
       (H) CELL LINE: CGM1

(xi) SEQUENCE DESCRIPTION: SEQ ID NO: 26:

| | | | | | |
|---|---|---|---|---|---|
| AGTGACTCCT | GTGCCCCACC | ATGGACACAC | TTTGCTACAC | ACTCCTGCTG | CTGACCACCC | 60
| CTTCCTGTGA | GTGCTGTGGT | CAGGGACTTC | CTCAGAAGTG | AAACATCAGT | TGTCTCCTTT | 120
| GTGGGCTTCA | TCTTCTTATG | TCTTCTCCAC | AGGGGTCTTG | TCCCAGGTCA | CCTTGAAGGA | 180
| GTCTGGTCCT | GTGCTGGTGA | AACCCACAGA | GACCCTCACG | CTGACCTGCA | CCGTCTCTGG | 240
| GTTCTCACTC | AGCAATGCTA | GAATGGGTGT | GAGCTGGATC | CGTCAGCCCC | CAGGGAAGGC | 300
| CCTGGAGTGG | CTTGCACACA | TTTTTTTCGAA | TGACGAAAAA | TCCTACAGCA | CATCTCTGAA | 360
| GAGCAGGCTC | ACCATCTCCA | AGGACACCTC | CAAAAGCCAG | GTGGTCCTTA | CCATGACCAA | 420
| CATGGACCCT | GTGGACACAG | CCACATATTA | CTGTGCACGG | ATACCACAGA | GACACAGCCC | 480
| AGGATGCCTC | CTGTACAAGA | ACCTAGCTGC | ATCTCAGTGG | TGCTCCCTCC | CTACCTCTGC | 540
| AGAACA | | | | | | 546

(2) INFORMATION FOR SEQ ID NO: 27:

(i) SEQUENCE CHARACTERISTICS:
       (A) LENGTH: 587 base pairs
       (B) TYPE: nucleic acid
       (C) STRANDEDNESS: double
       (D) TOPOLOGY: linear (ii) MOLECULE TYPE: Genomic DNA (vi) ORIGINAL SOURCE:
       (A) ORGANISM: Homo sapiens
       (G) CELL TYPE: human lymphoblast (H) CELL LINE: CGM1

(xi) SEQUENCE DESCRIPTION: SEQ ID NO: 27:

```
TGAGAGCATC ATCCAACAAC CACAACTCTC CTCAGAAGAA GCCCCTAGAC CACAGCACCT      60
CAACATGTAC TGGACCTGGA GGATCCTCTT CTTGGTGGCA GCAGCAACAG GTAAGGGACC     120
TCCCAGTCAC CGGGCTGAGA GAGAAACCAG GCCAGTCAAG TGAGACTTCA CGCACTCCTG     180
TCTCCTCTCC ACAGGTGTCC ACTCACAGGT GCAGCTGGTG CAGTCTGGGC CTGAGGTGAA     240
GAAGCCTGGA GCCTCATTGA AGGTTTCCTG CAAGGCTTCT GGATACACCT TCACAAGCTA     300
TGCTATCAGC TGGGTATGAC AGGCCCATGG ACAAGGGCTT GAGGAAATGG GATGGATCAA     360
CACCAACACT GGGAACCTAA CGTATGCCCA GGGCTTCACA GGACGGTTTG TCTTCTCCAT     420
GGACACCTCC GTCAGCATGG CATATCTTCA TATCAGCAGC CTAAAGGCTG AGGACACGTG     480
CAAGAGGCAC AGTGTGGAAA CCCACATCCT GAGAGAACCA GAAATCCTGA GGGAGGAGGC     540
AGCTGTGCTG AGCTGAGGCA GTGACAGGGA CAACGTGGCT GCACCCT                  587
```

(2) INFORMATION FOR SEQ ID NO: 28:

(i) SEQUENCE CHARACTERISTICS:
    (A) LENGTH: 624 base pairs
    (B) TYPE: nucleic acid
    (C) STRANDEDNESS: double
    (D) TOPOLOGY: linear (ii) MOLECULE TYPE: Genomic DNA (vi) ORIGINAL SOURCE:
    (A) ORGANISM: Homo sapiens
    (G) CELL TYPE: human lymphoblast
    (H) CELL LINE: CGM1

(xi) SEQUENCE DESCRIPTION: SEQ ID NO: 28:

```
CATCCCTTTT CACCTCTCCA TACAGAGGCA CCACCCACAT GCAAATCTCA CTTAGGCACC      60
CAAGGGAAAC CATCACACAT TTCCTTAAAT TCAGGGTCCT GCTCACATGG GAAATACTTT     120
CTGAGAGCTC TGGACCTCCT GTGCAAGAAC ATGAAACACC TGTGGTTCTT CCTCCTGCTG     180
GTGGCAGCTC CCAGATGTGA GTGTCTCAAG GCTGCAGACA TGGAGATATG GGAGGTGCCT     240
CTGAGCCCAG GGCTCACTGT GGGTCTCTCT GTTCACAGGG GTCCTGTCCC AGGTGCAGCT     300
GCAGGAGTCG GGCCCAGGAC TGGTGAAGCC TTCGGACACC CTGTCCCTCA CCTGCGCTGT     360
CTCTGGTTAC TCCATCAGCA GTAGTAACTG GTGGGGCTGG ATCCGGCAGC CCCCAGGGAA     420
GGGACTGGAG TGGATTGGGT ACATCTATTA TAGTGGGAGC ACCTACTACA ACCCGTCCCT     480
CAAGAGTCGA GTCACCATGT CAGTAGACAC GTCCAAGAAC CAGTTCTCCC TGAAGCTGAG     540
CTCTGTGACC GCCGTGGACA CGGCCGTGTA TTACTGTGCG AGAAACACAG TGAGGGAGG     600
TGAGTGTGAG CCCAGACACA AACC                                           624
```

(2) INFORMATION FOR SEQ ID NO: 29:

(i) SEQUENCE CHARACTERISTICS:
    (A) LENGTH: 304 base pairs
    (B) TYPE: nucleic acid
    (C) STRANDEDNESS: double
    (D) TOPOLOGY: linear (ii) MOLECULE TYPE: Genomic DNA (vi) ORIGINAL SOURCE:
    (A) ORGANISM: Homo sapiens
    (G) CELL TYPE: human lymphoblast
    (H) CELL LINE: CGM1

(xi) SEQUENCE DESCRIPTION: SEQ ID NO: 29:

```
GTCAGATACA CCATGCAGAC TCTGTGAAGG GCAGATTCTC CATCTCCAAA GACAATGCTA        60

AGAACTCTCT GTATCTGCAA ATGAACAGTC AGAGAACTGA GGACATGGCT GTGTATGGCT       120

GTACATAAGG TTCCAAGTGA GGAAACATCG GTGTGAGTCC AGACACAAAA TTTCCTGCAA       180

AAAGAAGAAA GGAGTCTGGG CCAAAGGGGA CACTCAGCAC TCACAAAACA GGTGCAGCCC       240

CACGGCAGGT GCAGATGGAG GGAGGGTAAG GGCTGNTTTC CTTCAGGATC TGTGGGTTTC       300

CTCT                                                                    304
```

(2) INFORMATION FOR SEQ ID NO: 30:

(i) SEQUENCE CHARACTERISTICS:
        (A) LENGTH: 512 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 30:

```
GGACTCACCA TGGAGTTTGG GCTGAGCTGG GTTTTCCTCG TTGCTCTTTT AAGAGGTGAT        60

TCATGGAGAA ATAGAGAGAC TGAGTGTGAG TGAACATGAG TGAGAAAAAC TGGATTTGTG       120

TGGCATTTTC TGATAACGGT GTCCTTCTGT TTGCAGGTGT CCAGTGTCAG GTGCAGCTGG       180

TGGAGTCTGG GGGAGGCGTG GTCCAGCCTG GGAGGTCCCT GAGACTCTCC TGTGCAGCCT       240

CTGGATTCAC CTTCAGTAGC TATGGCATGC ACTGGGTCCG CCAGGCTCCA GGCAAGGGGC       300

TGGAGTGGGT GGCAGTTATA TCATATGATG GAAGTAATAA ATACTATGCA GACTCCGTGA       360

AGGGCCGATT CACCATCTCC AGAGACAATT CCAAGAACAC GCTGTATCTG CAAATGAACA       420

GCCTGAGAGC TGAGGACACG GCTGTGTATT ACTGTGCGAG AGACACAGTG AGGGGAAGTC       480

ATTGTGCGCC CAGACACAAA CCTCCCTGCA GG                                     512
```

(2) INFORMATION FOR SEQ ID NO: 31:

(i) SEQUENCE CHARACTERISTICS:
        (A) LENGTH: 631 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 31:

```
CATCCCTTTT CACCTGTCCA TAGAGAGGCA CCAGCCACAT GCAAATCTCA CTTAGGCACC        60

CACAGAAAAC CGCCACACAT TTCCTTAAAA TCAGGGTCCT GCTCACATGG GAAATACTTT       120

CTGAGAGTCC TGGACCTCCT GTGCGAGAAC ATGAAACACC TGTGGTTCTT CCTCCTGCTG       180

GTGGCAGCTC CCAGATGTGA GTGTCTCAAG GCTGCAGACA TGGAGATATG GGAGGTGCCT       240

CTGATCCCAG GGCTCACTGT GTGTCTCTCT GTTCACAGGG GTCCTGCCCC AGGTGCAGCT       300
```

```
GCAGGAGTCG GGCCCAGGAC TGGTGAAGCC TTCACAGACC CTGTCCCTCA CCTGTACTGT    360

CTCTGGTGGC TCCATCAGCA GTGGTGGTTA CTACTGGAGC TGGATCCGCC AGCACCCAGG    420

GAAGGGCCTG GAGTGGATTG GGTACATCTA TTACAGTGGG AGCACCTACT ACAACCCGTC    480

CCTCAAGAGT CGAGTTACCA TATCAGTAGA CACGTCTAAG AACCAGTTCT CCCTGAAGCT    540

GAGCTCTGTG ACTGCCGCGG ACACGGCCGT GTATTACTGT GCGAGAGACA CAGTGAGGGG    600

AGGTGAGTGT GAGCCCAGAC ACAAACCTCC C                                   631
```

(2) INFORMATION FOR SEQ ID NO: 32:

(i) SEQUENCE CHARACTERISTICS:
        (A) LENGTH: 341 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 32:

```
ACCAGTCTCC AGGCAAGGGG CTGGAGTGAG TAATAGATAT AAAAGATGAT GGAAGTCAGA     60

TACACCATGC AGACTCTGTG AAGGGCAGAT TCTCCATCTC CAAAGACAAT GCTAAGAACT    120

CTCTGTATCT GCAAATGAAC ACTCAGAGAG CTGAGGACGT GGCCGTGTAT GGCTATACAT    180

AAGGTCCCAA GTGAGGAAAT ATCGGTGTGA GTCCAGACAC AACATTTCCT GCAAAAAGAA    240

GAAAGGAGTC TGGGCCGAAG GGGACACTCA GCACTCACAA AACAGGTGCA GCCCCACGGC    300

AGGTGCAGAT GGAGGGAGGG TAAGGGCTGC TTTTCCTTCA G                        341
```

(2) INFORMATION FOR SEQ ID NO: 33:

(i) SEQUENCE CHARACTERISTICS:
        (A) LENGTH: 583 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 33:

```
TGAACACAGA GGACTCACCA TGGAGTTTGG GCTGAGCTGG GTTTTCCTCG TTGCTCTTTT     60

AAGAGGTGAT TCATTGGAGA AATAGAGAGA CTGAGTGTGA GTGAACATGA GTGAGAAAAA    120

CTGGATTTGT GTGGCATTTT CTGATAACGG TGTCCTTCTG TTTGCAGGTG TCCAGTGTCA    180

GGTACAGCTG GTGGAGTCTG GGGGAGGCGT GGTCCAGCCT GGGAGGTCCC TGAGACTCTC    240

CTGTGCAGCG TCTGGATTCA CCTTCAGTAG CTATGGCATG CACTGGGTCC GCCAGGCTCC    300

AGGCAAGGGG CTGGAGTGGG TGGCAGTTAT ATGGTATGAT GGAAGTAATA AATACTATGC    360

AGACTCCGCG AAGGGCCGAT TCACCATCTC CAGAGACAAT TCCACGAACA CGCTGTTTCT    420

GCAAATGAAC AGCCTGAGAG CCGAGGACAC GGCTGTGTAT TACTGTGCGA GAGACACAGT    480

GAGGGGAGGT CATTGTGCGC CCAGACACAA ACCTCCCTGC AGGAACGCTG GCGGGAAATC    540

AGCTGCAGGG GGGGCTCAGG AGCCACTGAT CAGAGTCAGC CCT                      583
```

(2) INFORMATION FOR SEQ ID NO: 34:

(i) SEQUENCE CHARACTERISTICS:
        (A) LENGTH: 687 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 34:

```
AAAAGACTGG GCCCTCCCTC ATCCCTTTTT ACCTATCCAT ACAAAGGCAC CACCCACATG    60

CAAATCCTCA CTTAGGCACC CACAGGAAAT GACTACACAT TTCCTTAAAT TCAGGGTCCA   120

GCTCACATGG AAGTGCTTT CTGAGAGTCA TGGACCTCCT GCACAAGAAC ATGAAACACC   180

TGTGGTTCTT CCTCCTCCTG GTGGCAGCTC CCAGATGTGA GTGTCTCAGG AATGCGGATA   240

TGAAGATATG AGATGCTGCC TCTGATCCCA GGGCTCACTG TGGGTTTCTC TGTTCACAGG   300

GGTCCTGTCC CAGGTGCAGC TACAACAGTG GGGCGCAGGA CTGTTGAAGC CTTCGGAGAC   360

CCTGTCCCTC ACCTGCGCTG TCTATGGTGG GTCCTTCAGT GGTTACTACT GGAGCTGGAT   420

CCGCCAGCCC CCAGGGAAGG GGCTGGAGTG GATTGGGGAA ATCAATCATA GTGGAAGCAC   480

CAACTACAAC CCGTCCCTCA AGAGTCGAGT CACCATATCA GTAGACACGT CCAAGAACCA   540

GTTCTCCCTG AAGCTGAGCT CTGTGACCGC CGCGGACACG GCTGTGTATT ACTGTGCGAG   600

AGGCACAGTG AGGGGAGGTG AGTGTGAGCC CAGACAAAAA CCTCCCTGCA GGTAGGCAGA   660

GGGGGCGGGC GCAGGTACTG CTCAAGA                                       687
```

(2) INFORMATION FOR SEQ ID NO: 35:

(i) SEQUENCE CHARACTERISTICS:
        (A) LENGTH: 700 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 35:

```
AAATAGGAGA CATNCAAATA GGCCCCCCCC TTTCCTGATA AAAAGCAGCC CAGTCCTGAC    60

CCTGCAGCCC TGGGAGAGAA GCACCAGCCC TGGGATTCTC AGGTGTTTCC ACTTTGTCAT   120

CAGCAACAAA CAAATTACCA TGGAATTTGG CCTGAGCTGG GTTTTCCTTG CTGCTATTTT   180

AAAAGGTGAT TCATGAAGAA CTAAGGATAT TGAGTGAGTG GACATGAGTG AGAGAAACAG   240

TGGATTTGTG TGGCAGTTTC TGACCAGGGT GTCTCTGTGT TTGCAGGTGT CCAGTGTGAG   300

GTGCAGCTGG TGGAGTCTGG GGGAGGCTTG GTACAGCCTG GGGGATCCCT GAGACTCTCC   360

TGTGCAGCCT CTGGATTCAC CTTCAGTAAC AGTGACATGA ACTGGGTCCA TCAGGCTCCA   420

GGAAAGGGGC TGGAGTGGGT ATCGGGTGTT AGTTGGAATG GCAGTAGGAC GCACTATGCA   480

GACTCTGTGA AGGGCCGATT CATCATCTCC AGAGACAATT CCAGGAACAC CCTGTATCTG   540
```

```
CAAACGAATA GCCTGAGGGC CGAGGACACG GCTGTGTATT ACTGTGTGAG AAACACTGTG    600

AGAGGTCGGA AGTGTGAGCC CAGACACAAA CCTCCTGCAG GAACGTTGGG GGAAATCAGC    660

TGCAGGGGGC GCTCAGGACC CACTCATCAG AGTCAACCCC                         700
```

(2) INFORMATION FOR SEQ ID NO: 36:

(i) SEQUENCE CHARACTERISTICS:
        (A) LENGTH: 806 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 36:

```
TGACACTAAC TCCCCCAGGA TCTCACATCT GCTCTGGANA CGGCTCTCCT GTTGTCCCTA     60

CCCCAGAGCT TGCTATAGAG GAGGAGACAT CCACATAGGG CCCTCNCTTG TCCTGATGAA    120

AACCAGCCTT GCCTGCGTCT ACGGGAGAAG AGCCCCAGTC CAGAAGTACC AGGGGTTTCC    180

ATTTGGTGGT CAGGTCTCTG AACACAGAGG ACTCACTATG GAGTTTGGGC TGAGCTGGGG    240

TTTCCATGTT GCTAATGTAA AAGGTGACTC ATGGAGAACT AGAGATATTG AGTGTGAGTG    300

GACACAAGTG AGAGAAACAG TGGATATGTG TGGCAGGTTC TGACCAGGGT GTCTGTGTGT    360

GTTTGCAGGT GTCCAGTGTG AGGTGCACCT GGTGGAGTCT TTGGGAGGCT TGTTATAGCC    420

TGGGGGTCCC TGAGACTTTC TTTTGCAGCC TCTGGATTCA CCTTTAGTAC CTTTATTAGG    480

TACTGGATGA GCTGGGTCCA TCAGGCTCCT GGGAAAGGGC TGGAGTAGGT CTCATTTATG    540

AGTTGTTGTG TAGGTAGCAC AAGCTATGCA GACTCTGTGA AGGGTCGATT CACCCTCTCC    600

AGAGATGATG CCAAGAAATC ACTGTATCTG CAAATGAACA GCGTCAGAGC CGAGGATAGG    660

TCTGTGTATT ACTGTGGTGG CATTGTGTGC ATCCCTTGTT TAGGTACATG CAGAGATGCT    720

GCTTTGGTGT GTTCAGGGGC TCCTGTTTTG GGGACACCAA TTTTGGAGTT TGCAGTATCC    780

TTGAGTCCAG TACGTTCATG GTGGCA                                        806
```

(2) INFORMATION FOR SEQ ID NO: 37:

(i) SEQUENCE CHARACTERISTICS:
        (A) LENGTH: 500 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 37:

```
GGAATCACCA TGTTGTTTGG ACTGAGCTGG CCGTTCCGAT TTACTATTTT AAGGGGTGAC     60

ACGTGAAGCA CTACAGATAT TGCTCGTGAG TGGATATTAG AGAAACAGTG GATATGTGTG    120

GCAGTTTCTG ACCAGGATGT CTCTGTGTTT ACAGGTGTGC AGTATGAGGT GCAGCTGGTA    180

GAGTCTGGGG GAGACTTGGT ACAGCTGTGG TGGGTCCTGA GACTCTCATG TGCAGCCTGT    240

GGATTCATCT TGAGAAGCAA CTGGTCCCAC CGGGCTTCAC GAAAGGGGCT GGCATGGAAT    300
```

| | | |
|---|---|---|
| GACATGGTCT CATACATTAG TGCTAGTGGT GGTAGTCTAT ACTATGCAGA CACTGAAGGG | 360 |
| TAGATTCACC ATCTCTAGAG ACAATGGCAA GAACATGCTG TTCTTGCAAA TGAACAGTCT | 420 |
| GAGAGATGAG GACTCGGTTG TGTTGAGAGA CATGGTGAGG GGAAAATCAG TATGAGCCCA | 480 |
| GCCAGAACTC TCCCTGCAGG | 500 |

(2) INFORMATION FOR SEQ ID NO: 38:

(i) SEQUENCE CHARACTERISTICS:
        (A) LENGTH: 507 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 38:

| | | |
|---|---|---|
| CAACTCATCA TGCAGTTTGT GCTGAGCTGG GTTTTCCTTG TTGGTATTTT AAAAGGTGAT | 60 |
| TCATGGAGAA CTACAGATGT TGAGTGTGAG TGGACATGAG TGAGCCAAAC AGTGGGTTTG | 120 |
| TGTGGCAGTT TCTGACCTGG TGTCTCTGTG TTTACAGGTG TCCAGTGTGA GGTGCAGCTG | 180 |
| GTGGAGTCTG GGGGAGGCTT GGTACAGCCT AGGGGGTCCC TGAGACTCTC CTGTGCAGCC | 240 |
| TCTGGATTCA CCGTCAGTAG CAATGAGATG AGCTGGATCC GCCAGGCTCC AGGGAAGGGG | 300 |
| CTGGAGTGGG TCTCATCCAT TAGTGGTGGT AGCACATACT ACGCAGACTC CAGGAAGGGC | 360 |
| AGATTCACCA TCTCCAGAGA CAATTCCAAG AACACGCTGT ATCTTCAAAT GAACAACCTG | 420 |
| AGAGCTGAGG GCACGGCCGC GTATTACTGT GCCAGATATA CACAGAGGGG AAGTCATTGT | 480 |
| GCGCCCAGAC ACAAACCTCC CTGTAGG | 507 |

(2) INFORMATION FOR SEQ ID NO: 39:

(i) SEQUENCE CHARACTERISTICS:
        (A) LENGTH: 800 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 39:

| | | |
|---|---|---|
| AGAAGAGGAC TCTGGGCTTG GAGAGGGGAG CCCCCCAAGA AGAGAAACTT GATTCTCCAA | 60 |
| AGGGCACAGC CAGCATTCTC CTCCCAGGGT GAGCTCCAAA AGACTGGCGC CTCTCTCATC | 120 |
| CCTTTTCACT GCTCCGTACA AACGCACNCA CCCCCATGCA AATCCTCACT TAGGCGCCCA | 180 |
| CAGGAAGCCA CCACACATTT CCTTAAATTC AGGTCCAACT CATAAGGGAA ATGCTTTCTG | 240 |
| AGAGTCATGG ATCTCATGTG CAAGAAAATG AAGCACCTGT GGTTCTTCCT CCTGCTGGTG | 300 |
| GCGGCTCCCA GATGTGAGTG TTTCTAGGAT GCAGACATGG AGATATGGGA GGCTGCCTCT | 360 |
| GATCCCAGGG CTCACTGTGG GTTTTTCTGT TCACAGGGGT CCTGTCCCAG CTGCAGCTGC | 420 |
| AGGAGTCGGG CCCAGGACTG GTGAAGCCTT CGGAGACCCT GTCCCTCACC TGCACTGTCT | 480 |

```
CTGGTGGCTC CATCAGCAGT AGTAGTTACT ACTGGGGCTG GATCCGCCAG CCCCCAGGGA      540

AGGGGCTGGA GTGGATTGGG AGTATCTATT ATAGTGGGAG CACCTACTAC AACCCGTCCC      600

TCAAGAGTCG AGTCACCATA TCCGTAGACA CGTCCAAGAA CCAGTTCTCC CTGAAGCTGA      660

GCTCTGTGAC CGCCGCAGAC ACGGCTGTGT ATTACTGTGC GAGACACACA GTGAGGGGAG      720

GTGAGTGTGA GCCCAGACAA AAACCTCCCT GCAGGGAGGC TGAGGGGGCG GTCGCAGGTG      780

CAGCTCAGNG CCAGCAGGGG                                                 800
```

(2) INFORMATION FOR SEQ ID NO: 40:

(i) SEQUENCE CHARACTERISTICS:
        (A) LENGTH: 970 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 40:

```
CACAACCTCC ATGAAAAACA ACATAGAAAT TTCTCAAAGA ACTAAAATTA GAATTACCAT       60

TTCTTCCAGT AAGCTGTCCC AGTAGGCATG TTCCTCCCAA ACTTTTATNT CAGAGAATGT      120

TGCCTGCACT CATATGTTTA TTTCAACACC ATTTTCAATA GAAAAGTCAA ATAATCTAAG      180

TGTCAATCAG TGGATGATTA GATAAAATAT GATATNNATG TAAATCATNG GAATACTATG      240

CAGCCAGTAT GGTATGAATT CAGTNGTGAN NCCNAGCCCC TGGACAAGNN GGCTTGAGTG      300

GATGGGATGG ATCATCACCT ACACTGGGAA CCCAACATAT ACCAACGGCT TCACAGGACG      360

GGTTTCTATT CTCCATGGGA CACCTCTGTC AGCATGGCGT ATCTGAAGAT CAGCAGCCTA      420

AAGGCTGAGG ACACGGCCGC GTATGACTGT ATGAGAGACA CAGGGTGGAA ACCCACATCC      480

CGAGGGAGTC AGAAACCCCG GGGAGGAGC CACCTGTTCT GACCTGAGNC AGTGGTCCAA       540

NCAGTNTCTT TAACNTCCAT ATGATCTCAT TTTTGCATCA TCTTCTACTT TTATATTAGC      600

TAAGAACTTG GGGTAGACAG GTGCTCCTAA GAGATCCTTA ACTTGCCCAT TTTGATGGGT      660

TTTCCAGAAG ACGTGAGAAG CCACTTTGTT ANCAAAGCAT CCCAAATCCA TGCCCTGTTN      720

CTAGATACAT GTGAGCCCAT TTCCTGGTCT TTGCTTAACT GACAAGCTCT CATCAGTGCA      780

CCTGGGCTAA TTTCACATCA GGTAGAGGAA CGCGTTATAA AGGAAAGCTA ATGTTGTAAT      840

AGCAATTCCT GCTTAAAAAC CTTCAGCTTC ATTGTTTTTG TGTAATCCAT CANCAAATTA      900

TGTTAGTTCA AGGTTCTCAA TGGGAGTTTC TAATAAATAG AAAGGATGTA TAAAGCTTGN      960

CACTGNCCGT                                                            970
```

(2) INFORMATION FOR SEQ ID NO: 41:

(i) SEQUENCE CHARACTERISTICS:
        (A) LENGTH: 819 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 41:

```
CCCCACTCTC TCCTCAGNCG TCCCATCCCA GAGCTTGGCA TTGTAGTAGG AGACATCCAA      60

ATAGAGCCCT CCCTCTGCTT ATGAAAACCA GCCCAGCCCT GACCCTGCAG CTGTGGGAGA     120

GGAGCCCCAG CCCTGGGATT TTCAGGTGCT TTCATTTTGT GATCAGGACT GAACACAGAG     180

GATTCACCAT GGAGTCATGG CTGAGCTGGG TTTTTCTTGC CGCTATTTTA AAAGGTAATT     240

CATTGAGAAC TATTGAAATT GAGTGTGAGT GGATAAGAGT GAGATAAACA GTGGATACGT     300

GTGGCAGTTT CTGACCAGGG TTTCTTTGTG TTTGCAGGTG TCCAGTGTGA GGTGCAGCTG     360

GTGGAGTCTG GGGGAGGCTT GGTCCAGCCT GGGGGGTCCC TGAGACTCTC CTGTGCAGCC     420

TCAGGATTCT CCTTTAGTAG CTATGGCATG AGCTGGGTCC GCCAGGCTCC AGGGAAGGGG     480

CTGGAGTGAG TGGCACATAT CTGGAATGAT GGAAGTCAGA AATACTATGC AGACTCTGTG     540

AAGGGCCGAT TCACAATCTC CGAGACAATT CTAAGAGCAT GCTCTATCTG CAAATGGACA     600

GTCTGAAAGC TAAGGACACG GCCATGTATT ACTGTACCAG ACACAGTGAG AGGAAGTCCG     660

TGTGAGCCCA GACACAAACC TCCCTGCAGG GGCACGCGGG GCCACCAGAG GGTGCCCAGG     720

ATCCCCTGAA GACAGGGACA GNCCAAAGGC AGGTGCAGAT GGNTGTCAAG AGGGTCTTGT     780

GGCTTCGTCT ACATCTAACT GGTTTCCTGG GTGAGCCTC                           819
```

(2) INFORMATION FOR SEQ ID NO: 42:

(i) SEQUENCE CHARACTERISTICS:
        (A) LENGTH: 471 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 42:

```
TTGTAGGTGA TTTATGGAGA ATGAGAGATG TTGAGTGCGA GTGGACATGA GTGAGAGAAA      60

CAGTAGATAT GTGTGCCCGT TTCTGACCAG GGTGTCTCTG TGTTTGCAGG CGTCCAGCGT     120

GAGGCGCAGC TGGTGGAGTC TGGGGGAGAC TTGGTACAAC CTGGGTGGGT CCCCGAGACT     180

CTCATTTGCA GCTTCTAGAT TCACCTTCAG TGACTTCTGA ATGCACTGGA TCCGCCAGGC     240

TTCTGGGAAA GGGCTGGAGT GGGTTGGCCG TATTAGAACC AAACGTAACA GTTACACGAC     300

AGAATGCGCT GCATCTGTGA AAGGCAGGTT CACCATCTCA AGAGATGATT CAAAGAACAC     360

ACTGTATCTG CAAGTGAATA CCCTGAAAAC CGAGTACACG GCCATCTATT ACTGTACTAG     420

AGACAGTGAG GGGGAGGTTA ACGTAGGCCC ATACACAAAT CTCCCTGCAG G             471
```

(2) INFORMATION FOR SEQ ID NO: 43:

(i) SEQUENCE CHARACTERISTICS:
        (A) LENGTH: 870 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast (H) CELL LINE: CGM1

(xi) SEQUENCE DESCRIPTION: SEQ ID NO: 43:

```
CATCTGTTAC AGAACTCATT ATATAGTAGG AGACATCCAA ATNGGGTCCC TCCCTCTGCT      60
GATGAAAACC AGCCCAGCCC TGACCCTGCA GCTCTGGGAG AGGAGCCCCA GCCCTGAGAT     120
TCCCAGGTGT TTCCATTCGG TGATCAGCAC TGAACACAGA GAACGCACCA TGGAGTTTGG     180
ACTGAGCTGG GTTTTCCTTG TTGCTATTTT AAAAGGTGAT TCATGGATAA ATAGAGATGT     240
TGAGTGTGAG TGAACATGAG TGAGAGAAAC AGTGGATATG TGTGGCAGTG TCTGACCAGG     300
GTGTCTCTGT GTTTGCAGGT GTCCAGTGTG AAGTGCAGCT GGTGGAGTCT GGGGGAGTCG     360
TGGTACAGCC TGGGGGGTCC CTGAGACTCT CCTGTGCAGC CTCTGGATTC ACCTTTGATG     420
ATTATACCAT GCACTGGGTC CGTCAAGCTC CGGGGAAGGG TCTGGAGTGG GTCTCTCTTA     480
TTAGTTGGGA TGGTGGTAGC ACATACTATG CAGACTCTGT GAAGGGCCGA TTCACCATCT     540
CCAGAGACAA CAGCAAAAAC TCCCTGTATC TGCAAATGAA CAGTCTGAGA CTGAGGACA      600
CCGCCTTGTA TTACTGTGCA AAAGATACAC AGTGAGGGGA AGTCAGCGAG AGCCCAGACA     660
AAAACCTCGC TGCAGGAAGA CAGGAGGGGC CTGGGCTGCA GAGGCCACTC AAGACACACT     720
GAGCATAGGG TTAACTCTGG GACAAGTTGC TCAGGAAGGT TAAGAGCTGG TTTCCTTTCA     780
GAGTCTTCAC AAATTTCTCC ATCTAACAGT TTCCCCAGGA ACCNGTCTAG ATCTGTGATC     840
TTGGATCTGC TGAAACTGCC TGTGTCACCT                                     870
```

(2) INFORMATION FOR SEQ ID NO: 44:

(i) SEQUENCE CHARACTERISTICS:
        (A) LENGTH: 529 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 44:

```
TCCCCGGGTA CCGAGCTCAA GTGCCAGGAT TCCCAGGTGT TTCACTTGG TGATCAGAAC       60
TTAACACAGA GGACTCACCA TGTTGTTTGG GCTGAGCTGG GCTTTCCTTG TTACTATTTT     120
AAGAGGTGAT TCATGAAGAA CTACAGATAT TGTTTGTGAG TGGATATTAG AGAAACAGTG     180
GATATGTGTG GCAGTTGCTG ACCAGGATTT CTCTGTGTTT GCAGGTGTGC AGTATGAGGT     240
GCAGCTGGTA GAGTCTTTTT TTTTTTTTTT TTTTCACTTT TTAGCGAACA TCCATGGGTT     300
ACAAAATAAT GGGTTGGCTT TTCTTCCAAC ACTTTACAGA CACCATCAAT TTTCCCCTTG     360
CTTATAAGGT TTTTAACCAG AAGAATGCTG TCATCATCTT TCCTGTTCTT TTAGGAAGAA     420
TGCCCCCTCA ACTCATCTCC ACTTGTCTGC ATGTATTTCT ATTTGTCTTG GACGTTCCCA     480
ACAGCCTCNC GAACACTCAC CTCACCCTAC AATGCTGCTC GAGGGGGTC                529
```

(2) INFORMATION FOR SEQ ID NO: 45:

(i) SEQUENCE CHARACTERISTICS:
        (A) LENGTH: 748 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
    (A) ORGANISM: Homo sapiens
    (G) CELL TYPE: human lymphoblast
    (H) CELL LINE: CGM1

(xi) SEQUENCE DESCRIPTION: SEQ ID NO: 45:

```
CAGGATCAGG GCTTGAGTCA TCAGCATCTC ACTCTTGCAA AGNCTGATGT GTCGTTTGTC      60
TTCCCTTTCT TATCATCGAC CAGGCTTTGA GCTATGAAAT GCCCTGTCTC ATCAATATNC     120
AAATAACCTG AGATCGACTG AGGTAAATAT GGATATGTCT GTGCCCTGAG AGCATCACCC     180
AACAAACCAC ATCCCTCCTC TAGAGAATCC CCTGAAAGCA CAGCTCCTCA CCATGGACTG     240
GACCTGGAGA ATCCTCTTCT TGGTGGCAGC AGCCACAGGT AAGGGGCTCC CAAGTCCCAG     300
TGATGAGGAG GGGATTGAGT CCAGTCAAGG TGGCTTTTAT CCACTCCTGT GTCCCCTCCA     360
CAGATGCCTA CTCCCAGATG CAGCTGGTGC AGTCTGGGGC TGAGGTGAAG AAGACTGGGT     420
CCTCAGTGAA GGTTTCCTGC AAGGCTTCCG GATACACCTT CACCTACCGC TACCTGCACT     480
GGGTGCGACA GGCCCCCGGA CAAGCGCTTG AGTGGATGGG ATGGATCACA CCTTTCAATG     540
GTAACACCAA CTACGCACAG AAATTCCAGG ACAGAGTCAC CATTACCAGG GACAGGTCTA     600
TGAGCACAGC CTACATGGAG CTGAGCAGCC TGAGATCTGA GGACACAGCC ATGTATTACT     660
GTGCAAGATA CACAGTGTGA AAACCCACAT CCTGAGACCG TCAGAAACCC CAAGGAGGAG     720
GCAGCTTCAC TGAATGAGGA GGTTACAG                                        748
```

(2) INFORMATION FOR SEQ ID NO: 46:

(i) SEQUENCE CHARACTERISTICS:
        (A) LENGTH: 799 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 46:

```
CATTTCTTCA AAGCAGGATT AGGGCTTGGA CCATCAGCAT CCCACTCCTG TGTGGCAGAT      60
GGGACATCTA TCTTCTTTCT CCAACCTCGA TCAGGCTTTT GAGGTATGAA ATAATCTGTC     120
TCATGAATAT GCAAATAACC TTAGATCTAC TGAGGTAAAT ATGGATACAT CTGGGCCCTG     180
AAAGCATCAT CCAACAACCA CATCCCTTCT CTACAGAAGC CTCTGAGAGG AAAGTTCTTC     240
ACCATGGACT GGACCTGGAG GGTCTTCTGC TTGCTGGCTG TAGCTCCAGG TAAAGGGCCA     300
ACTGGTTCCA GGGCTGAGGA AGGGATTTTT TCCAGTTTAG AGGACTGTCA TTCTCTACTG     360
TGTCCTCTCC GCAGGTGCTC ACTCCCAGGT GCAGCTGGTG CAGTCTGGGC TGAGGTGAA      420
GAAGCCTGGG GCCTCAGTGA AGGTTTCCTG CAAGGCATCT GGATACACCT TCACCAGCTA     480
CTATATGCAC TGGGTGCGAC AGGCCCCTGG ACAAGGGCTT GAGTGGATGG GAATAATCAA     540
CCCTAGTGGT GGTAGCACAA GCTACGCACA GAAGTTCCAG GCAGAGTCA CCATGACCAG      600
GGACACGTCC ACGAGCACAG TCTACATGGA GCTGAGCAGC CTGAGATCTG AGGACACGGC     660
CGTGTATTAC TGTGCGAGAG ACACAGTGTG AGAACCCACA TCCTCAGAGT GTCAGAAACC     720
CTGAGGGAGG AGTCAGCTGT GCTGAGCTGA GAAAATGACA GGGGTTATTC AGTTTAAGAC     780
```

```
TGTTTAGAAA ACGGGTTAT                                                    799

(2) INFORMATION FOR SEQ ID NO: 47:

(i) SEQUENCE CHARACTERISTICS:
        (A) LENGTH: 627 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 47:

CCAAATAAAC ACATTAAATG TCAAGATACG CCCAAAAACT TATCTGCCTG ACCCCCTAGT         60

TGTCTCCGTA ATTTTTGGAT GAAAACCAGC CCACCCCTGA CCCTGCTGCT CTGGGAGAGG        120

AGCCCCAGCC TTGGGATTCC CAAGTGTTTG CATTCAGTGA TCAGGACTGA ACACACAGGA        180

CTCACCAGGG AGTTTGTGCT AAGCTGGGTT TTCCTTGTTG CTATATTAAA ATGTGATTCA        240

TGGAGAACTA GAGAGATTGA GTGTGAGTTA CATGAGTGAG AGAAACAGTG GATATGTTTG        300

GCAATTTCTG ACTTTTGTGT CTCTGTGTTT GCAGGTGTCC AGTGTGAGGA TCAGCTGGTG        360

GAGTCTGGGG GAGGCTTGGT ACAGCCTGGG GGGTCCCTGA GACCCTCCTG TGCAGCCTCT        420

GGATTCGCCT TCAGTAGCTA TGTTCTGCAC TGGGTTCGCC GGGCTCCAGG GAAGGGTCCG        480

GAGTGGGTAT CAGCTATTGG TACTGGTGGT GATACATACT ATGCAGACTC CGTGATGGGC        540

CGATTCACCA TCTCCAGAGA CAACGCCAAG AAGTCCTTGT ATCTCAAATG AACAGCCTGA        600

TAGCTGAGGA CATGGCTGTG TATTATG                                           627

(2) INFORMATION FOR SEQ ID NO: 48:

(i) SEQUENCE CHARACTERISTICS:
        (A) LENGTH: 743 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 48:

AAGGGTCCCC ACCCTAGAGC TTGCTATATA GTAGGAGATA TCCAAATAGG NCCCTCCCTC         60

TACTGATGAA AACCCAACCC AACCCTGACC CTGCAGCTCT CAGAGAGGTG CCTTAGCCCT        120

GGATTCCAAG GCATTTCCAC TTGGTGATCA GCACTGAACA CAGAGGACTC ACCATGGAGT        180

TGGGGCTGTG CTGGGTTTTC CTTGTTGCTA TTTTAGAAGG TGATTCATGG AAAACTAGAG        240

AGATTTAGTG TGTGTGGATA TGAGTGAGAG AAACAGTGGA TATGTGTGGC AGTTTCTGAC        300

CTTGGTGTCT CTTTGTTTGC AGGTGTCCAG TGTGAGGTGC AGCTGGTGGA GTCTGGGGGA        360

GGCTTGGTAC AGCCTGGGGG GTCCCTGAGA CTCTCCTGTG CAGCCTCTGG ATTCACCTTC        420

AGTAGCTATA GCATGAACTG GGTCCGCCAG GCTCCAGGGA AGGGGCTGGA GTGGGTTTCA        480

TACATTAGTA GTAGTAGTAG TACCATATAC TACGCAGACT CTGTGAAGGG CCGATTCACC        540

ATCTCCAGAG ACAATGCCAA GAACTCACTG TATCTGCAAA TGAACAGCCT GAGAGCCGAG        600
```

```
GACACGGCTG TGTATTACTG TGCGAGAGAC ACAGTGAGGG GAGGTCAGTG TGACACCAGA        660

CACAAACCTC CCTGCAGGGG TCCGCAGGAC CACCAGGGGG CGACAGGACA CTGAGCACGG        720

GGCTGTCTCC AGGGCAGGTG CAG                                               743
```

(2) INFORMATION FOR SEQ ID NO: 49:

(i) SEQUENCE CHARACTERISTICS:
        (A) LENGTH: 763 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 49:

```
TCACCCAACT CCTCCAGGCA CAGTCATCTT ATCTGGCCCC GTCCTCTCCT CAGNTGTCCC         60

ACCCCAGAGC TTGGTATATA GTAGGAGACA TNCAAATAAG GCCCTCCCTC TGCTGATGAA        120

AATGAGCCCA GCCCTGACCC TGCAGCTCTG GGAGAGGAGC CCCANCCGTG AGATTCCCAG        180

GAGTTTCCAC TTGGTGATCA GCACTGAACA CAGACCACCA ACCATGGAGT TTGGGCTTAG        240

CTGGGTTTTC CTTGTTGCTA TTTTAAAAGG TAATTCATGG TGTACTAGAG ATACTGAGTG        300

TGAGGGGACA TGAGTGGTAG AAACAGTGGA TATGTGTGGC AGTTTCTGAC CTTGGTGTTT        360

CTGTGTTTGC AGGTGTCCAA TGTGAGGTGC AGCTGGTGGA GTCTGGGGGA GGCTTGGTAC        420

AGCCAGGGCG GTCCCTGAGA CTCTCCTGTA CAGCTTCTGG ATTCACCTTT GGTGATTATG        480

CTATGAGCTG GTTCCGCCAG GCTCCAGGGA AGGGGCTGGA GTGGGTAGGT TTCATTAGAA        540

GCAAAGCTTA TGGTGGGACA ACAGAATACA CCGCGTCTGT GAAAGGCAGA TTCACCATCT        600

CAAGAGATGG TTCCAAAAGC ATCGCCTATC TGCAAATGAA CAGCCTGAAA ACCGAGGACA        660

CAGCCGTGTA TTACTGTACT AGAGACACAG TGNGGGGAGG TCAATGTGAG CCCAGACACA        720

GACCTCCCTG CAGGCCCGCA CAGAGCCACC AGGGGCGCT AGG                          763
```

(2) INFORMATION FOR SEQ ID NO: 50:

(i) SEQUENCE CHARACTERISTICS:
        (A) LENGTH: 283 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 50:

```
TGGCTCACCA TGGAGTTAGG GCTGAGCTGG GTTTCCCTTG TCATTATATT AAAAGGCGAA         60

TAATGGAGAA CTTGAGATAT GGAGTGTGAG TGGATATGAG TGAAGAAACA GTGATTCTGT        120

GTGGCAGGTT CTGACTCAGA TGTCCTCTGT GCTTGTAGGT GTCTAGTGTG GGGTGCAGAT        180

GGTGGAGTCT TGGGGAGAGT TGGCACAAAN CTGAATGTGCC TGAGACTCTG CCGTGCATCC        240

TCTGAATCCA CCTTCTGTAG CTACTAGATC AGCTGAATCT GCC                         283
```

(2) INFORMATION FOR SEQ ID NO: 51:

(i) SEQUENCE CHARACTERISTICS:
        (A) LENGTH: 700 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 51:

```
AGGTTCTGGG TTATAAACNC TGTAGACTCC TCCCTTCAGG GCAGGNTGAC CAACTATGCA    60

AATGCAAGTG GGGGCCTCCC CACTTAAACC CAGGGCTCCC CTCCACAGTG AGTCTCCCTC   120

ACTGCCCAGC TGGGATCTCA GGGCTTCATT TTCTGTCCTC CACCATCATG GGGTCAACCG   180

CCATCCTCGC CCTCCTCCTG GCTGTTCTCC AAGGTCAGTC CTGCCGAGGG CTTGAGGTCA   240

CAGAGGAGAA CGGGTGGAAA GGAGCCCCTG ATTCAAATTT TGTGTCTCCC CCACAGGAGT   300

CTGTTCCGAG GTGCAGCTGG TGCAGTCTGG AGCAGAGGTG AAAAAGCCCG GGGAGTCTCT   360

GAAGATCTCC TGTAAGGGTT CTGGATACAG CTTTACCAGC TACTGGATCG CTGGGTGCG    420

CCAGATGCCC GGGAAAGGCC TGGAGTGGAT GGGGATCATC TATCCTGGTG ACTCTGATAC   480

CAGATACAGC CCGTCCTTCC AAGGCCAGGT CACCATCTCA GCCGACAAGT CCATCAGCAC   540

CGCCTACCTG CAGTGGAGCA GCCTGAAGGC CTCGGACACC GCCATGTATT ACTGTGCGAG   600

ACACACAGTG AGAGAAACCA GCCCCGAGCC CGTCTAAAAC CCTCCACACC GCAGGTGCAG   660

AATGAGCTGC TAGAGACTCA CTCCCCAGGG GCCTCTCTAT                        700
```

(2) INFORMATION FOR SEQ ID NO: 52:

(i) SEQUENCE CHARACTERISTICS:
        (A) LENGTH: 767 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 52:

```
ACACTCACCT GCTCTGGGCT CCTCCAAACT CTCCTCAGGA TTCCCCACCC CAGAGCTTGC    60

TATATAGTAG GAGACATCCA AACAAGAGCC NAAACCTCTG CTGATGAAAA GCAGCCCAGC   120

CCTGACCCTG CAGCTCTGGG AGAGGAGCCC CAGCTCCAGG ATTCCCAGGT CTTTCCATTT   180

AGTCTTCAGG GCTGAGCACA GAGGACTCAC CATGGAGTCT GGGCTGAGCT GGGTTTTCCT   240

TGTTGCTATT TTGAAAGGTG ATTCATGGGG AATGAGTTGA ATGTAAGTGA ATATGAGTGA   300

GAGAAACAGT GGATGTGTGC GGCAGTTTCT GACCAGGGTG TCTCTGTGTT TGCAGGTGTC   360

CAGTGTGAGG TGCAGCTGGT GGAGTCTGGG TGAGGCTTGG TACAGCCTGG AGGGTCCCTG   420

AGACTCTCCT GTGCAGCCTC TGGATTCACC TTCAGTAGCT CCTGGATGCA CTGGGTCTGC   480

CAGGCTCCGG AGAAGGGGCT GGAGTGGGTG GCCGACATAA AGTGTGACGG AAGTGAGAAA   540

TACTATGTAG ACTCTGTGAA GGGCCGATTG ACCATCTCCA GAGACAATGC CAAGAACTCC   600
```

| | |
|---|---|
| CTCTATCTGC AAGTGAACAG CCTGAGAGCT GAGGACATGA CCGTGTATTA CTGTGTGAGA | 660 |
| GGCACAGTGA GGGGAGGTCA GTGTGAGCCC AGACACAAAC CTCCTGCAGG GGCATCTGGA | 720 |
| GCCACAAGGG GGCGCTCAGG ATACACAGAG GGACAGGGGC AGCCCCA | 767 |

(2) INFORMATION FOR SEQ ID NO: 53:

(i) SEQUENCE CHARACTERISTICS:
        (A) LENGTH: 724 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 53:

| | |
|---|---|
| CCATTCGGTG ATCAGCACTG AACACAGAGG ACTCACCATG GAGTTTTGGC TGAGCTGGGT | 60 |
| TTTCCTTGTT GCTATTTTAA AAGGTGATTC ATGGAGAACT AGAGATATTG AGTGTGAGTG | 120 |
| AACACGAGTG AGAGAAACAG TGGATATGTG TGGCAGTTTC TAACCAATGT CTCTGTGTTT | 180 |
| GCAGGTGTCC AGTGTGAGGT GCAGCTGGTG GAGTCTGGAG GAGGCTTGAT CCAGCCTGGG | 240 |
| GGGTCCCTGA GACTCTCCTG TGCAGCCTCT GGGTTCACCG TCAGTAGCAA CTACATGAGC | 300 |
| TGGGTCCGCC AGGCTCCAGG GAAGGGGCTG GAGTGGGTCT CAGTTATTTA TAGCGGTGGT | 360 |
| AGCACATACT ACGCAGACTC CGTGAAGGGC CGATTCACCA TCTCCAGAGA CAATTCCAAG | 420 |
| AACACGCTGT ATCTTCAAAT GAACAGCCTG AGAGCCGAGG ACACGGCCGT GTATTACTGT | 480 |
| GCGAGAGACA CAGTGAGGGG AAGTCATTGT GCGCCCAGAC ACAAACCTCC CTGCAGGAAC | 540 |
| GCTGGGGGA AATCAGCGGN AGGGGGCGCT CAGGAGCCAC TGATCAGAGT CAGCCCCGGA | 600 |
| GGCAGGTGCA GATGGAGGCT GATTTCCTTG TCAGGATGTG GGACTTTTG TCTTCTTCTG | 660 |
| ACGGGTTCCC CAGGGGAACC TCTCTAAGTT TAGCATTCTG TGCCTATGAA CGTCTTCTCT | 720 |
| AAGT | 724 |

(2) INFORMATION FOR SEQ ID NO: 54:

(i) SEQUENCE CHARACTERISTICS:
        (A) LENGTH: 706 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 54:

| | |
|---|---|
| CTTGCTATAC AGTAGGAGAC ATGCNAATAG GTTTCTCCCT CTGCTGATGA CCAGTCCTGA | 60 |
| CCCCATAGCT CTGGGAGAGA AGCGCCAGCC CTGGGATTCC CAGGGGTTTC CATTTGGTGA | 120 |
| TCAGGACTAA AGACAGAGGA CCCACCATGG AGCTTGGGCT GAGCTGGGTT TTCACTGTTA | 180 |
| CTGTTTTAAA AGGTGAACTA GAGAGATTGA GTGTGAATGG ATACACTTGA GAGAAACAGT | 240 |
| GGATATGTCT GGAACTTTCT GACCAGGACA CCTACAAGTT TGCAGGTGTC CAGTGTGAGG | 300 |

```
TACAGCTGGT GGAGTCTGAA GAAAACCAAA GACAACTTGG GGGATCCCTG AGACTCTCCT    360

GTGCAGACTC TGGATTAACC TTCAGTAGCT ACTGAATGAG CTCAGATTCC CAAGCTCCAG    420

GGAAGGGGCT GGAGTGAGTA GTAGATATAT AGTAGGATAG AAGTCAGCTA TGTTATGCAC    480

AATCTGTGAA GAGCAGATTC ACCATCTCCA AAGAAAATGC CAAGAACTCA CTCTGTTTGC    540

AAATGAACAG TCTGAGAGCA GAGGGCACGG CCGTGTATTA CTGTATGTGA GTCACCAGGT    600

AAGAAGACAT CAGTGTGATC ACAGACACAG AATTTCCTGA ATAAGGGAG GAGTCTGGGC    660

TAAAAGGGCA CTCAGGACCC ACAGAAAACA GCGGAAGCTC TAGGGC                  706
```

(2) INFORMATION FOR SEQ ID NO: 55:

(i) SEQUENCE CHARACTERISTICS:
        (A) LENGTH: 800 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 55:

```
GGAAGAGANC TTGATTCTCA AGAGGGCACA GCCAGCTTCC TACTCCCAGG GCAAGCCCCA     60

AAAGACTGGG NCCTCCCTCC TCCCTTTTCA CCTGTCCATA CAAAGTCACC GCCCACATGC    120

AAATCCTCAC TTAGGCACCT ACAGGAAACC AGCACACATT TCCTTAAATT TGGGATCCAG    180

CTCACATGGG AAATACTTTC TGAGACTCAT GGGCCTCCTG CACAAGAACA TGAAACACCT    240

GTGGTTCTTC CTCCTGCTGG TGGCAGCTCC CAGATGTGAG TGCCTCAGGG ATCCAGACCT    300

GAAGATATGA GATGCTGCCT CTCATCCCAG GGCTCACCGT GGTTCTCTCT GTTCACAGGG    360

GTCCTGTCCC AGGTGCAGCT GCAGGAGTCG GGCCCAGGAC TGGTGAAGCC TTCGGAGACC    420

CTGTCCCTCA TCTGCGCTGT CTCTGGTGAC TCCATCAGCA GTGGTAACTG GTGAATCTGG    480

GTCCGCCAGC CCCCAGGGAA GGGGCTGGAG TGGATTGGGG AAATCCATCA TAGTGGGAGC    540

ACCTACTACA ACCCGTCCCT CAAGAGTCGA ATCACCATGT CCGTAGACAC GTCAAGAAC    600

CAGTTCTACC TGAAGCTGAG CTCTGTGACC GCCGCGGACA CGGCCGTGTA TTACTGTGCG    660

AGATACACAG TGAGGGGAGG TGAGTGTGAG CCCAGACACA AACCTCCCTA CAGATAGGCA    720

GAGGGGGNGG GCACAGGTGC TGCTCAGGAN CAACAGGGGG CGCGCGANGN CACAGAGCCC    780

GAGGNCCGGG TCANGAGCAG                                                800
```

(2) INFORMATION FOR SEQ ID NO: 56:

(i) SEQUENCE CHARACTERISTICS:
        (A) LENGTH: 429 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 56:

```
AGGAATTGGG CTATTCAATG CATCCTTCGT GAATATGCAA ATCACTAAGG TTAATACAGA     60
```

| | |
|---|---:|
| TATCTCTGTG CCGTGAGAGC ATCACCCAAC AACCACACCC CTCCTTGGAG AATCCCTAGA | 120 |
| TCACAGCTCC TCACCATGGA CTGGACCTGG AGCATCCTCT TCTTGGTGGC AGCAGCAACA | 180 |
| GGTAAGGACT CCCCAGTCCC AGGGCTGAGG GAGAAACCAG GCCAGTCATG TGAGACTTCA | 240 |
| CCCACTGCTG TCTCCTCTCC ACAGGTGCCC ACTCCCGAGT GCAGCTGGTG CAGTCTGGGC | 300 |
| CTGAGGTGAA GCAGCCTGGG GCCTCGGCGA AGGTCTCCTG CAAGGTGTCT GGTTAAACTG | 360 |
| TCATCACCTA TGGTATGAAT TGGATACGAC AGACCCCAGG ACAGGGCTT GAGTGGATGG | 420 |
| GATGGATCC | 429 |

(2) INFORMATION FOR SEQ ID NO: 57:

(i) SEQUENCE CHARACTERISTICS:
        (A) LENGTH: 462 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 57:

| | |
|---|---:|
| CATCAGTTGC GCTCAGGAGT TTTAGAACAG CCTGGCAACA CATTTAGATC TGGGCTTCCC | 60 |
| TTCTCATCAC CCTCAATATT AGTGTCCCTT GTGAATCAGG TCCAGCTGCG GCTGTTCCAC | 120 |
| ATGGGCCGT TCTTCCATTT CCTCAGTGTT TGCAGAAGTC CTGTGTGAAG TTTATTGATG | 180 |
| GAGTCAGAGG CAGAAAATTG TACAGCCCAG TGGTTCACTG AGACTCTCCT GCAAAGGCTC | 240 |
| TGATTTCACC TTTACTGGCT ACAGCATGAG CTTGGTCCAG CAGGCTTCAT GACAGGGATT | 300 |
| GGTGTGGGTG GAAACAGTGA GTAGTCAAGT GGGAGTTCTC AGAGTTACTC TCCATGAGTA | 360 |
| CAAATAAATT AACAGTCCCA AGCGACACCT TTTCATGTGC AGTCTACCTT ACAATGACCA | 420 |
| ACCTGAAAGT CCAAGGACAA GGCTGTGTAT TACTGTGAGG GA | 462 |

(2) INFORMATION FOR SEQ ID NO: 58:

(i) SEQUENCE CHARACTERISTICS:
        (A) LENGTH: 629 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 58:

| | |
|---|---:|
| AGGGTCTTCA GCTATGAAAT GCTCTGACTC ATGAATATGC AAATAACCTG AGATGCACTG | 60 |
| AGGTAAATAT GGATATTTGT CAGCCCTGAG AGCATCATCC AGAAACCACA TCCCTCCGCT | 120 |
| AGAGAAGCCC TGACGGCACA GTTCCTCACT ATGGACTGGA TTTGGAGGAT CCTCTTCTTG | 180 |
| GTGGGAGCAG CGACAGGCAA GGAGATGCCA AGTCCCAGTG ATGAGGAGGG GATTGAGTCC | 240 |
| AGTCAAGGTG GCTTTCATCC ACTCCTGTGT TCTCTCCACA GGTGCCCACT CCCAAAATGCA | 300 |
| GCTGGTGCAG TCTGGGCCTG AGGTGAAGAA GCCTGGGACC TCAGTGAAGG TCTCCTGCAA | 360 |

```
GGCTTCTGGA TTCACCTTTA CTAGCTCTGC TGTGCAGTGG GTGCGACAGG CTCGTGGACA    420

ACGCCTTGAG TGGATAGGAT GGATCGTCGT TGGCAGTGGT AACACAAACT ACGCACAGAA    480

GTTCCAGGAA AGAGTCACCA TTACCAGGGA CATGTCCACA AGCACAGCCT ACATGGAGCT    540

GAGCAGCCTG AGATCCGAGG ACACGGCCGT GTATTACTGT GCGGCAGACA CAGTGTGAAA    600

ACCCACATCC TGAGAGTGTC AGAAACGCC                                      629

(2) INFORMATION FOR SEQ ID NO: 59:

(i) SEQUENCE CHARACTERISTICS:
        (A) LENGTH: 622 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 59:

CCTCCTTTTT CACCTCTCCA TACAAAGGCA CCACCCACAT GCAAATCCTC ACTTAAGCAC     60

CCACAGGAAA CCACCACACA TTTCCTTAAA TTCAGGTTCC AGCTCACATG GAAATACTT    120

TCTGAGAGCT CTGGACCTCC TGTGCAAGAA CATGAAACAT CTGTGGTTCT TCCTTCTCCT    180

GGTGGCAGCT CCCAGATGTG AGTATCTCAG GGATCCAGAC ATGGGGATAT GGGAGGTGCC    240

TCTGATCCCA GGGCTCACTG TGGGTCTCTC TGTTCACAGG GGTCCTGTCC CAGGTGCAGC    300

TGCAGGAGTC GGGCCCAGGA CTGGTGAAGC CTTCGGAGAC CCTGTCCCTC ACCTGCACTG    360

TCTCTGGTGG CTCCGTCAGT AGTTACTACT GGAGCTGGAT CCGGCAGCCC CCAGGGAAGG    420

GACTGGAGTG GATTGGGTAT ATCTATTACA GTGGGAGCAC CAACTACAAC CCCTCCCTCA    480

AGAGTCGAGT CACCATATCA GTAGACACGT CCAAGAACCA GTTCTCCCTG AAGCTGAGCT    540

CTGTGACCGC TGCGGACACG GCCGTGTATT ACTGTGCGAG AGACACAGTG AGGGGAGGTG    600

AGTGTGAGCC CAGACAAAAA CC                                            622

(2) INFORMATION FOR SEQ ID NO: 60:

(i) SEQUENCE CHARACTERISTICS:
        (A) LENGTH: 588 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 60:

CCCGGGATTC CCAGCTGTCT CCACTTGGTC ATGAACACTG AACACAGAAG ACACACCATG     60

GAGTCTGGGC TGAGCTGGAT TTTCCTTGTT GCAGTTTTAA AAGGTGATTT ATGGAGAATA    120

GACACACTGA GTGTGACTGG ACATAAGTGA GAGAAACAGT GGATTTGTGT GGCAGTTTCT    180

GACCAGGGTG TCTCCGTGTT TGCAGGTGTC CAGTGTGAGG TGCAGCTGGT GGAGTCTGGG    240

GGAGGCTTAG TAAAGACTGG GGGGTCTCTG AGACTCTCCT GTGCAGCCTC TGGATTCACC    300

TTCAGTAGCT CTGCTATGCA CTGGGTCCAC CAGGCTCCAG GAAAGGGTTT GGAGTGGGTC    360
```

```
TCAGTTATTA GTACAAGTGG TGATACCGTA CTCTACACAG ACTCTGTGAA GGGCTGATTC        420

ACCATCTCTA GAGACAATGC CCAGAATTCA CTGTATCTGC AAATGAACAG CCTGAGAGCC        480

GACGACATGG CTGTGTATTA CTGTGTGAAA GACGCAGTGA GAAGTCAGTG TGAGCCCAGA        540

CACAAACCTC CTGCAGGGTA CCTGGGACAA CCAGGGAAAG CCTGGGAC                     588

(2) INFORMATION FOR SEQ ID NO: 61:

(i) SEQUENCE CHARACTERISTICS:
        (A) LENGTH: 1212 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
         (A) ORGANISM: Homo sapiens
         (G) CELL TYPE: human lymphoblast
         (H) CELL LINE: CGM1

(xi) SEQUENCE DESCRIPTION: SEQ ID NO: 61:

CCTCCTTTTT CACCTCTCCG TACAAAGGCA CCACCCACAT GCAAATCCTT ACTTAAGCAC         60

CCACAGGAAA CCACCACACA TTTCCTTAAA TTCAGGTTCC AGCTCACATG GGAAATACTT        120

TCTGAGAGCC TGGACCTCCT GTGCAAGAAC ATGAAACACC TGTGGTTCTT CCTCCTCCTG        180

GTGGCAGCTC CCAGATGTGA GTGTCTCAGG GATCCAGACA TGGGGGTATG GGAGGTGCCT        240

CTGATCCCAG GGCTCACTGT GGGTCTCTCT GTTCACAGGG GTCCTGTCCC AGGTGCAGCT        300

GCAGGAGTCG GGCCCAGGAC TGGTGAAGCC TTCGGAGACC CTGTCCCTCA CCTGCACTGT        360

CTCTGGTGGC TCCGTCAGCA GTGGTAGTTA CTACTGGAGC TGGATCCGGC AGCCCCCAGG        420

GAAGGGACTG GAGTGGATTG GGTATATCTA TTACAGTGGG AGCACCAACT ACAACCCCTC        480

CCTCAAGAGT CGAGTCACCA TATCAGTAGA CACGTCCAAG AACCAGTTCT CCCTGAAGCT        540

GAGCTCTGTG ACCGCTGCGG ACACGGCCGT GTATTACTGT GCGAGAGACA CAGTGAGGGG        600

AGGTGAGTGT GAGCCCAGGA CACAAACCTC CCTCATGGAC GCGGAGGGGA CCGGCGCAGG        660

TGCTGCTCAG GACCAGCAGG TGGCGCGCGG GGCCCCCAGA GCATGAGGCC GGGTCAGGAC        720

AGGTGCAGGG AGGGCTTCCT CATCTGCTCA CTGGTCTCCG TCCTCGCCAG CACCTCGCTG        780

TCACCAGGGC TCCTCTTTCT TTATTATCTG TGGTTCTGCT TCCTCACATT CTTGTGCCAG        840

GAAAGAAACG AGGAAGACGG GTTTTCGTCT ATAGTTGAAG CTTTTACTAG GATCTTGCCT        900

ACAAGTTCCT GCATGACCCA TTATAACTTA TCGATTAAAA AATATATATT CTAATGCTTC        960

TCACCATCTC TTGATTTGTA TCATCAACTG AATTGTACCC TCTTTGAAAT TCATATGATG       1020

AAACCTTAAA TTCAATGGAT CTATATTGGA ATTTTAATGA AATAATTAAG GTTAAATGTG       1080

GTCATAATTG TAAGACCCTA ATGCAATAGA CGTGTTGTCT TTATAAGAAG AGGAAGAGAC       1140

ACCAGAGACC TCTCACTTTT CACGTGCAGG CAGAGAAGAG GCCATGTGGA GACATAGTGC       1200

ACTAGAAGGT GG                                                          1212

(2) INFORMATION FOR SEQ ID NO: 62:

(i) SEQUENCE CHARACTERISTICS:
        (A) LENGTH: 560 base pairs
        (B) TYPE: nucleic acid
        (C) STRANDEDNESS: double
        (D) TOPOLOGY: linear (ii) MOLECULE TYPE: Genomic DNA
```

(vi) ORIGINAL SOURCE:
    (A) ORGANISM: Homo sapiens
    (G) CELL TYPE: human lymphoblast
    (H) CELL LINE: CGM1

(xi) SEQUENCE DESCRIPTION: SEQ ID NO: 62:

| | | | | | |
|---|---|---|---|---|---|
| GATCAGCACT | GAACACAGAG | GACTCACCAT | GGAGTTTGGG | CTGAGCTGGG | TTTTCCTTGT | 60
| TGCTAATTTA | AGAGGTGATT | CATAGATAAA | TAGAGATGTT | GAGTGGGAGT | GGACATGAGT | 120
| GAGAGAAACA | GTGGATGTGT | GTGGCAGTTT | CTGACCTTGG | TGTCTTTGTG | TTTGCAGGTG | 180
| TCCAGTGTGA | GGTGCAGCTG | GTGGAGTCTG | GGAAGGCTT | GGTCCAGCCT | GGGGGGTCCC | 240
| TGAGACTCTC | CTGTGCAGCC | TCTGGATTCA | CCTTCAGTAG | CTCTGCTATG | CACTGGGTCC | 300
| GCCAGGCTCC | AAGAAAGGGT | TTGTAGTGGG | TCTCAGTTAT | TAGTACAAGT | GGTGATACCG | 360
| TACTCTACAC | AGACTCTGTG | AAGGGCCGAT | TCACCATCTC | CAGAGACAAT | GCCCAGAATT | 420
| CACTGTCTCT | GCAAATGAAC | AGCCTGAGAG | CCGAGGGCAC | AGTTGTGTAC | TACTGTGTGA | 480
| AAGACGCAGT | GAGAAGTCAG | TGTGAGCCCA | GACACAAACC | TCCTGCAGGG | TACCTGGGAC | 540
| AATCAGGGAA | AGCCTGGGAC | | | | | 560

(2) INFORMATION FOR SEQ ID NO: 63:

(i) SEQUENCE CHARACTERISTICS:
        (A) LENGTH: 515 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 63:

| | | | | | |
|---|---|---|---|---|---|
| GAGCTCACTA | TGGGGTTTGA | GCTAACCAGA | ATTTTTCTTG | TTGCTATTTT | AAAAGGTGAC | 60
| TCATAGAGAA | ATAGAGTGAG | TGAGAGTGAG | TGGATATAAG | TGAGAAAAAC | AGTAGATGTG | 120
| TTTGGCAGTT | TCTGACCAGG | ACGTTTGTGT | ATTTTCAGGT | GTTCAGTGTG | AGGTGGAGCT | 180
| GATAGAGTCC | ATAGAGGGCC | TGAGACAACT | TGGGAAGTTC | CTGAGACTCT | CCTGTGTAGC | 240
| CTCTGGATTC | ACCTTCAGTA | GCTACTGAAT | GAGCTGGGTC | AATGAGACTC | TAGGGAAGGG | 300
| GCTGGAGGGA | GTAATAGATG | TAAAATATGA | TGGAAGTCAG | ATATACCATG | CAGACTCTGT | 360
| GAAGGGCAGA | TTCACCATCT | CCAAAGACAA | TGCTAAGAAC | TCACCGTATC | TCCAAACGAA | 420
| CAGTCTGAGA | GCTGAGGACA | TGACCATGCA | TGGCTGTACA | TAAGGTTCCA | AGTGAGGAAA | 480
| CATCGGTGTG | AGTCCAGACC | AAAATTTCCT | GCAGG | | | 515

(2) INFORMATION FOR SEQ ID NO: 64:

(i) SEQUENCE CHARACTERISTICS:
        (A) LENGTH: 649 base pairs
        (B) TYPE: nucleic acid
        (C) STRANDEDNESS: double
        (D) TOPOLOGY: linear (ii) MOLECULE TYPE: Genomic DNA (vi) ORIGINAL SOURCE:
        (A) ORGANISM: Homo sapiens
        (G) CELL TYPE: human lymphoblast
        (H) CELL LINE: CGM1

(xi) SEQUENCE DESCRIPTION: SEQ ID NO: 64:

| | | | | | |
|---|---|---|---|---|---|
| AGCTCTGGGA | GAGGAGCCCC | CCCCCTGGGA | TTCCCAGGTG | TTTTCATTTG | GTGATCAGCA | 60
| CTGAACACAG | AAGAGTCATG | ACGGAGTTTG | GGCTGAGCTG | GGTTTTCCTT | GTTGCTATTT | 120
| TTAAAGGTGA | TTCATGAGGA | AATAGAGATA | TTGAGTGTGA | GTGGACATGA | GTGAGAGAAA | 180
| CAGTGGATTT | GTGTGGCAGT | TTCTGACCTT | GGTGTCTCTG | TGTTTGCAGG | TGTCCAGTGT | 240
| GAGGTGCAGC | TGGTGGAGTC | TGGGGGAGGC | TTGGTCCAGC | CTGGGGGTC  | CCTGAGACTC | 300
| TCCTGTGCAG | CCTCTGGATT | CACCTTCAGT | AGCTATGCTA | TGCACTGGGT | CCGCCAGGCT | 360
| CCAGGGAAGG | GACTGGAATA | TGTTTCAGCT | ATTAGTAGTA | ATGGGGGTAG | CACATATTAT | 420
| GCAAACTCTG | TGAAGGGCAG | ATTCACCATC | TCCAGAGACA | ATTCCAAGAA | CACGCTGTAT | 480
| CTTCAAATGG | GCAGCCTGAG | AGCTGAGGAC | ATGGCTGTGT | ATTACTGTGC | GAGAGACACA | 540
| GTGAGGAGAA | GTTAATGTGG | GACCATGCAG | AAACCTCCCT | GCGGGAACGC | TGGGGAAAGT | 600
| CATCTGCAGG | GGGCGCTCAG | GAGCCACTGA | TCAGCGTCAA | CCGCAGCGG | | 649

(2) INFORMATION FOR SEQ ID NO: 65:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 65:

AGGTGCAGCT GGTGCAGTCT G                                          21

(2) INFORMATION FOR SEQ ID NO: 66:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 66:

CCAGGGGCCT GTCGCACCCA                                            20

(2) INFORMATION FOR SEQ ID NO: 67:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 67:

TGGGGCCTCA GTGAAGGTCT CCTG                                        24

(2) INFORMATION FOR SEQ ID NO: 68:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 68:

GATCCATCCC ATCCACTCAA G                                              21

(2) INFORMATION FOR SEQ ID NO: 69:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO: 69:

GATCCGTCCC ATCCACTCAA G                                              21

(2) INFORMATION FOR SEQ ID NO: 70:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO: 70:

TGTCTTCTCC ACAGGGTCT T                                               21

(2) INFORMATION FOR SEQ ID NO: 71:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO: 71:

GGGAAGGCCC TGGAGTGGCT                                                20

(2) INFORMATION FOR SEQ ID NO: 72:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO: 72:

GTGCAGGTCA GCGTGAGGGT                                                20

(2) INFORMATION FOR SEQ ID NO: 73:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO: 73:

```
TGGTTTTTGG AGGTGTCCTT GG                                                    22
```

(2) INFORMATION FOR SEQ ID NO: 74:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 74:

```
CACTCCAGCC CCTTCCCTGG AGC                                                   23
```

(2) INFORMATION FOR SEQ ID NO: 75:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 75:

```
GTGAGGTTCA GCTGGTGGAG T                                                     21
```

(2) INFORMATION FOR SEQ ID NO: 76:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 76:

```
AGCTGAACCT CACACTGGAC                                                       20
```

(2) INFORMATION FOR SEQ ID NO: 77:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 77:

```
AAGGGCCGAT TCACCATCT                                                        19
```

(2) INFORMATION FOR SEQ ID NO: 78:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 78:

```
TTGTCTCTGG AGATGGTGAA                                                       20
```

(2) INFORMATION FOR SEQ ID NO: 79:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (ii) MOLECULE TYPE: Genomic DNA (xi) SEQUENCE DESCRIPTION: SEQ ID NO: 79:

TGAGACTCTC CTGTGCAGCC TCTG                                      24

(2) INFORMATION FOR SEQ ID NO: 80:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 80:

TCTTTGTGTT TGCAGGTGT                                            19

(2) INFORMATION FOR SEQ ID NO: 81:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 81:

TCTCTGTGTT TGCAGGTGT                                            19

(2) INFORMATION FOR SEQ ID NO: 82:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 82:

TCTGTTCACA GGGGTCCTGT C                                         21

(2) INFORMATION FOR SEQ ID NO: 83:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO: 83:

TCCGGCAGCC CCCAGGGAA                                            19

(2) INFORMATION FOR SEQ ID NO: 84:

(i) SEQUENCE CHARACTERISTICS:
        (A) LENGTH: 18 base pairs
        (B) TYPE: nucleic acid

```
            (C) STRANDEDNESS: single
            (D) TOPOLOGY: linear (ii) MOLECULE TYPE: Genomic DNA (xi) SEQUENCE DESCRIPTION: SEQ ID NO: 84:

GCAGGTGAGG GACAGGGT                                                        18

(2) INFORMATION FOR SEQ ID NO: 85:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO: 85:

CAGGGAGAAC TGGTTCTTGG A                                                    21

(2) INFORMATION FOR SEQ ID NO: 86:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO: 86:

CCCGGGCATC TGGCGCACCC A                                                    21

(2) INFORMATION FOR SEQ ID NO: 87:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO: 87:

GCTGCTCCAC TGCAGGTAGG C                                                    21

(2) INFORMATION FOR SEQ ID NO: 88:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO: 88:

CTTCAGGCTG CTCCACTGCA G                                                    21

(2) INFORMATION FOR SEQ ID NO: 89:

(i) SEQUENCE CHARACTERISTICS:
            (A) LENGTH: 121 amino acids
            (B) TYPE: amino acid
            (D) TOPOLOGY: linear (ii) MOLECULE TYPE: protein
```

(xi) SEQUENCE DESCRIPTION: SEQ ID NO: 89:

Met Ser Val Ser Phe Leu Ile Phe Leu Pro Val Leu Gly Leu Pro Trp
1               5                   10                  15

Gly Val Leu Ser Gln Val Gln Leu Gln Gln Ser Gly Pro Gly Leu Val
                20                  25                  30

Lys Pro Ser Gln Thr Leu Ser Leu Thr Cys Ala Ile Ser Gly Asp Ser
            35                  40                  45

Val Ser Ser Asn Ser Ala Ala Trp Asn Trp Ile Arg Gln Ser Pro Ser
50                      55                  60

Arg Gly Leu Glu Trp Leu Gly Arg Thr Tyr Tyr Arg Ser Lys Trp Tyr
65                  70                  75                  80

Asn Asp Tyr Ala Val Ser Val Lys Ser Arg Ile Thr Ile Asn Pro Asp
                85                  90                  95

Thr Ser Lys Asn Gln Phe Ser Leu Gln Leu Asn Ser Val Thr Pro Glu
            100                 105                 110

Asp Thr Ala Val Tyr Tyr Cys Ala Arg
            115                 120

(2) INFORMATION FOR SEQ ID NO: 90:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO: 90:

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Gly Tyr Tyr Met His Trp Val Arg Gln Ala Pro Gly Gln Gly Leu
50                      55                  60

Glu Trp Met Gly Trp Ile Asn Pro Asn Ser Gly Gly Thr Asn Tyr Ala
65                  70                  75                  80

Gln Lys Phe Gln Gly Arg Val Thr Met Thr Arg Asp Thr Ser Ile Ser
                85                  90                  95

Thr Ala Tyr Met Glu Leu Ser Arg Leu Arg Ser Asp Asp Thr Ala Val
            100                 105                 110

Tyr Tyr Cys Ala Arg
            115

(2) INFORMATION FOR SEQ ID NO: 91:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO: 91:

Met Asp Trp Thr Trp Arg Ile Leu Phe Leu Val Ala Ala Ala Thr Gly
1               5                   10                  15

Val His Ser Gln Val Gln Leu Val Gln Ser Gly Ala Glu Val Lys Lys
                20                  25                  30

```
Pro Gly Ala Ser Val Lys Val Ser Cys Lys Ala Ser Gly Tyr Thr Phe
            35                  40                  45

Thr Ser Tyr Ala Met His Trp Val Arg Gln Ala Pro Gly Gln Arg Leu
 50                  55                  60

Glu Trp Met Gly Trp Ser Asn Ala Gly Asn Gly Asn Thr Lys Tyr Ser
 65                  70                  75                  80

Gln Glu Phe Gln Gly Arg Val Thr Ile Thr Arg Asp Thr Ser Ala Ser
                 85                  90                  95

Thr Ala Tyr Met Glu Leu Ser Ser Leu Arg Ser Glu Asp Met Ala Val
                100                 105                 110

Tyr Tyr Cys Ala Arg
            115
```

(2) INFORMATION FOR SEQ ID NO: 92:

(i) SEQUENCE CHARACTERISTICS:
        (A) LENGTH: 116 amino acids
        (B) TYPE: amino acid
        (D) TOPOLOGY: linear (ii) MOLECULE TYPE: protein (xi) SEQUENCE DESCRIPTION: SEQ ID NO: 92:

```
Met Lys His Leu Trp Phe Phe Leu Leu Leu Val Ala Ala Pro Arg Trp
 1               5                  10                  15

Val Leu Ser Gln Val Gln Leu Gln Glu Ser Gly Pro Gly Leu Val Lys
                20                  25                  30

Pro Ser Glu Thr Leu Ser Leu Thr Cys Thr Val Ser Gly Gly Ser Ile
            35                  40                  45

Ser Ser Tyr Tyr Trp Ser Trp Ile Arg Gln Pro Ala Gly Lys Gly Leu
 50                  55                  60

Glu Trp Ile Gly Arg Ile Tyr Thr Ser Gly Ser Thr Asn Tyr Asn Pro
 65                  70                  75                  80

Ser Leu Lys Ser Arg Val Thr Met Ser Val Asp Thr Ser Lys Asn Gln
                 85                  90                  95

Phe Ser Leu Lys Leu Ser Ser Val Thr Ala Ala Asp Thr Ala Val Tyr
                100                 105                 110

Tyr Cys Ala Arg
            115
```

(2) INFORMATION FOR SEQ ID NO: 93:

(i) SEQUENCE CHARACTERISTICS:
        (A) LENGTH: 119 amino acids
        (B) TYPE: amino acid
        (D) TOPOLOGY: linear (ii) MOLECULE TYPE: protein (xi) SEQUENCE DESCRIPTION: SEQ ID NO: 93:

```
Met Asp Thr Leu Cys Ser Thr Leu Leu Leu Thr Ile Pro Ser Trp
 1               5                  10                  15

Val Leu Ser Gln Ile Thr Leu Lys Glu Ser Gly Pro Thr Leu Val Lys
                20                  25                  30

Pro Thr Gln Thr Leu Thr Leu Thr Cys Thr Phe Ser Gly Phe Ser Leu
            35                  40                  45

Ser Thr Ser Gly Val Gly Val Gly Trp Ile Arg Gln Pro Pro Gly Lys
 50                  55                  60
```

```
Ala Leu Glu Trp Leu Ala Leu Ile Tyr Trp Asn Asp Asp Lys Arg Tyr
 65                  70                  75                  80

Ser Pro Ser Leu Lys Ser Arg Leu Thr Ile Thr Lys Asp Thr Ser Lys
                 85                  90                  95

Asn Gln Val Val Leu Thr Met Thr Asn Met Asp Pro Val Asp Thr Ala
                100                 105                 110

Thr Tyr Tyr Cys Ala His Arg
            115
```

(2) INFORMATION FOR SEQ ID NO: 94:

(i) SEQUENCE CHARACTERISTICS:
        (A) LENGTH: 112 amino acids
        (B) TYPE: amino acid
        (D) TOPOLOGY: linear (ii) MOLECULE TYPE: protein (xi) SEQUENCE DESCRIPTION: SEQ ID NO: 94:

```
Met Glu Leu Gly Leu Arg Trp Val Phe Leu Ala Ala Ile Leu Lys Gly
 1               5                  10                  15

Val Gln Cys Glu Met Gln Leu Val Glu Ser Gly Ala Asn Leu Thr Lys
                 20                  25                  30

Pro Gly Cys Pro Asp Ser Pro Val Gln Pro Leu Asp Ser Pro Ser Val
                 35                  40                  45

Ala Ile Ala Arg Thr Gly Ser Pro Arg Leu Gln Gly Arg Val Cys Ser
             50                  55                  60

Gly Ser Gln Leu Leu Val Val Val Val Pro Cys Thr Thr Gln Thr
 65                  70                  75                  80

Leu Arg Ala Asp Ser Pro Phe Pro Glu Thr Ile Pro Lys Thr His Cys
                 85                  90                  95

Ile Cys Lys Thr Asp Gly Gln Arg Met Gln Leu His Met Thr Leu Glu
                100                 105                 110
```

(2) INFORMATION FOR SEQ ID NO: 95:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO: 95:

```
Met Glu Leu Gly Leu Ser Trp Val Phe Leu Val Ala Ile Leu Glu Gly
 1               5                  10                  15

Val Gln Cys Glu Val Gln Leu Val Glu Ser Gly Gly Gly Leu Val Gln
                 20                  25                  30

Pro Gly Gly Ser Leu Arg Leu Ser Cys Ala Ala Ser Gly Phe Thr Phe
                 35                  40                  45

Ser Ser Tyr Trp Met Ser Trp Val Arg Gln Ala Pro Gly Lys Gly Leu
             50                  55                  60

Glu Trp Val Ala Asn Ile Lys Gln Asp Gly Ser Glu Lys Tyr Tyr Val
 65                  70                  75                  80

Asp Ser Val Lys Gly Arg Phe Thr Ile Ser Arg Asp Asn Ala Lys Asn
                 85                  90                  95

Ser Leu Tyr Leu Gln Met Asn Ser Leu Arg Ala Glu Asp Thr Ala Val
                100                 105                 110

Tyr Tyr Cys Ala Arg
```

115

(2) INFORMATION FOR SEQ ID NO: 96:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO: 96:

```
Met Asp Trp Thr Trp Arg Ile Leu Phe Leu Val Ala Ala Thr Ser
 1               5                  10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
            35                  40                  45

Thr Ser Tyr Asp Ile Asn Trp Val Arg Gln Ala Thr Gly Gln Gly Leu
        50                  55                  60

Glu Trp Met Gly Trp Met Asn Pro Asn Ser Gly Asn Thr Gly Tyr Ala
65                  70                  75                  80

Gln Lys Phe Gln Gly Arg Val Thr Met Thr Arg Asn Thr Ser Ile Ser
                85                  90                  95

Thr Ala Tyr Met Glu Leu Ser Ser Leu Arg Ser Glu Asp Thr Ala Val
            100                 105                 110

Tyr Tyr Cys Ala Arg
        115
```

(2) INFORMATION FOR SEQ ID NO: 97:

(i) SEQUENCE CHARACTERISTICS:
        (A) LENGTH: 118 amino acids
        (B) TYPE: amino acid
        (D) TOPOLOGY: linear (ii) MOLECULE TYPE: protein (xi) SEQUENCE DESCRIPTION: SEQ ID NO: 97:

```
Met Glu Leu Gly Leu Ser Trp Ile Phe Leu Leu Ala Ile Leu Lys Gly
 1               5                  10                  15

Val Gln Cys Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
            35                  40                  45

Asp Asp Tyr Ala Met His Trp Val Arg Gln Ala Pro Gly Lys Gly Leu
        50                  55                  60

Glu Trp Val Ser Gly Ile Ser Trp Asn Ser Gly Ser Ile Gly Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Leu
            100                 105                 110

Tyr Tyr Cys Ala Lys Asp
        115
```

(2) INFORMATION FOR SEQ ID NO: 98:

(i) SEQUENCE CHARACTERISTICS:
        (A) LENGTH: 111 amino acids (B) TYPE: amino acid
        (D) TOPOLOGY: linear (ii) MOLECULE TYPE: protein (xi) SEQUENCE DESCRIPTION: SEQ ID NO: 98:

Met Glu Leu Tyr Ser Thr Leu Leu Leu Thr Val Pro Ser Trp Val
1               5                   10                  15

Leu Ser Gln Val Thr Leu Lys Glu Ser Gly Pro Ala Leu Val Lys Pro
                20                  25                  30

Thr Gln Thr Leu Met Leu Thr Cys Thr Phe Ser Gly Phe Ser Leu Ser
            35                  40                  45

Thr Ser Gly Met Gly Val Gly Ile Cys Gln Pro Ser Ala Lys Ala Leu
    50                  55                  60

Glu Trp Leu Ala His Ile Tyr Asn Asp Asn Lys Tyr Tyr Ser Pro Ser
65                  70                  75                  80

Leu Lys Ser Arg Leu Ile Ile Ser Lys Asp Thr Ser Lys Asn Glu Val
                85                  90                  95

Val Leu Thr Val Ile Asn Met Asp Ile Val Asp Thr Ala Thr His
            100                 105                 110

(2) INFORMATION FOR SEQ ID NO: 99:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO: 99:

Met Glu Phe Gly Leu Ser Trp Val Phe Leu Val Ala Ile Ile Lys Gly
1               5                   10                  15

Val Gln Cys Gln Val Gln Leu Val Glu Ser Gly Gly Gly Leu Val Lys
                20                  25                  30

Pro Gly Gly Ser Leu Arg Leu Ser Cys Ala Ala Ser Gly Phe Thr Phe
            35                  40                  45

Ser Asp Tyr Tyr Met Ser Trp Ile Arg Gln Ala Pro Gly Lys Gly Leu
    50                  55                  60

Glu Trp Val Ser Tyr Ile Ser Ser Ser Gly Ser Thr Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg
        115

(2) INFORMATION FOR SEQ ID NO: 100:

(i) SEQUENCE CHARACTERISTICS:
        (A) LENGTH: 144 amino acids
        (B) TYPE: amino acid
        (D) TOPOLOGY: linear (ii) MOLECULE TYPE: protein (xi) SEQUENCE DESCRIPTION: SEQ ID NO: 100:

Met Xaa Trp Thr Tyr Lys Ile Leu Phe Leu Val Ala Ala Ala Thr Gly
1               5                   10                  15

```
Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
            35                  40                  45

Thr Tyr Cys Tyr Leu His Trp Val Gln Ala Pro Gly Gln Gly Leu Glu
            50                  55                  60

Trp Thr Gly Phe Leu Phe Glu Arg Phe Phe Ile Gln His Leu Phe Cys
 65                  70                  75                  80

Lys Gln Ile Ser Gly Ile Val Glu Ile Ile Leu Thr Asn Leu Thr Gln
                85                  90                  95

Asn Phe Leu Ile Asn Leu Cys Lys His Gln Phe Leu Asn Gln Cys Cys
            100                 105                 110

Xaa Tyr Phe Arg Thr Gln Ala Gln Xaa His Ile Xaa Thr Leu Leu Xaa
            115                 120                 125

Ser Leu Phe Lys Xaa Tyr Gln Lys Xaa Ser Ser Xaa Ala Cys Asn Val
    130                 135                 140

(2) INFORMATION FOR SEQ ID NO: 101:

(i) SEQUENCE CHARACTERISTICS:
         (A) LENGTH: 116 amino acids
         (B) TYPE: amino acid
         (D) TOPOLOGY: linear (ii) MOLECULE TYPE: protein (xi) SEQUENCE DESCRIPTION: SEQ ID NO: 101:

Met Glu Leu Gly Leu Ser Trp Val Phe Leu Val Ala Ile Leu Glu Gly
 1               5                   10                  15

Val Gln Cys Glu Val His Leu Val Glu Ser Gly Gly Leu Val Gln
            20                  25                  30

Pro Gly Gly Ala Leu Arg Leu Ser Cys Ala Ala Ser Gly Phe Thr Phe
            35                  40                  45

Ser Asn Tyr Asp Met His Trp Val Arg Gln Ala Thr Gly Lys Gly Leu
            50                  55                  60

Glu Trp Val Ser Ala Asn Gly Thr Ala Gly Asp Thr Tyr Tyr Pro Gly
 65                  70                  75                  80

Ser Val Lys Gly Arg Phe Thr Ile Ser Arg Glu Asn Ala Lys Asn Ser
                85                  90                  95

Leu Tyr Leu Gln Met Asn Ser Leu Arg Ala Gly Asp Thr Ala Val Tyr
            100                 105                 110

Tyr Cys Ala Arg
    115

(2) INFORMATION FOR SEQ ID NO: 102:

(i) SEQUENCE CHARACTERISTICS:
         (A) LENGTH: 119 amino acids
         (B) TYPE: amino acid
         (D) TOPOLOGY: linear (ii) MOLECULE TYPE: protein (xi) SEQUENCE DESCRIPTION: SEQ ID NO: 102:

Met Glu Phe Gly Leu Ser Trp Ile Phe Leu Pro Ala Ile Leu Lys Gly
 1               5                   10                  15

Val Gln Cys Glu Val Gln Leu Val Glu Ser Gly Gly Ala Leu Val Lys
            20                  25                  30

Pro Gly Gly Ser Leu Arg Leu Ser Cys Ala Ala Ser Gly Phe Thr Phe
```

```
                    35                  40                  45
Ser Asn Ala Trp Met Ser Trp Val Arg Gln Ala Pro Gly Lys Gly Leu
    50                  55                  60

Glu Trp Val Gly Arg Ile Lys Ser Lys Thr Asp Gly Thr Thr Asp
 65                 70                  75                  80

Tyr Ala Ala Pro Val Lys Gly Arg Phe Thr Ile Ser Arg Asp Asp Ser
                85                  90                  95

Lys Asn Thr Leu Tyr Leu Gln Met Asn Ser Leu Lys Thr Glu Asp Thr
               100                 105                 110

Ala Val Tyr Tyr Cys Thr Thr
               115

(2) INFORMATION FOR SEQ ID NO: 103:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO: 103:

Met Glu Phe Gly Leu Ser Trp Val Phe Leu Ala Gly Ile Leu Lys Gly
  1               5                  10                  15

Val Gln Cys Glu Val Gln Leu Val Glu Ser Gly Gly Gly Leu Val Gln
                20                  25                  30

Pro Gly Gly Ser Leu Arg Leu Ser Cys Ala Ala Ser Gly Phe Thr Phe
            35                  40                  45

Ser Asn Ser Asp Met Asn Trp Ala Arg Lys Ala Pro Gly Lys Gly Leu
    50                  55                  60

Glu Trp Val Ser Gly Val Ser Trp Asn Gly Ser Arg Thr His Tyr Val
 65                 70                  75                  80

Asp Ser Val Lys Arg Arg Phe Ile Ile Ser Arg Asp Asn Ser Arg Asn
                85                  90                  95

Ser Leu Tyr Leu Gln Lys Asn Arg Arg Arg Ala Glu Asp Met Ala Val
               100                 105                 110

Tyr Tyr Cys Val Arg
               115

(2) INFORMATION FOR SEQ ID NO: 104:

(i) SEQUENCE CHARACTERISTICS:
        (A) LENGTH: 116 amino acids
        (B) TYPE: amino acid
        (D) TOPOLOGY: linear (ii) MOLECULE TYPE: protein (xi) SEQUENCE DESCRIPTION: SEQ ID NO: 104:

Met Asp Cys Thr Trp Gly Ile Leu Phe Leu Val Ala Ser Xaa Thr Asp
  1               5                  10                  15

Val His Ser Gln Val Gln Leu Leu Gln Pro Gly Ala Glu Val Lys Lys
                20                  25                  30

Pro Ala Ser Ser Val Lys Val Ser Trp Pro Gly Phe Gln Ile His Leu
            35                  40                  45

His Gln Ile Leu Tyr Thr Val Gly Ala Thr Gly Pro Trp Thr Arg Ala
    50                  55                  60

Trp Leu Gly Cys Ile Asn Pro Tyr Asn Asp Asn Thr His Tyr Ala Gln
 65                 70                  75                  80
```

```
Lys Phe Arg Gly Arg Val Thr Ile Thr Ser Asp Arg Ser Val Ser Thr
                85                  90                  95

Ala Tyr Met Glu Leu Ser Ser Leu Arg Ser Glu Asp Met Val Val Tyr
            100                 105                 110

Ser Cys Val Arg
        115
```

(2) INFORMATION FOR SEQ ID NO: 105:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO: 105:

```
Met Asp Trp Thr Trp Ser Ile Leu Phe Leu Val Ala Ala Pro Thr Gly
 1               5                  10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
            35                  40                  45

Thr Ser Tyr Gly Ile Ser Trp Val Arg Gln Ala Pro Gly Gln Gly Leu
        50                  55                  60

Glu Trp Met Gly Trp Ile Ser Ala Tyr Asn Gly Asn Thr Asn Tyr Ala
65                  70                  75                  80

Gln Lys Leu Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg
        115
```

(2) INFORMATION FOR SEQ ID NO: 106:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO: 106:

```
Met Glu Phe Gly Leu Ser Trp Val Phe Leu Val Ala Ile Leu Lys Gly
 1               5                  10                  15

Val Gln Cys Glu Val Gln Leu Val Glu Ser Gly Gly Gly Val Val Arg
            20                  25                  30

Pro Gly Gly Ser Leu Arg Leu Ser Cys Ala Ala Ser Gly Phe Thr Phe
            35                  40                  45

Asp Asp Tyr Gly Met Ser Trp Val Arg Gln Ala Pro Gly Lys Gly Leu
        50                  55                  60

Glu Trp Val Ser Gly Ile Asn Trp Asn Gly Gly Ser Thr Gly Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Leu
            100                 105                 110
```

Tyr His Cys Ala Arg
    115

(2) INFORMATION FOR SEQ ID NO: 107:

(i) SEQUENCE CHARACTERISTICS:
       (A) LENGTH: 117 amino acids
       (B) TYPE: amino acid
       (D) TOPOLOGY: linear (ii) MOLECULE TYPE: protein (xi) SEQUENCE DESCRIPTION: SEQ ID NO: 107:

Met Glu Leu Gly Leu Arg Trp Val Phe Leu Val Ala Ile Leu Glu Gly
 1               5                  10                  15

Val Gln Cys Glu Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
            35                  40                  45

Ser Ser Tyr Ser Met Asn Trp Val Arg Gln Ala Pro Gly Lys Gly Leu
        50                  55                  60

Glu Trp Val Ser Ser Ile Ser Ser Ser Ser Tyr Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg
        115

(2) INFORMATION FOR SEQ ID NO: 108:

(i) SEQUENCE CHARACTERISTICS:
       (A) LENGTH: 118 amino acids
       (B) TYPE: amino acid
       (D) TOPOLOGY: linear (ii) MOLECULE TYPE: protein (xi) SEQUENCE DESCRIPTION: SEQ ID NO: 108:

Met Glu Ser Trp Leu Ser Trp Val Phe Leu Ala Ala Ile Leu Lys Gly
 1               5                  10                  15

Val Gln Cys Glu Val His Leu Val Glu Ser Gly Gly Ala Leu Val Gln
            20                  25                  30

Pro Gly Gly Ser Leu Arg Leu Ser Cys Ala Ala Ser Gly Phe Thr Phe
            35                  40                  45

Ser Tyr Tyr Tyr Met Ser Gly Val Arg Gln Ala Pro Gly Lys Gly Leu
        50                  55                  60

Glu Trp Val Gly Phe Ile Arg Asn Lys Ala Asn Gly Gly Thr Thr Glu
65                  70                  75                  80

Thr Thr Ser Val Lys Gly Arg Phe Thr Ile Ser Arg Asp Asp Ser Lys
                85                  90                  95

Ser Ile Thr Tyr Leu Gln Met Lys Ser Leu Lys Thr Glu Asp Thr Ala
            100                 105                 110

Val Tyr Tyr Cys Ser Arg
        115

(2) INFORMATION FOR SEQ ID NO: 109:

(i) SEQUENCE CHARACTERISTICS:

(A) LENGTH: 117 amino acids
(B) TYPE: amino acid
(D) TOPOLOGY: linear (ii) MOLECULE TYPE: protein (xi) SEQUENCE DESCRIPTION: SEQ ID NO: 109:

Met Glu Phe Gly Leu Ser Trp Leu Phe Leu Val Ala Lys Ile Lys Gly
 1               5                  10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Gly Lys Gly Leu
    50                  55                  60

Glu Trp Val Ser Ala Ile Ser Gly Ser Gly Gly Ser Thr Tyr Tyr Ala
 65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys
            115

(2) INFORMATION FOR SEQ ID NO: 110:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO: 110:

Met Asp Cys Thr Trp Arg Ile Leu Phe Leu Val Ala Ala Thr Gly
 1               5                  10                  15

Thr His Ala Gln Val Gln Leu Val Gln Ser Gly Ala Glu Val Lys Lys
            20                  25                  30

Pro Gly Ala Ser Val Lys Val Ser Cys Lys Val Ser Gly Tyr Thr Leu
        35                  40                  45

Thr Glu Leu Ser Met His Trp Val Arg Gln Ala Pro Gly Lys Gly Leu
    50                  55                  60

Glu Trp Met Gly Gly Phe Asp Pro Glu Asp Gly Thr Ile Tyr Ala
 65                  70                  75                  80

Gln Lys Phe Gln Gly Arg Val Thr Met Thr Glu Asp Thr Ser Thr Asp
                85                  90                  95

Thr Ala Tyr Met Glu Leu Ser Ser Leu Arg Ser Glu Asp Thr Ala Val
            100                 105                 110

Tyr Tyr Cys Ala Thr
            115

(2) INFORMATION FOR SEQ ID NO: 111:

(i) SEQUENCE CHARACTERISTICS:
        (A) LENGTH: 111 amino acids
        (B) TYPE: amino acid
        (D) TOPOLOGY: linear (ii) MOLECULE TYPE: protein (xi) SEQUENCE DESCRIPTION: SEQ ID NO: 111:

```
Trp Ser Leu Cys Ala Gly Phe Ser Leu Leu Phe Asn Val Ser Ser
 1               5                  10                  15

Val Arg Cys Ser Trp Trp Ser Leu Gly Glu Ala Cys Lys Ser Leu Arg
            20                  25                  30

Gly Pro Arg Asp Ser Pro Val Gln Pro Leu Asn Ser Pro Ser Val Ala
            35                  40                  45

Thr Thr Thr Val Ser Ala Arg Leu Gln Gly Met Gly Trp Ser Trp Phe
 50                  55                  60

Asp Lys Leu Ile Leu Met Gly Val Ala His Thr Ser Thr Pro Val Arg
 65                  70                  75                  80

Thr Asp Ser Ile Pro Pro Glu Ile Thr Pro Arg Thr His Phe Ile Cys
                85                  90                  95

Lys Thr Ala Lys Pro Arg Thr Arg Pro Ser Ile Ser Val Pro Glu
            100                 105                 110
```

(2) INFORMATION FOR SEQ ID NO: 112:

(i) SEQUENCE CHARACTERISTICS:
        (A) LENGTH: 119 amino acids
        (B) TYPE: amino acid
        (D) TOPOLOGY: linear (ii) MOLECULE TYPE: protein (xi) SEQUENCE DESCRIPTION: SEQ ID NO: 112:

```
Met Asp Thr Leu Cys Tyr Thr Leu Leu Leu Thr Thr Pro Ser Trp
 1               5                  10                  15

Val Leu Ser Gln Val Thr Leu Lys Glu Ser Gly Pro Val Leu Val Lys
            20                  25                  30

Pro Thr Glu Thr Leu Thr Leu Thr Cys Thr Val Ser Gly Phe Ser Leu
            35                  40                  45

Ser Asn Ala Arg Met Gly Val Ser Trp Ile Arg Gln Pro Pro Gly Lys
 50                  55                  60

Ala Leu Glu Trp Leu Ala His Ile Phe Ser Asn Asp Glu Lys Ser Tyr
 65                  70                  75                  80

Ser Thr Ser Leu Lys Ser Arg Leu Thr Ile Ser Lys Asp Thr Ser Lys
                85                  90                  95

Ser Gln Val Val Leu Thr Met Thr Asn Met Asp Pro Val Asp Thr Ala
            100                 105                 110

Thr Tyr Tyr Cys Ala Arg Ile
            115
```

(2) INFORMATION FOR SEQ ID NO: 113:

(i) SEQUENCE CHARACTERISTICS:
        (A) LENGTH: 112 amino acids
        (B) TYPE: amino acid
        (D) TOPOLOGY: linear (ii) MOLECULE TYPE: protein (xi) SEQUENCE DESCRIPTION: SEQ ID NO: 113:

```
Met Tyr Trp Thr Trp Arg Ile Leu Phe Leu Val Ala Ala Thr Gly
 1               5                  10                  15

Val His Ser Gln Val Gln Leu Val Gln Ser Gly Pro Glu Val Lys Lys
            20                  25                  30

Pro Gly Ala Ser Leu Lys Val Ser Cys Lys Ala Ser Gly Tyr Thr Phe
            35                  40                  45
```

-continued

```
Thr Ser Tyr Ala Ile Ser Trp Val Gln Ala His Gly Gln Gly Leu Glu
    50                  55                  60

Glu Met Gly Trp Ile Asn Thr Asn Thr Gly Asn Leu Thr Tyr Ala Gln
65                  70                  75                  80

Gly Phe Thr Gly Arg Phe Val Phe Ser Met Asp Thr Ser Val Ser Met
                85                  90                  95

Ala Tyr Leu His Ile Ser Ser Leu Lys Ala Glu Asp Thr Cys Lys Arg
                100                 105                 110
```

(2) INFORMATION FOR SEQ ID NO: 114:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO: 114:

```
Met Lys His Leu Trp Phe Phe Leu Leu Val Ala Ala Pro Arg Trp
1               5                   10                  15

Val Leu Ser Gln Val Gln Leu Gln Glu Ser Gly Pro Gly Leu Val Lys
                20                  25                  30

Pro Ser Asp Thr Leu Ser Leu Thr Cys Ala Val Ser Gly Tyr Ser Ile
                35                  40                  45

Ser Ser Ser Asn Trp Trp Gly Trp Ile Arg Gln Pro Pro Gly Lys Gly
    50                  55                  60

Leu Glu Trp Ile Gly Tyr Ile Tyr Tyr Ser Gly Ser Thr Tyr Tyr Asn
65                  70                  75                  80

Pro Ser Leu Lys Ser Arg Val Thr Met Ser Val Asp Thr Ser Lys Asn
                85                  90                  95

Gln Phe Ser Leu Lys Leu Ser Ser Val Thr Ala Val Asp Thr Ala Val
                100                 105                 110

Tyr Tyr Cys Ala Arg
            115
```

(2) INFORMATION FOR SEQ ID NO: 115:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO: 115:

```
Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
                20                  25                  30

Pro Gly Arg Ser Leu Arg Leu Ser Cys Ala Ala Ser Gly Phe Thr Phe
                35                  40                  45

Ser Ser Tyr Gly Met His Trp Val Arg Gln Ala Pro Gly Lys Gly Leu
    50                  55                  60

Glu Trp Val Ala Val Ile Ser Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
```

-continued

```
                100                 105                 110

Tyr Tyr Cys Ala Arg
        115

(2) INFORMATION FOR SEQ ID NO: 116:

(i) SEQUENCE CHARACTERISTICS:
        (A) LENGTH: 118 amino acids
        (B) TYPE: amino acid
        (D) TOPOLOGY: linear (ii) MOLECULE TYPE: protein (xi) SEQUENCE DESCRIPTION: SEQ ID NO: 116:

Met Lys His Leu Trp Phe Leu Leu Val Ala Ala Pro Arg Trp
  1               5                  10                  15

Val Leu Pro Gln Val Gln Leu Gln Glu Ser Gly Pro Gly Leu Val Lys
            20                  25                  30

Pro Ser Gln Thr Leu Ser Leu Thr Cys Thr Val Ser Gly Gly Ser Ile
        35                  40                  45

Ser Ser Gly Gly Tyr Tyr Trp Ser Trp Ile Arg Gln His Pro Gly Lys
    50                  55                  60

Gly Leu Glu Trp Ile Gly Tyr Ile Tyr Tyr Ser Gly Ser Thr Tyr Tyr
 65                  70                  75                  80

Asn Pro Ser Leu Lys Ser Arg Val Thr Ile Ser Val Asp Thr Ser Lys
                85                  90                  95

Asn Gln Phe Ser Leu Lys Leu Ser Ser Val Thr Ala Ala Asp Thr Ala
            100                 105                 110

Val Tyr Tyr Cys Ala Arg
        115

(2) INFORMATION FOR SEQ ID NO: 117:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO: 117:

Met Glu Phe Gly Leu Ser Trp Val Phe Leu Val Ala Leu Leu Arg Gly
  1               5                  10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Val Ile Trp Tyr Asp Gly Ser Asn Lys Tyr Tyr Ala
 65                  70                  75                  80

Asp Ser Ala Lys Gly Arg Phe Thr Ile Ser Arg Asp Asn Ser Thr Asn
                85                  90                  95

Thr Leu Phe Leu Gln Met Asn Ser Leu Arg Ala Glu Asp Thr Ala Val
            100                 105                 110

Tyr Tyr Cys Ala Arg
        115

(2) INFORMATION FOR SEQ ID NO: 118:
```

(i) SEQUENCE CHARACTERISTICS:
    (A) LENGTH: 116 amino acids
    (B) TYPE: amino acid
    (D) TOPOLOGY: linear (ii) MOLECULE TYPE: protein (xi) SEQUENCE DESCRIPTION: SEQ ID NO: 118:

Met Lys His Leu Trp Phe Phe Leu Leu Leu Val Ala Ala Pro Arg Trp
 1               5                  10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Ser Trp Ile Arg Gln Pro Pro Gly Lys Gly Leu
    50                  55                  60

Glu Trp Ile Gly Glu Ile Asn His Ser Gly Ser Thr Asn Tyr Asn Pro
65                  70                  75                  80

Ser Leu Lys Ser Arg Val Thr Ile Ser Val Asp Thr Ser Lys Asn Gln
            85                  90                  95

Phe Ser Leu Lys Leu Ser Ser Val Thr Ala Ala Asp Thr Ala Val Tyr
        100                 105                 110

Tyr Cys Ala Arg
    115

(2) INFORMATION FOR SEQ ID NO: 119:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO: 119:

Met Glu Phe Gly Leu Ser Trp Val Phe Leu Ala Ala Ile Leu Lys Gly
 1               5                  10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Ser Asp Met Asn Trp Val His Gln Ala Pro Gly Lys Gly Leu
    50                  55                  60

Glu Trp Val Ser Gly Val Ser Trp Asn Gly Ser Arg Thr His Tyr Ala
65                  70                  75                  80

Asp Ser Val Lys Gly Arg Phe Ile Ile Ser Arg Asp Asn Ser Arg Asn
            85                  90                  95

Thr Leu Tyr Leu Gln Thr Asn Ser Leu Arg Ala Glu Asp Thr Ala Val
        100                 105                 110

Tyr Tyr Cys Val Arg
    115

(2) INFORMATION FOR SEQ ID NO: 120:

(i) SEQUENCE CHARACTERISTICS:
        (A) LENGTH: 112 amino acids
        (B) TYPE: amino acid
        (D) TOPOLOGY: linear (ii) MOLECULE TYPE: protein (xi) SEQUENCE DESCRIPTION: SEQ ID NO: 120:

Met Glu Phe Gly Leu Ser Trp Gly Phe His Val Ala Asn Val Lys Gly
 1               5                  10                  15

Val Gln Cys Glu Val His Leu Val Glu Ser Leu Gly Leu Leu Pro
             20                  25                  30

Gly Gly Pro Asp Phe Leu Leu Gln Pro Leu Asp Ser Pro Leu Val Pro
             35                  40                  45

Leu Leu Gly Thr Gly Ala Gly Ser Ile Arg Leu Leu Gly Lys Gly Trp
 50                  55                  60

Ser Arg Ser His Leu Val Val Val Ala Gln Ala Met Gln Thr Leu
 65                  70                  75                  80

Arg Val Asp Ser Pro Ser Pro Glu Met Met Pro Arg Asn His Cys Ile
             85                  90                  95

Cys Lys Thr Ala Ser Glu Pro Arg Ile Gly Leu Cys Ile Thr Val Val
             100                 105                 110

(2) INFORMATION FOR SEQ ID NO: 121:

(i) SEQUENCE CHARACTERISTICS:
        (A) LENGTH: 111 amino acids
        (B) TYPE: amino acid
        (D) TOPOLOGY: linear (ii) MOLECULE TYPE: protein (xi) SEQUENCE DESCRIPTION: SEQ ID NO: 121:

Met Leu Phe Gly Leu Ser Trp Pro Phe Arg Phe Thr Ile Leu Arg Gly
 1               5                  10                  15

Val Gln Tyr Glu Val Gln Leu Val Glu Ser Gly Gly Asp Leu Val Gln
             20                  25                  30

Leu Trp Trp Val Leu Arg Leu Ser Cys Ala Ala Cys Gly Phe Ile Leu
             35                  40                  45

Arg Ser Asn Trp Ser His Arg Ala Ser Arg Lys Gly Leu Ala Trp Asn
 50                  55                  60

Asp Met Val Ser Tyr Ile Ser Ala Ser Gly Gly Ser Leu Tyr Tyr Ala
 65                  70                  75                  80

Asp Thr Glu Gly Ile His His Leu Arg Gln Trp Gln Glu His Ala Val
             85                  90                  95

Leu Ala Asn Glu Gln Ser Glu Arg Gly Leu Gly Cys Val Glu Arg
             100                 105                 110

(2) INFORMATION FOR SEQ ID NO: 122:

(i) SEQUENCE CHARACTERISTICS:
        (A) LENGTH: 115 amino acids
        (B) TYPE: amino acid
        (D) TOPOLOGY: linear (ii) MOLECULE TYPE: protein (xi) SEQUENCE DESCRIPTION: SEQ ID NO: 122:

Met Gln Phe Val Leu Ser Trp Val Phe Leu Val Gly Ile Leu Lys Gly
 1               5                  10                  15

Val Gln Cys Glu Val Gln Leu Val Glu Ser Gly Gly Gly Leu Val Gln
             20                  25                  30

Pro Arg Gly Ser Leu Arg Leu Ser Cys Ala Ala Ser Gly Phe Thr Val
             35                  40                  45

Ser Ser Asn Glu Met Ser Trp Ile Arg Gln Ala Pro Gly Lys Gly Leu

```
                    50                  55                  60
Glu Trp Val Ser Ser Ile Ser Gly Gly Ser Thr Tyr Tyr Ala Asp Ser
 65                  70                  75                  80

Arg Lys Gly Arg Phe Thr Ile Ser Arg Asp Asn Ser Lys Asn Thr Leu
                 85                  90                  95

Tyr Leu Gln Met Asn Asn Leu Arg Ala Glu Gly Thr Ala Ala Tyr Tyr
            100                 105                 110

Cys Ala Arg
        115

(2) INFORMATION FOR SEQ ID NO: 123:

(i) SEQUENCE CHARACTERISTICS:
        (A) LENGTH: 118 amino acids
        (B) TYPE: amino acid
        (D) TOPOLOGY: linear (ii) MOLECULE TYPE: protein (xi) SEQUENCE DESCRIPTION: SEQ ID NO: 123:

Met Lys His Leu Trp Phe Phe Leu Leu Leu Val Ala Ala Pro Arg Trp
 1                   5                  10                  15

Val Leu Ser Gln Leu Gln Leu Gln Glu Ser Gly Pro Gly Leu Val Lys
                 20                  25                  30

Pro Ser Glu Thr Leu Ser Leu Thr Cys Thr Val Ser Gly Gly Ser Ile
            35                  40                  45

Ser Ser Ser Tyr Tyr Trp Gly Trp Ile Arg Gln Pro Pro Gly Lys
 50                  55                  60

Gly Leu Glu Trp Ile Gly Ser Ile Tyr Tyr Ser Gly Ser Thr Tyr Tyr
 65                  70                  75                  80

Asn Pro Ser Leu Lys Ser Arg Val Thr Ile Ser Val Asp Thr Ser Lys
                 85                  90                  95

Asn Gln Phe Ser Leu Lys Leu Ser Ser Val Thr Ala Ala Asp Thr Ala
            100                 105                 110

Val Tyr Tyr Cys Ala Arg
            115

(2) INFORMATION FOR SEQ ID NO: 124:

(i) SEQUENCE CHARACTERISTICS:
        (A) LENGTH: 114 amino acids
        (B) TYPE: amino acid
        (D) TOPOLOGY: linear (ii) MOLECULE TYPE: protein (xi) SEQUENCE DESCRIPTION: SEQ ID NO: 124:

Met Glu Ser Trp Leu Ser Trp Val Phe Leu Ala Ala Ile Leu Lys Gly
 1                   5                  10                  15

Val Gln Cys Glu Val Gln Leu Val Glu Ser Gly Gly Gly Leu Val Gln
                 20                  25                  30

Pro Gly Gly Ser Leu Arg Leu Ser Cys Ala Ala Ser Gly Phe Ser Phe
            35                  40                  45

Ser Ser Tyr Gly Met Ser Trp Val Arg Gln Ala Pro Gly Lys Gly Leu
 50                  55                  60

Glu Val Ala His Ile Trp Asn Asp Gly Ser Gln Lys Tyr Tyr Ala Asp
 65                  70                  75                  80

Ser Val Lys Gly Arg Phe Thr Ile Ser Glu Thr Ile Leu Arg Ala Cys
                 85                  90                  95
```

```
Ser Ile Cys Lys Trp Thr Val Lys Leu Arg Thr Arg Pro Cys Ile Thr
            100                 105                 110
Val Pro (2) INFORMATION FOR SEQ ID NO: 125:

(i) SEQUENCE CHARACTERISTICS:
        (A) LENGTH: 118 amino acids
        (B) TYPE: amino acid
        (D) TOPOLOGY: linear (ii) MOLECULE TYPE: protein (xi) SEQUENCE DESCRIPTION: SEQ ID NO: 125:

Met Glu Phe Gly Leu Ser Trp Val Phe Leu Val Ala Ile Leu Lys Gly
  1               5                  10                  15

Val Gln Cys Glu Val Gln Leu Val Glu Ser Gly Gly Val Val Val Gln
                 20                  25                  30

Pro Gly Gly Ser Leu Arg Leu Ser Cys Ala Ala Ser Gly Phe Thr Phe
             35                  40                  45

Asp Asp Tyr Thr Met His Trp Val Arg Gln Ala Pro Gly Lys Gly Leu
 50                  55                  60

Glu Trp Val Ser Leu Ile Ser Trp Asp Gly Gly Ser Thr Tyr Tyr Ala
 65                  70                  75                  80

Asp Ser Val Lys Gly Arg Phe Thr Ile Ser Arg Asp Asn Ser Lys Asn
                 85                  90                  95

Ser Leu Tyr Leu Gln Met Asn Ser Leu Arg Thr Glu Asp Thr Ala Leu
            100                 105                 110

Tyr Tyr Cys Ala Lys Asp
            115

(2) INFORMATION FOR SEQ ID NO: 126:

(i) SEQUENCE CHARACTERISTICS:
        (A) LENGTH: 115 amino acids
        (B) TYPE: amino acid
        (D) TOPOLOGY: linear (ii) MOLECULE TYPE: protein (xi) SEQUENCE DESCRIPTION: SEQ ID NO: 126:

Met Leu Phe Gly Leu Ser Trp Ala Phe Leu Val Thr Ile Leu Arg Gly
  1               5                  10                  15

Val Gln Tyr Glu Val Gln Leu Val Glu Ser Phe Phe Phe Phe Phe Phe
                 20                  25                  30

His Phe Leu Ala Asn Ile His Gly Leu Gln Asn Asn Gly Leu Ala Phe
             35                  40                  45

Leu Pro Thr Leu Tyr Arg His His Gln Phe Ser Pro Cys Leu Gly Phe
 50                  55                  60

Pro Glu Glu Cys Cys His His Leu Ser Cys Ser Phe Arg Lys Asn Ala
 65                  70                  75                  80

Pro Ser Thr His Leu His Leu Ser Ala Cys Ile Ser Ile Cys Leu Gly
                 85                  90                  95

Arg Ser Gln Gln Pro Xaa Glu His Ser Pro His Pro Thr Met Leu Leu
            100                 105                 110

Glu Gly Val
        115
```

-continued (2) INFORMATION FOR SEQ ID NO: 127:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO: 127:

```
Met Asp Trp Thr Trp Arg Ile Leu Phe Leu Val Ala Ala Ala Thr Asp
 1               5                  10                  15

Ala Tyr Ser Gln Met Gln Leu Val Gln Ser Gly Ala Glu Val Lys Lys
             20                  25                  30

Thr Gly Ser Ser Val Lys Val Ser Cys Lys Ala Ser Gly Tyr Thr Phe
             35                  40                  45

Thr Tyr Arg Tyr Leu His Trp Val Arg Gln Ala Pro Gly Gln Ala Leu
         50                  55                  60

Glu Trp Met Gly Trp Ile Thr Pro Phe Asn Gly Asn Thr Asn Tyr Ala
65                  70                  75                  80

Gln Lys Phe Gln Asp Arg Val Thr Ile Thr Arg Asp Arg Ser Met Ser
                 85                  90                  95

Thr Ala Tyr Met Glu Leu Ser Ser Leu Arg Ser Glu Asp Thr Ala Met
            100                 105                 110

Tyr Tyr Cys Ala Arg
            115
```

(2) INFORMATION FOR SEQ ID NO: 128:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO: 128:

```
Met Asp Trp Thr Trp Arg Val Phe Cys Leu Leu Ala Val Ala Pro Gly
 1               5                  10                  15

Ala His Ser Gln Val Gln Leu Val Gln Ser Gly Ala Glu Val Lys Lys
             20                  25                  30

Pro Gly Ala Ser Val Lys Val Ser Cys Lys Ala Ser Gly Tyr Thr Phe
             35                  40                  45

Thr Ser Tyr Tyr Met His Trp Val Arg Gln Ala Pro Gly Gln Gly Leu
         50                  55                  60

Glu Trp Met Gly Ile Ile Asn Pro Ser Gly Gly Ser Thr Ser Tyr Ala
65                  70                  75                  80

Gln Lys Phe Gln Gly Arg Val Thr Met Thr Arg Asp Thr Ser Thr Ser
                 85                  90                  95

Thr Val Tyr Met Glu Leu Ser Ser Leu Arg Ser Glu Asp Thr Ala Val
            100                 105                 110

Tyr Tyr Cys Ala Arg
            115
```

(2) INFORMATION FOR SEQ ID NO: 129:

(i) SEQUENCE CHARACTERISTICS:
        (A) LENGTH: 110 amino acids
        (B) TYPE: amino acid
        (D) TOPOLOGY: linear (ii) MOLECULE TYPE: protein (xi) SEQUENCE DESCRIPTION: SEQ ID NO: 129:

Arg Glu Phe Val Leu Ser Trp Val Phe Leu Val Ala Ile Leu Lys Cys
  1               5                  10                  15

Val Gln Cys Glu Asp Gln Leu Val Glu Ser Gly Gly Leu Val Gln
             20                  25                  30

Pro Gly Gly Ser Leu Arg Pro Ser Cys Ala Ala Ser Gly Phe Ala Phe
         35                  40                  45

Ser Ser Tyr Val Leu His Trp Val Arg Arg Ala Pro Gly Lys Gly Pro
 50                  55                  60

Glu Trp Val Ser Ala Ile Gly Thr Gly Gly Asp Thr Tyr Tyr Ala Asp
 65                  70                  75                  80

Ser Val Met Gly Arg Phe Thr Ile Ser Arg Asp Asn Ala Lys Lys Ser
                 85                  90                  95

Leu Tyr Leu Lys Thr Ala Leu Arg Thr Trp Leu Cys Ile Met
            100                 105                 110

(2) INFORMATION FOR SEQ ID NO: 130:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO: 130:

Met Glu Leu Gly Leu Cys Trp Val Phe Leu Val Ala Ile Leu Glu Gly
  1               5                  10                  15

Val Gln Cys Glu Val Gln Leu Val Glu Ser Gly Gly Gly Leu Val Gln
             20                  25                  30

Pro Gly Gly Ser Leu Arg Leu Ser Cys Ala Ala Ser Gly Phe Thr Phe
         35                  40                  45

Ser Ser Tyr Ser Met Asn Trp Val Arg Gln Ala Pro Gly Lys Gly Leu
 50                  55                  60

Glu Trp Val Ser Tyr Ile Ser Ser Ser Ser Thr Ile Tyr Tyr Ala
 65                  70                  75                  80

Asp Ser Val Lys Gly Arg Phe Thr Ile Ser Arg Asp Asn Ala Lys Asn
                 85                  90                  95

Ser Leu Tyr Leu Gln Met Asn Ser Leu Arg Ala Glu Asp Thr Ala Val
            100                 105                 110

Tyr Tyr Cys Ala Arg
            115

(2) INFORMATION FOR SEQ ID NO: 131:

(i) SEQUENCE CHARACTERISTICS:
        (A) LENGTH: 119 amino acids
        (B) TYPE: amino acid
        (D) TOPOLOGY: linear (ii) MOLECULE TYPE: protein (xi) SEQUENCE DESCRIPTION: SEQ ID NO: 131:

Met Glu Phe Gly Leu Ser Trp Val Phe Leu Val Ala Ile Leu Lys Gly
  1               5                  10                  15

Val Gln Cys Glu Val Gln Leu Val Glu Ser Gly Gly Gly Leu Val Gln
             20                  25                  30

```
          Pro Gly Arg Ser Leu Arg Leu Ser Cys Thr Ala Ser Gly Phe Thr Phe
                   35                  40                  45

Gly Asp Tyr Ala Met Ser Trp Phe Arg Gln Ala Pro Gly Lys Gly Leu
           50                  55                  60

Glu Trp Val Gly Phe Ile Arg Ser Lys Ala Tyr Gly Gly Thr Thr Glu
           65                  70                  75                  80

Tyr Thr Ala Ser Val Lys Gly Arg Phe Thr Ile Ser Arg Asp Gly Ser
                           85                  90                  95

Lys Ser Ile Ala Tyr Leu Gln Met Asn Ser Leu Lys Thr Glu Asp Thr
                          100                 105                 110

Ala Val Tyr Tyr Cys Thr Arg
                  115

(2) INFORMATION FOR SEQ ID NO: 132:

(i) SEQUENCE CHARACTERISTICS:
         (A) LENGTH: 55 amino acids
         (B) TYPE: amino acid
         (D) TOPOLOGY: linear (ii) MOLECULE TYPE: protein (xi) SEQUENCE DESCRIPTION: SEQ ID NO: 132:

Met Glu Leu Gly Leu Ser Trp Val Ser Leu Val Ile Ile Leu Lys Gly
 1               5                  10                  15

Val Cys Gly Val Gln Met Val Glu Ser Trp Gly Glu Leu Ala Gln Xaa
                20                  25                  30

Glu Cys Ala Asp Ser Ala Val His Pro Leu Asn Pro Pro Ser Val Ala
                35                  40                  45

Thr Arg Ser Ala Glu Ser Ala
 50                  55

(2) INFORMATION FOR SEQ ID NO: 133:

(i) SEQUENCE CHARACTERISTICS:
         (A) LENGTH: 117 amino acids
         (B) TYPE: amino acid
         (D) TOPOLOGY: linear (ii) MOLECULE TYPE: protein (xi) SEQUENCE DESCRIPTION: SEQ ID NO: 133:

Met Gly Ser Thr Ala Ile Leu Ala Leu Leu Leu Ala Val Leu Gln Gly
 1               5                  10                  15

Val Cys Ser Glu Val Gln Leu Val Gln Ser Gly Ala Glu Val Lys Lys
                20                  25                  30

Pro Gly Glu Ser Leu Lys Ile Ser Cys Lys Gly Ser Gly Tyr Ser Phe
                35                  40                  45

Thr Ser Tyr Trp Ile Gly Trp Val Arg Gln Met Pro Gly Lys Gly Leu
 50                  55                  60

Glu Trp Met Gly Ile Ile Tyr Pro Gly Asp Ser Asp Thr Arg Tyr Ser
 65                  70                  75                  80

Pro Ser Phe Gln Gly Gln Val Thr Ile Ser Ala Asp Lys Ser Ile Ser
                 85                  90                  95

Thr Ala Tyr Leu Gln Trp Ser Ser Leu Lys Ala Ser Asp Thr Ala Met
                100                 105                 110

Tyr Tyr Cys Ala Arg
        115
```

-continued (2) INFORMATION FOR SEQ ID NO: 134:

(i) SEQUENCE CHARACTERISTICS:
        (A) LENGTH: 116 amino acids
        (B) TYPE: amino acid
        (D) TOPOLOGY: linear (ii) MOLECULE TYPE: protein (xi) SEQUENCE DESCRIPTION: SEQ ID NO: 134:

```
Met Glu Ser Gly Leu Ser Trp Val Phe Leu Val Ala Ile Leu Lys Gly
 1               5                  10                  15

Val Gln Cys Glu Val Gln Leu Val Glu Ser Gly Gly Leu Val Gln Pro
            20                  25                  30

Gly Gly Ser Leu Arg Leu Ser Cys Ala Ala Ser Gly Phe Thr Phe Ser
        35                  40                  45

Ser Ser Trp Met His Trp Val Cys Gln Ala Pro Glu Lys Gly Leu Glu
    50                  55                  60

Trp Val Ala Asp Ile Lys Cys Asp Gly Ser Glu Lys Tyr Tyr Val Asp
65                  70                  75                  80

Ser Val Lys Gly Arg Leu Thr Ile Ser Arg Asp Asn Ala Lys Asn Ser
                85                  90                  95

Leu Tyr Leu Gln Val Asn Ser Leu Arg Ala Glu Asp Met Thr Val Tyr
            100                 105                 110

Tyr Cys Val Arg
        115
```

(2) INFORMATION FOR SEQ ID NO: 135:

(i) SEQUENCE CHARACTERISTICS:
        (A) LENGTH: 116 amino acids
        (B) TYPE: amino acid
        (D) TOPOLOGY: linear (ii) MOLECULE TYPE: protein (xi) SEQUENCE DESCRIPTION: SEQ ID NO: 135:

```
Met Glu Phe Trp Leu Ser Trp Val Phe Leu Val Ala Ile Leu Lys Gly
 1               5                  10                  15

Val Gln Cys Glu Val Gln Leu Val Glu Ser Gly Gly Gly Leu Ile Gln
            20                  25                  30

Pro Gly Gly Ser Leu Arg Leu Ser Cys Ala Ala Ser Gly Phe Thr Val
        35                  40                  45

Ser Ser Asn Tyr Met Ser Trp Val Arg Gln Ala Pro Gly Lys Gly Leu
    50                  55                  60

Glu Trp Val Ser Val Ile Tyr Ser Gly Gly Ser Thr Tyr Tyr Ala Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Arg
        115
```

(2) INFORMATION FOR SEQ ID NO: 136:

(i) SEQUENCE CHARACTERISTICS:
        (A) LENGTH: 112 amino acids
        (B) TYPE: amino acid
        (D) TOPOLOGY: linear (ii) MOLECULE TYPE: protein (xi) SEQUENCE DESCRIPTION: SEQ ID NO: 136:

```
Met Glu Leu Gly Leu Ser Trp Val Phe Thr Val Thr Val Leu Lys Gly
  1               5                  10                  15

Val Gln Cys Glu Val Gln Leu Val Glu Ser Glu Glu Asn Gln Arg Gln
                 20                  25                  30

Leu Gly Gly Ser Leu Arg Leu Ser Cys Ala Asp Ser Gly Leu Thr Phe
             35                  40                  45

Ser Ser Tyr Met Ser Ser Asp Ser Gln Ala Pro Gly Lys Gly Leu Glu
 50                  55                  60

Val Val Asp Ile Asp Arg Ser Gln Leu Cys Tyr Ala Gln Ser Val Lys
 65                  70                  75                  80

Ser Arg Phe Thr Ile Ser Lys Glu Asn Ala Lys Asn Ser Leu Cys Leu
                 85                  90                  95

Gln Met Asn Ser Leu Arg Ala Glu Gly Thr Ala Val Tyr Tyr Cys Met
            100                 105                 110
```

(2) INFORMATION FOR SEQ ID NO: 137:

(i) SEQUENCE CHARACTERISTICS:
        (A) LENGTH: 120 amino acids
        (B) TYPE: amino acid
        (D) TOPOLOGY: linear (ii) MOLECULE TYPE: protein (xi) SEQUENCE DESCRIPTION: SEQ ID NO: 137:

```
Met Lys His Leu Trp Phe Phe Leu Leu Leu Val Ala Ala Pro Arg Trp
  1               5                  10                  15

Val Leu Ser Gln Val Gln Leu Gln Glu Ser Gly Pro Gly Leu Val Lys
                 20                  25                  30

Pro Ser Glu Thr Leu Ser Leu Ile Cys Ala Val Ser Gly Asp Ser Ile
             35                  40                  45

Ser Ser Gly Asn Trp Ile Trp Val Arg Gln Pro Pro Gly Lys Gly Leu
 50                  55                  60

Glu Trp Ile Gly Glu Ile His His Ser Gly Ser Thr Tyr Tyr Asn Pro
 65                  70                  75                  80

Ser Leu Lys Ser Arg Ile Thr Met Ser Val Asp Thr Ser Lys Asn Gln
                 85                  90                  95

Phe Tyr Leu Lys Leu Ser Ser Val Thr Ala Ala Asp Thr Ala Val Tyr
            100                 105                 110

Tyr Cys Ala Arg Tyr Thr Val Arg
            115                 120
```

(2) INFORMATION FOR SEQ ID NO: 138:

(i) SEQUENCE CHARACTERISTICS:
        (A) LENGTH: 69 amino acids
        (B) TYPE: amino acid
        (D) TOPOLOGY: linear (ii) MOLECULE TYPE: protein (xi) SEQUENCE DESCRIPTION: SEQ ID NO: 138:

```
Met Asp Trp Thr Trp Ser Ile Leu Phe Leu Val Ala Ala Thr Gly
  1               5                  10                  15

Ala His Ser Arg Val Gln Leu Val Gln Ser Gly Pro Glu Val Lys Gln
                 20                  25                  30
```

-continued

```
Pro Gly Ala Ser Ala Lys Val Ser Cys Lys Val Ser Gly Thr Val Ile
            35                  40                  45

Thr Tyr Gly Met Asn Trp Ile Arg Gln Thr Pro Gly Gln Gly Leu Glu
 50                  55                  60

Trp Met Gly Trp Ile
 65
```

(2) INFORMATION FOR SEQ ID NO: 139:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO: 139:

```
Met Asp Trp Ile Trp Arg Ile Leu Phe Leu Val Gly Ala Ala Ile Gly
 1               5                  10                  15

Ala His Ser Gln Met Gln Leu Val Gln Ser Gly Pro Glu Val Lys Lys
            20                  25                  30

Pro Gly Thr Ser Val Lys Val Ser Cys Lys Ala Ser Gly Phe Thr Phe
            35                  40                  45

Thr Ser Ser Ala Val Gln Trp Val Arg Gln Ala Arg Gly Gln Arg Leu
 50                  55                  60

Glu Trp Ile Gly Trp Ile Val Val Gly Ser Gly Asn Thr Asn Tyr Ala
 65                  70                  75                  80

Gln Lys Phe Gln Glu Arg Val Thr Ile Thr Arg Asp Met Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Ala
            115
```

(2) INFORMATION FOR SEQ ID NO: 140:

(i) SEQUENCE CHARACTERISTICS:
        (A) LENGTH: 116 amino acids
        (B) TYPE: amino acid
        (D) TOPOLOGY: linear (ii) MOLECULE TYPE: protein (xi) SEQUENCE DESCRIPTION: SEQ ID NO: 140:

```
Met Lys His Leu Trp Phe Phe Leu Leu Val Ala Ala Pro Arg Trp
 1               5                  10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Val
            35                  40                  45

Ser Ser Tyr Tyr Trp Ser Trp Ile Arg Gln Pro Pro Gly Lys Gly Leu
 50                  55                  60

Glu Trp Ile Gly Tyr Ile Tyr Tyr Ser Gly Ser Thr Asn Tyr Asn Pro
 65                  70                  75                  80

Ser Leu Lys Ser Arg Val Thr Ile Ser Val Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg
```

115

(2) INFORMATION FOR SEQ ID NO: 141:

(i) SEQUENCE CHARACTERISTICS:
        (A) LENGTH: 113 amino acids
        (B) TYPE: amino acid
        (D) TOPOLOGY: linear (ii) MOLECULE TYPE: protein (xi) SEQUENCE DESCRIPTION: SEQ ID NO: 141:

```
Met Glu Ser Gly Leu Ser Trp Ile Phe Leu Val Ala Val Leu Lys Gly
 1               5                  10                  15
Cys Pro Val Gly Ala Ala Gly Gly Val Trp Gly Arg Leu Ser Lys Asp
            20                  25                  30
Trp Gly Val Ser Glu Thr Leu Leu Cys Ser Leu Trp Ile His Leu Gln
        35                  40                  45
Leu Cys Tyr Ala Leu Gly Pro Pro Gly Ser Arg Lys Gly Phe Gly Val
    50                  55                  60
Gly Leu Ser Tyr Tyr Lys Trp Tyr Arg Thr Leu His Arg Leu Cys Glu
65                  70                  75                  80
Gly Leu Ile His His Leu Arg Gln Cys Pro Glu Phe Thr Val Ser Ala
                85                  90                  95
Asn Glu Gln Pro Glu Ser Arg Arg His Gly Cys Val Leu Leu Cys Glu
            100                 105                 110
Arg
```

(2) INFORMATION FOR SEQ ID NO: 142:

(i) SEQUENCE CHARACTERISTICS:
        (A) LENGTH: 118 amino acids
        (B) TYPE: amino acid
        (D) TOPOLOGY: linear (ii) MOLECULE TYPE: protein (xi) SEQUENCE DESCRIPTION: SEQ ID NO: 142:

```
Met Lys His Leu Trp Phe Phe Leu Leu Leu Val Ala Ala Pro Arg Trp
 1               5                  10                  15
Val Leu Ser Gln Val Gln Leu Gln Glu Ser Gly Pro Gly Leu Val Lys
            20                  25                  30
Pro Ser Glu Thr Leu Ser Leu Thr Cys Thr Val Ser Gly Gly Ser Val
        35                  40                  45
Ser Ser Gly Ser Tyr Tyr Trp Ser Trp Ile Arg Gln Pro Pro Gly Lys
    50                  55                  60
Gly Leu Glu Trp Ile Gly Tyr Ile Tyr Tyr Ser Gly Ser Thr Asn Tyr
65                  70                  75                  80
Asn Pro Ser Leu Lys Ser Arg Val Thr Ile Ser Val Asp Thr Ser Lys
                85                  90                  95
Asn Gln Phe Ser Leu Lys Leu Ser Ser Val Thr Ala Ala Asp Thr Ala
            100                 105                 110
Val Tyr Tyr Cys Ala Arg
        115
```

(2) INFORMATION FOR SEQ ID NO: 143:

(i) SEQUENCE CHARACTERISTICS:
        (A) LENGTH: 116 amino acids
        (B) TYPE: amino acid (D) TOPOLOGY: linear (ii) MOLECULE TYPE: protein (xi) SEQUENCE DESCRIPTION: SEQ ID NO: 143:

```
Met Glu Phe Gly Leu Ser Trp Val Phe Leu Val Ala Asn Leu Arg Gly
  1               5                  10                  15

Val Gln Cys Glu Val Gln Leu Val Glu Ser Gly Glu Gly Leu Val Gln
             20                  25                  30

Pro Gly Gly Ser Leu Arg Leu Ser Cys Ala Ala Ser Gly Phe Thr Phe
         35                  40                  45

Ser Ser Ser Ala Met His Trp Val Arg Gln Ala Pro Arg Lys Gly Leu
 50                  55                  60

Trp Val Ser Val Ile Ser Thr Ser Gly Asp Thr Val Leu Tyr Thr Asp
 65                  70                  75                  80

Ser Val Lys Gly Arg Phe Thr Ile Ser Arg Asp Asn Ala Gln Asn Ser
                 85                  90                  95

Leu Ser Leu Gln Met Asn Ser Leu Arg Ala Glu Gly Thr Val Val Tyr
            100                 105                 110

Tyr Cys Val Lys
            115
```

(2) INFORMATION FOR SEQ ID NO: 144:

(i) SEQUENCE CHARACTERISTICS:
(A) LENGTH: 115 amino acids
(B) TYPE: amino acid
(D) TOPOLOGY: linear (ii) MOLECULE TYPE: protein (xi) SEQUENCE DESCRIPTION: SEQ ID NO: 144:

```
Met Gly Phe Glu Leu Thr Arg Ile Phe Leu Val Ala Ile Leu Lys Gly
  1               5                  10                  15

Val Gln Cys Glu Val Glu Leu Ile Glu Ser Ile Glu Gly Leu Arg Gln
             20                  25                  30

Leu Gly Lys Phe Leu Arg Leu Ser Cys Val Ala Ser Gly Phe Thr Phe
         35                  40                  45

Ser Ser Tyr Met Ser Trp Val Asn Glu Thr Leu Gly Lys Gly Leu Glu
 50                  55                  60

Gly Val Ile Asp Val Lys Tyr Asp Gly Ser Gln Ile Tyr His Ala Asp
 65                  70                  75                  80

Ser Val Lys Gly Arg Phe Thr Ile Ser Lys Asp Asn Ala Lys Asn Ser
                 85                  90                  95

Pro Tyr Leu Gln Thr Asn Ser Leu Arg Ala Glu Asp Met Thr Met His
            100                 105                 110

Gly Cys Thr
            115
```

(2) INFORMATION FOR SEQ ID NO: 145:

(i) SEQUENCE CHARACTERISTICS:
(A) LENGTH: 118 amino acids
(B) TYPE: amino acid
(D) TOPOLOGY: linear (ii) MOLECULE TYPE: protein (xi) SEQUENCE DESCRIPTION: SEQ ID NO: 145:

Met Thr Glu Phe Gly Leu Ser Trp Val Phe Leu Val Ala Ile Phe Lys

-continued

```
  1               5              10              15
Gly Val Gln Cys Glu Val Gln Leu Val Glu Ser Gly Gly Gly Leu Val
            20                  25                  30

Gln Pro Gly Gly Ser Leu Arg Leu Ser Cys Ala Ala Ser Gly Phe Thr
            35                  40                  45

Phe Ser Ser Tyr Ala Met His Trp Val Arg Gln Ala Pro Gly Lys Gly
        50                  55                  60

Leu Glu Tyr Val Ser Ala Ile Ser Ser Asn Gly Gly Ser Thr Tyr Tyr
65                  70                  75                  80

Ala Asn Ser Val Lys Gly Arg Phe Thr Ile Ser Arg Asp Asn Ser Lys
            85                  90                  95

Asn Thr Leu Tyr Leu Gln Met Gly Ser Leu Arg Ala Glu Asp Met Ala
            100                 105                 110

Val Tyr Tyr Cys Ala Arg
            115
```